US009205094B2

(12) United States Patent
Currie

(10) Patent No.: US 9,205,094 B2
(45) Date of Patent: Dec. 8, 2015

(54) COMPOSITIONS COMPRISING BILE ACID SEQUESTRANTS FOR TREATING ESOPHAGEAL DISORDERS

(75) Inventor: Mark G. Currie, Sterling, MA (US)

(73) Assignee: IRONWOOD PHARMACEUTICALS, INC., Cambridge, MA (US)

( * ) Notice: Subject to any disclaimer, the term of this patent is extended or adjusted under 35 U.S.C. 154(b) by 1271 days.

(21) Appl. No.: 12/520,748

(22) PCT Filed: Dec. 21, 2007

(86) PCT No.: PCT/US2007/088624
§ 371 (c)(1),
(2), (4) Date: Feb. 18, 2010

(87) PCT Pub. No.: WO2008/080092
PCT Pub. Date: Jul. 3, 2008

(65) Prior Publication Data
US 2010/0179235 A1    Jul. 15, 2010

Related U.S. Application Data

(60) Provisional application No. 60/871,499, filed on Dec. 22, 2006.

(51) Int. Cl.
| B01J 41/14 | (2006.01) |
| A61K 31/575 | (2006.01) |
| A61K 31/195 | (2006.01) |
| A61K 31/27 | (2006.01) |
| A61K 31/341 | (2006.01) |
| A61K 31/4164 | (2006.01) |
| A61K 31/4184 | (2006.01) |
| A61K 31/426 | (2006.01) |
| A61K 31/4439 | (2006.01) |
| A61K 31/444 | (2006.01) |
| A61K 31/785 | (2006.01) |
| A61K 33/08 | (2006.01) |
| A61K 33/10 | (2006.01) |
| A61K 45/06 | (2006.01) |

(52) U.S. Cl.
CPC ............. *A61K 31/575* (2013.01); *A61K 31/195* (2013.01); *A61K 31/27* (2013.01); *A61K 31/341* (2013.01); *A61K 31/4164* (2013.01); *A61K 31/4184* (2013.01); *A61K 31/426* (2013.01); *A61K 31/444* (2013.01); *A61K 31/4439* (2013.01); *A61K 31/785* (2013.01); *A61K 33/08* (2013.01); *A61K 33/10* (2013.01); *A61K 45/06* (2013.01)

(58) Field of Classification Search
CPC ............ A61K 31/2054; A61K 9/2077; A61K 9/4891; A61K 31/717; A61K 8/042; A61K 31/785; A61K 9/2054
See application file for complete search history.

(56) References Cited

U.S. PATENT DOCUMENTS 3,624,209 A    11/1971 Granatek et al.
4,172,120 A    10/1979 Fryers et al.
2002/0015690 A1    2/2002 Green et al.
2003/0219401 A1*    11/2003 Keller et al. ................. 424/78.1
2004/0062802 A1    4/2004 Hermelin
2004/0180088 A1*    9/2004 Dudhara et al. .............. 424/471
2004/0234608 A1*    11/2004 Fleshner-Barak et al. .... 424/488
2005/0147580 A1*    7/2005 Connor et al. ............. 424/78.12
2006/0073213 A1    4/2006 Hotamisligil et al.
2008/0020018 A1    1/2008 Moodley et al.
2008/0103122 A1    5/2008 Veltri

FOREIGN PATENT DOCUMENTS

| DE | 2074425 A1 | 8/1978 |
| EP | 0005129 B1 | 4/1981 |
| EP | 0124495 B1 | 1/1987 |
| EP | 0508312 A | 10/1992 |
| EP | 1396265 A | 3/2004 |
| WO | WO 98/11885 A1 | 3/1998 |
| WO | 0209814 A2 | 2/2002 |
| WO | WO 02/096404 A1 | 12/2002 |
| WO | WO 03/090731 A1 | 11/2003 |
| WO | 2006088305 A | 8/2006 |
| WO | 2008080092 A2 | 7/2008 |
| WO | 2009158625 A2 | 12/2009 |

OTHER PUBLICATIONS

Fitzgerald et al., Journal of Clinical Investigation, (Nov. 1996), 98(9), pp. 2120-2127.*
Kinoshita et al., Journal of Gastroenterology (Abstract), (Mar. 2003), 38(Suppl. 15), pp. 13-19.*
www.redorbit.com/news/health/702584/xenoport_announces_positive_results_from_. . . retrieved fom the Internet Sep. 20, 2012, originally published Oct. 22, 2006.*
Yehuda Handelsman, MD, Diabetes Care, vol. 34, Supplement 2, May 2011.*
Farmer et al. Baillieres Clin Endocrinol Metab. Oct. 1995;9(4):825-47.*
Tonstad et al, Archives of Disease in Childhood 1996; 74: 157-160.*
Lind et al, Gut, 1983, 24, 270-276.*
Klausner et al., Journal of Controlled Release 90 (2003) 143-162.*
Streubel et al., Current Opinion in Pharmacology 2006, 6:501-508.*
Farmer et al (Baillière's Clinical Endocrinology and Metabolism. vol. 9, Issue 4, Oct. 1995, pp. 825-847).*
McQuaid et al (Aliment Pharmacal Ther 2011; 34: 146-165).*
International Search Report for PCT/US2009/048870 dated Feb. 17, 2010.
International Search Report for PCT/US2007/088624 dated May 15, 2008.
Buttar Navtej et al, "Ursodeoxycholic acid as a chemopreventive agent in Barrett's esophagus: An in-vitro study," Gastroenterology, Apr. 2002, pp. A-292, vol. 122, No. 4 Suppl. 1, and Digestive Disease Week and the 103rd Gastroenterological Association; San Francisco, CA, USA; May 19-22, 2002.

(Continued)

Primary Examiner — Savitha Rao
Assistant Examiner — Angela Brown-Pettigrew
(74) Attorney, Agent, or Firm — Heslin Rothenberg Farley & Mesiti P.C.

(57) ABSTRACT

Compositions comprising a therapeutically effective amount of at least one bile acid sequestrant are disclosed for treating or preventing upper GI tract disorders and protecting stratified squamous epithelium against injury by a noxious substance. Exemplary bile acid sequestrants include colesevelam, colesevelam hydrochloride, colestipol, sevelamer and combinations thereof. The disclosed methods generally include administering to a patient in need thereof a therapeutically effective amount of a pharmaceutical composition comprising at least one bile acid sequestrant, alone or in combination with at least one proton pump inhibitor.

12 Claims, No Drawings

(56) References Cited

OTHER PUBLICATIONS

Jauhonen P et al, "Succesful treatment of alkaline esophagitis with low-does cholestyramine: A case report," Scandinavian Journal of Gastroenterology, 1998, p. 24, vol. 33, No. SUPPL-227.

Richter Joel E, "Duodenogastric reflux-induced (alkaline) esophagitis," Current Treatment Options in Gastroenterology, Current Science, Philadelphia, PA, US, vol. 7, No. 1, 2004, pp. 53-58.

Simoni P et al, "Bioavailability study of a new, sinking enteric-coated ursodeoxycholic acid formulation," Pharmacological Research, Academic Press, London, GB, vol. 31, No. 2, 1995, pp. 115-119.

"Squamous epithelium" found in MeSH databases, [on line] [downloaded Dec. 6, 2011] (found in Pubmed database).

Internet citation, www.fobdo.ru/zhenskaya_konsultacija/originalyiy_skvamoznyiy_epiteliiy_; found Oct. 25, 2011.

Mashovsky, MD, Drugs, M, "New wave", p. 530, article "ursodeoxycholic acid." 2005.

Rivkin VL et al., M, ABBYY Press, (New English-Russian medical dictionary), 2009, p. 691, article "Sequestrant".

Sikiric P, et al. "Long-lasting cytoprotection after pentadecapeptide BPC 157, ranitidine, sucralfate or cholestyramine application in reflux oesophagitis in rats", J Physiol Paris, Dec. 1999, 93(6):467-77; Abstract PMID: 10672991.

Bueverov AV, et al. "Duogastroesophagial efflux as a cause of reflux esophagitis", Pharmateka, 2006, No. 1 (116), pp. 22-27, chapter "Treatment approaches."

Huo X, et al. "Deoxycholic acid causes DNA damage while inducing apoptotic resistance through NF-κB activation in benign Barrett's epithelial cells"; American Journal of Physiology, vol. 301, Issue 2, Pt. 1, pp. G278-G286 Journal 2011.

Nicolai et al, "Comparison of the Combination of Cholestyramine/Alginates with Placebo in the Treatment of Postgastrectomy Biliary Reflux Gastritis", Eur. J. Clin. Pharmacol., 1981, 21, 189-194.

Steinmetz Karen L et al: "Colesevelam: Potential uses for the newest bile resin", Cardiovascular Drug Reviews, US, vol. 23, No. 1, 2005, pp. 15-30, XP007917963, ISSN: 0897-5957.

Castell, Donald O. et al., "XP19986 decreases reflux and is well tolerated in GERD patients", American Journal of Gastroenterology, Elsevier Science, Inc., US, vol. 101, No. 9, suppl S, Sep. 1, 2006, pp. S59.

"Dosing with colestipol" http://drugs.emedtv.com/colestipol/dosing-with-colestipol.html 2007.

"Dosing with omeprazole" http://drugs.emedtv.com/omeprazole/omeprazole-dosing.html 2006-2012.

Black RB et al. "A controlled clinical trial of cholestyramine in the treatment of gastric ulcer". Gastroenterology. 1971,61(6):821-5.

Scudamore HH et al. "Bile reflux gastritis. Diagnosis, medical and surgical therapy". Am. J. Gastroenterology, 1973, 60, 9-22.

Mersereau WA, Hinchey EJ. "Prevention of bile reflux-induced acute gastric ulceration in the rat by cholestyramine". Ann. of Surgery, 1974, 179, 883-888.

Zike WL et al. "The role of cholestyramine in the prevention of stress ulcers". J Surg Res. Nov. 1974;17(5):315-9.

Stanciu C, Bennett JR. "Alginate/antacid in the reduction of gastro-oesophageal reflux". Lancet, 1974, 1, 109-111.

Eastwood GL. "Failure of cholestyramine to prevent bile acid injury to mouse gastric mucosa". Gastroenterology, 1975, 68, 1466-1472.

Lindenbaum S and Higuchi T. "Binding of bile acids to cholestyramine at gastric pH conditions". J. Pharmac. Sciences, 1975, 64(11):1887-1889.

Schumpelick V, Grossner D. "[First Clinical experiences with cholestyramine for the prophylaxis of stress ulcer (author's transl)]." Münchener Medizinische Wochenschrift. Oct. 1977, 119:1329-1332.

Meshkinpour JI. "Effects of cholestyramine on the symptoms of reflux gastritis: a randomized, double blind, cross-over study". Gastroenterology, 1977, 73, 441-443.

Llewellyn AF et al. "The binding of bile acids by hydrotalcite and other antacid preparations". Pharm Acta Helv., 1977, 52, 1-5.

Salmon R, Hem B. "Bile reflux esophagitis. A critical study of two models in the rat". Digestion, 1981, 22(2), 73-9.

Mangnall Y.F. et al. "The ability of antacids and cholestyramine to bind bile acids: effect of pH". Scand. J. of Gastroenterology, 1986, 21(7), 789-794.

Burton et al. "Intragastric Distribution of Ion-Exchange resins: a Drug Delivery system for the Topical treatment of the Gastric mucosa". J. Pharma. Pharmacol. 1995, 47, 901-906.

Jackson et al. "Effects of resin surface charge on gastric mucoadhesion and residence of cholestyramine". Int J Pharmaceutics, 2000, 205, 173-181.

Jackson et al. "Comparative scintigraphic assessment of the intragastric distribution and residence of cholestyramine, carbopol 934P and sucralfate". Eur. J. Pharmaceutics and Biopharmaceutics, 2001, 212, 55-62.

Umamaheshwari RB et al. "A new approach in gastroretentive drug delivery system using cholestyramine". Drug delivery (Jul. 2003) vol. 10 pp. 151-160.

D. Kotlar et al. "The effect of Cholestyramine in patients with duodeno-gastro-esophageal reflux. A prospective study". Presentation given May 21, 2007.

Araki Y et al. "The herbal medicine rikkunshito exhibits strong and differential adsorption properties for bile salts". Experimental and Therapeutic Medicine, 2012, 3, 645-49.

Jackson SJ and Perkins AC. "In vitro assessment of the mucoadhesion of cholestyramine to porcine and human gastric mucosa". Eur. J. Pharmaceutics and Biopharmaceutics, 2001, 52, 121-127.

Siddiqui A et al., "Esophageal Visceral Sensitivity to Bile Salts in Patients with Functional Heartburn and in Healthy Control Subjects"; Digestive Diseases and Sciences, vol. 50, No. 1 (Jan. 2005), pp. 81-85.

Bachir GS et al., "Diagnosis of Incipient Reflux Esophagitis: a New Test"; South Medical Journal, vol. 74, Num. 9, p. 1072, 1981.

Farre R et al., "Short exposure of oesophageal mucosa to bile acids, both in acidic and weakly acidic conditions can impair mucosal integrity and provoke dilated intercellular spaces"; Gut, 2008, Downloaded from gut.bmj.com on Jul. 31, 2008.

Nehra D et al., "Toxic bile acids in gastro-oesophageal reflux disease: influence of gastric acidity"; Gut 1999;44:598-602.

Gotley DC et al., "Composition of gastro-oesophageal refluxate"; Gut, 1991,32, 1093-1099.

Iftikhar SY et al., "Bile reflux in columnar-lined Barrett's oesophagus"; Annals of The Royal College of Surgeons of England (1993) vol. 75, 411-416.

Tack J et al., "Gastro Esophageal Reflux Disease Poorly Responsive to Single-dose Proton Pump Inhibitors in Patients without Barrett's Esophagus: Acid Reflux, Bile Reflux or Both?"; Am. J. Gastroenterology, 2004, 981.

Gasiorowska A et al., "Comparison of the Degree of Duodenogastroesophageal Refl ux and Acid Refl ux Between Patients Who Failed to Respond and Those Who Were Successfully Treated With a Proton Pump Inhibitor Once Daily"; Am J Gastroenterol advance online publication, Jun. 2, 2009; doi: 10.1038/ajg.2009.240.

Monaco L et al., World J Gastroenterology, 2009.

Kunsch S et al., Digestion, 2012.

Yoshida N et al., Aliment Pharmacol Ther 2006.

Jolly AJ et al., "Acid and bile salts induce DNA damage in human oesophageal cell lines"; Mutagenesis vol. 19 No. 4 pp. 319-324, 2004.

Jenkins GJS et al., "The bile acid deoxycholic acid (DCA) at neutral pH activates NF-kB and induces IL-8 expression in oesophageal cells in vitro"; Carcinogenesis vol. 25 No. 3 pp. 317-323, 2004.

Burnat G et al, "Bile acids induce overexpression of homeobox gene CDX-2 and vascular endothelial growth factor (VEGF) in human Barrett's esophageal mucosa and adenocarcinoma cell line"; Scandinavian Journal of Gastroenterology, 2007; 42: 1460 1465.

Reveiller M et al., "Bile Exposure Inhibits Expression of Squamous Differentiation Genes in Human Esophageal Epithelial Cells"; Ann Surg 2012;00:1-8).

Morita S et al., Carcinogenesis 2011.

AGA Abstracts, Gastroenterology, 2004, vol. 126, suppl. 2, 586-659.

Yoshida N, J. Cin. Biochem. Nutr., 40, 13-23, 2007.

http://reference.medscape.com/drug/welchol-colesevelam-342449; No date given; webpage copyright 1994-2014.

* cited by examiner

COMPOSITIONS COMPRISING BILE ACID SEQUESTRANTS FOR TREATING ESOPHAGEAL DISORDERS

BACKGROUND

The present application relates generally to combinations of compounds and methods for treating upper gastrointestinal tract disorders. More particularly, the present application relates to the use of at least one bile acid sequestrant for treating esophageal disorders.

The esophagus carries food, liquids, and saliva from the mouth to the stomach by coordinated contractions of its muscular lining. This process is automatic and people are usually not aware of it. Many people have felt their esophagus when they swallow something too large, try to eat too quickly, or drink very hot or very cold liquids. They then feel the movement of the food or drink down the esophagus into the stomach, which may be an uncomfortable sensation.

The muscular layers of the esophagus are normally pinched together at both the upper and lower ends by muscles called sphincters. When a person swallows, the sphincters relax automatically to allow food or drink to pass from the mouth into the stomach. The muscles then close rapidly to prevent the swallowed food or drink from leaking out of the stomach back into the esophagus or into the mouth. These sphincters make it possible to swallow while lying down or even upside-down. When people belch to release swallowed air or gas from carbonated beverages, the sphincters relax and small amounts of food or drink may come back up briefly; this condition is called reflux. The esophagus quickly squeezes the material back into the stomach. This amount of reflux and the reaction to it by the esophagus are considered normal.

While most people are familiar with acid reflux—the backflow of caustic stomach acids into the esophagus—bile reflux, which occurs when bile—a digestive fluid produced in the liver—flows upward (refluxes) from the small intestine into the stomach and esophagus, is less well known. Bile reflux often accompanies acid reflux, and together may lead to inflammation of the esophageal lining and potentially increased risk of esophageal cancer. See MG (1999) 94(12): 3649-3650. Bile reflux also affects the stomach, where it causes further inflammation.

Unlike acid reflux, bile reflux usually can't be controlled by changes in diet or lifestyle. Instead, bile reflux is most often managed with certain medications or, in severe cases, with surgery. Neither solution is uniformly effective, however, and some people continue to experience bile reflux even after treatment.

Bile reflux can be difficult to distinguish from acid reflux—the signs and symptoms are similar, and the two conditions frequently occur at the same time. Unlike acid reflux, bile reflux inflames the stomach, often causing a gnawing or burning pain in the upper abdomen. Other signs and symptoms may include: frequent heartburn, i.e., a burning sensation in the chest that sometimes spreads to the throat along with a sour taste in the mouth; nausea; vomiting bile; a cough; or hoarseness.

Bile and stomach acid reflux into the esophagus when the lower esophageal sphincter (LES), malfunctions. The LES separates the esophagus and stomach. Normally, it opens only to allow food to pass into the stomach and then closes tightly. But if the valve relaxes abnormally or weakens, stomach acid and bile can wash back into the esophagus, causing heartburn and ongoing inflammation that may lead to serious complications.

A sticky mucous coating protects the stomach from the corrosive effects of stomach acid, but the esophagus lacks this protection, which is why bile reflux and acid reflux can seriously damage esophageal tissue. And although bile reflux can injure the esophagus on its own—even when the pH of the reflux is neutral or alkaline—the combination of bile and acid reflux seems to be particularly harmful, increasing the risk of complications, such as: Gastroesophageal reflux disease, or GERD; Barrett's esophagus; esophageal cancer, and gastritis.

GERD is a generic term encompassing diseases with various digestive symptoms such as pyrosis, acid regurgitation, obstructed admiration, aphagia, pectoralgia, permeating feeling and the like sensibility caused by reflux in the esophagus and stagnation of gastric contents, duodenal juice, pancreatic juice and the like. The term covers both of reflux esophagitis in which erosion and ulcers are endoscopically observed, and esophageal regurgitation-type non-ulcer dyspepsia (NUD) in which no abnormality is endoscopically observed. GERD occurs when the LES does not close properly and stomach contents leak back, or reflux, into the esophagus.

A hiatal hernia may contribute to causing GERD and can happen in people of any age. Other factors that may contribute to GERD include, but are not limited to, alcohol use, overweight, pregnancy, smoking, Zollinger-Ellison syndrome, hypercalcemia, and scleroderma. Also, certain foods can be associated with reflux events, including, citrus fruits, chocolate, drinks with caffeine, fatty and fried foods, garlic and onions, mint flavorings, spicy foods, and tomato-based foods, like spaghetti sauce, chili, and pizza.

The inner mucosa of the esophagus is lined with nonkeratinized stratified squamous epithelium arranged in longitudinal folds. Damage to the lining of the esophagus causes the normal squamous cells that line the esophagus to turn into a type of cell not usually found in humans, called specialized columnar cells. That conversion of cells in the esophagus by the acid reflux, is known as Barrett's Esophagus. Although people who do not have heartburn can have Barrett's esophagus, it is found about three to five times more often in people with this condition. Barrett's esophagus does not cause symptoms itself and is important only because it seems to precede the development of a particular kind of cancer—esophageal adenocarcinoma. The risk of developing adenocarcinoma is 30 to 125 times higher in people who have Barrett's esophagus than in people who do not. This type of cancer is increasing rapidly in white men. This increase may be related to the rise in obesity and GERD.

Barrett's esophagus has no cure, short of surgical removal of the esophagus, which is a serious operation. Surgery is recommended only for people who have a high risk of developing cancer or who already have it. Most physicians recommend treating GERD with acid-blocking drugs, since this is sometimes associated with improvement in the extent of the Barrett's tissue. However, this approach has not been proven to reduce the risk of cancer. Treating reflux with a surgical procedure for GERD also does not seem to cure Barrett's esophagus. Several different experimental approaches are under study. One attempts to see whether destroying the Barrett's tissue by heat or other means through an endoscope can eliminate the condition. This approach, however, has potential risks and unknown effectiveness.

Esophageal cancer can occur almost anywhere along the length of the esophagus, but it frequently starts in the glandular cells closest to the stomach (adenocarcinoma). Because esophageal cancer may not be diagnosed until it's quite advanced, the outlook for people with the disease is often poor. The risk of cancer of the esophagus is increased by long-term irritation of the esophagus, such as with smoking, heavy alcohol intake, and Barrett's esophagitis. Thus, there is a link between esophageal cancer and bile reflux and acid reflux. In animal models, bile reflux alone has been shown to cause cancer of the esophagus.

There are numerous medications available that can effectively treat heartburn and indigestion. Presently, the main therapies employed in the treatment of GERD and upper GI tract disorders include agents for reducing the stomach acidity, for example by using the histamine $H_2$-receptor antagonists or proton pump inhibitors (PPIs). $H_2$ blockers are drugs that inhibit the production of acid in the stomach. Exemplary histamine $H_2$-receptor antagonists include, for example, cimetidine (as sold under the brand-name TAGAMET HB®), famotidine (as sold under the brand-name PEPCID AC®), nizatidine (as sold under the brand-name AXID AR®), and ranitidine (as sold under the brand-name ZANTAC 75®). Both types of medication are effective in treating heartburn and usually eliminate symptoms within a short period of time.

PPIs act by inhibiting the parietal cell $H^+/K^+$ ATPase proton pumps responsible for acid secretion from these cells. PPIs, such as omeprazole, and its pharmaceutically acceptable salts are disclosed, for example, in EP 05129, EP 124495 and U.S. Pat. No. 4,255,431.

Despite their well-documented efficacy, PPIs have notable limitations. These drugs exhibit substantial inter-patient variability in pharmacokinetics and may have significant interactions with other drugs. For example, patients who are non-responsive to treatment with PPI inhibitor alone may be non-responsive because even though the PPI is decreasing acid reflux from the stomach, bile acid from the duodenum is still present. Thus, an improvement of PPI-mediated activity is a well-recognized challenge in gastroenterology and there is a need in the art to address and overcome upper GI tract disorders that are non-responsive to treatment by administration of PPIs alone.

Accordingly, the development of an effective treatment for pathologies in which inhibition of one or both of gastric acid secretion and bile acid secretion is required would be useful.

SUMMARY

Briefly, the present application discloses a treatment for upper gastrointestinal disorders in which the inhibition of one or both of gastric acid secretion and bile acid secretion is desirable.

In accordance with the above, the present application discloses compositions and methods for treating or preventing upper GI tract disorders such as, for example, gastroesophageal reflux disease (GERD), heartburn, indigestion, dyspepsia, erosive esophagitis, peptic ulcer, gastric ulcer, NSAID-associated ulcers, duodenal ulcers, esophageal ulcers, esophagitis, laryngitis, ulcers arising from Meckel's diverticulum, Barrett's Esophagus, esophageal adenocarcinoma, pharyngitis, and GERD-related pulmonary dysfunction (e.g., asthma and/or cough).

In a first aspect, compositions containing a therapeutically effective amount of at least one bile acid sequestrant, wherein the compositions are useful for treating or preventing an upper GI tract disorder, or for protecting the stratified squamous epithelium against injury by a noxious substance, are disclosed.

In certain embodiments, the bile acid sequestrant includes, but is not limited to, cholestyramine (i.e., QUESTRAN®, QUESTRAN LIGHT®, CHOLYBAR®, CA registry no. 11041-12-6), colesevelam (i.e., WELCHOL®, CA registry nos. 182815-43-6 and 182815-44-7), ursodeoxycholic acid (i.e. CA registry no. 128-13-2), colestipol (i.e., COLES-TID®, CA registry nos. 50925-79-6 and 37296-80-3), sevelamer, dialkylaminoalkyl derivatives of a cross-linked dextran, LOCHOLEST®, DEAE-Sephadex (SECHOLEX®, POLIDEXIDE®), water soluble derivatives such as 3,3-ioene, N-(cycloalkyl)alkylamines and poliglusam, insoluble quaternized polystyrenes, saponins and mixtures thereof, those bile acid sequestrants disclosed in WO97/11345, WO98/57652, U.S. Pat. No. 3,692,895, and U.S. Pat. No. 5,703,188, including pharmaceutically acceptable salts or mixtures thereof. Suitable inorganic cholesterol sequestrants include bismuth salicylate plus montmorillonite clay, aluminum hydroxide and calcium carbonate antacids.

In other embodiments, the compositions containing a therapeutically effective amount of at least one bile acid sequestrant can additionally include a therapeutically effective amount of at least one proton pump inhibitor.

In certain embodiments, the proton pump inhibitor includes, for example, any of the following compounds: omeprazole (i.e., PRILOSEC®, ZEGERID®, LOSEC®, CA registry no. 73590-58-6), esomeprazole (i.e., NEXIUM®, perprazole, s-omeprazole magnesium, CA registry no. 161973-10-0), lansoprazole (i.e., PREVACID®, ZOTON®, INHIBITOL®, CA registry no. 103577-45-3), pantoprazole (i.e., PROTONIX®, PROTIUM®, SOMAC®, PANTOLOC®, CA registry no. 102625-70-7), rabeprazole (i.e., RABECID®, ACIPHEX®, PARIET®, habeprazole, pariprazole, CA registry nos. 117976-89-3 and 117976-90-6), tenatoprazole (i.e., benatoprazole, S-Tenatoprazole-Na STU-Na, CA registry no. 113712-98-4), leminoprazole (i.e., CA registry no. 104340-86-5), dontoprazole (i.e., CA registry no. 350507-35-6), ransoprazole (i.e., CA registry no. 832103-67-0), or pharmaceutically acceptable salts or mixtures thereof.

In other embodiments, the compositions described herein (whether prepared as a bile acid sequestrant alone or co-formulated with a proton pump inhibitor) can be further formulated to optionally include any one or a combination of the numerous commercially available, over-the-counter (OTC) medications for reducing the stomach acidity employed to treat GERD and other upper GI tract disorders. Such commercially available OTC medications include, but are not limited to, histamine $H_2$-receptor antagonists and antacids.

Exemplary histamine H2-receptor antagonists include, for example, cimetidine (as sold under the brand-name TAGAMET HB®), famotidine (as sold under the brand-name PEPCID AC®), nizatidine (as sold under the brand-name AXID AR®), and ranitidine (as sold under the brand-name ZANTAC 75®).

Exemplary antacids include, but are not limited to, insoluble inorganic salts such as calcium carbonate, magnesium carbonate, calcium hydroxide, magnesium hydroxide, or aluminum hydroxide. Typical consumer antacid products include, but are not limited to, TUMS®, MILK of MAGNESIA®, MAALOX PLUS®, ALKA-SELTZER®, MYLANTA®, PEPTO-BISMOL®, RIOPAN®, and ROLAIDS®.

In still other embodiments, the compositions described herein (whether prepared as a bile acid sequestrant alone or co-formulated with a proton pump inhibitor and another agent) can be further formulated to optionally include any one or a combination of γ-aminobutyricacid-b (GABA-B) agonists, prodrugs of GABA-B agonists, and protease inhibitors.

Exemplary GABA-B agonists, include, for example, baclofen. In an embodiment, the GABA-B agonist is R-baclofen.

Exemplary prodrugs of GABA-B agonists include, for example, XP19986 (CAS Registry No. 847353-30-4).

Exemplary protease inhibitors include, for example, aspartyl protease inhibitors, such as pepstatin and other pepsin inhibitors (e.g., sodium benzoate); and chymotrypsin and trypsin inhibitors. A wide variety of trypsin and chymotrypsin inhibitors are known to those skilled in the art and can be used in the methods described herein. Such trypsin and chymotrypsin inhibitors can include tissue-factor-pathway inhibitor; α-2 antiplasmin; serpin α-1 antichymotrypsin family members; gelin; hirustasin; eglins including eglin C; inhibitors from *Bombyx mori* (see; e.g.; JP 4013698 A2 and JP 04013697 A2; CA registry No. 142628-93-1); hirudin and variants thereof; secretory leukocyte protease inhibitor (SLPI); α-1 anti-trypsin; Bowman-Birk protease inhibitors (BBIs); chymotrypsin inhibitors represented by CAS registry Nos. 306762-66-3, 306762-67-4, 306762-68-5, 306762-69-6, 306762-70-9, 306762-71-0, 306762-72-1, 306762-73-2, 306762-74-3, 306762-75-4, 178330-92-2, 178330-93-3, 178330-94-4, 81459-62-3, 81459-79-2, 81460-01-7, 85476-59-1, 85476-62-6, 85476-63-7, 85476-67-1, 85476-70-6, 85858-66-8, 85858-68-0, 85858-69-1, 85858-70-4, 85858-71-5, 85858-72-6, 85858-73-7, 85858-75-9, 85858-77-1, 85858-79-3, 85858-81-7, 85858-83-9, 85858-84-0, 85858-85-1, 85858-87-3, 85858-89-5, 85858-90-8, 85858-92-0, 85879-03-4, 85879-05-6, 85879-06-7, 85879-08-9, 85858-74-8, 90186-24-6, 90185-93-6, 89703-10-6, 138320-33-9 (YS3025), 94149-41-4 (MR889), 85858-76-0, 89703-10-6, 90185-92-5, 90185-96-9, 90185-98-1, 90186-00-8, 90186-01-9, 90186-05-3, 90186-06-4, 90186-07-5, 90186-08-6, 90186-09-7, 90186-10-0, 90186-11-1, 90186-12-2, 90186-13-3, 90186-14-4, 90186-22-4, 90186-23-5, 90186-24-6, 90186-25-7, 90186-27-9, 90186-28-0, 90186-29-1, 90186-31-5, 90186-35-9, 90186-43-9, 90209-88-4, 90209-89-5, 90209-92-0, 90209-94-2, 90209-96-4, 90209-97-5, 90210-01-8, 90210-03-0, 90210-04-1, 90210-25-6, 90210-26-7, 90210-28-9, 90230-84-5, 90409-84-0, 95460-86-9, 95460-87-0, 95460-88-1, 95460-89-2, 95460-91-6, 114949-00-7, 114949-01-8, 114949-02-9, 114949-03-0, 114949-04-1, 114949-05-2, 114949-06-3, 114949-18-7, 114949-19-8, 114964-69-1, 114964-70-4, 9076-44-2 (chymostatin), 30827-99-7 (Pefabloc), 618-39-3 (benzamidine), 80449-31-6 (urinistatin), 130982-43-3, 197913-52-3, 179324-22-2, 274901-16-5, 792163-40-7, 339169-59-4, 243462-36-4, 654671-78-0, 55123-66-5 (leupeptin), 901-47-3, 4272-74-6, 51050-59-0, 221051-66-7, 80449-31-6, 55-91-4, 60-32-2, 88070-98-8, 87928-05-0, 402-71-1 (benzenesulfonamide), 139466-47-0, CI-2A (see U.S. Pat. No. 5,167,483), CI-2A (see WO9205239), WCI-3 (see Shibata et al. 1988 *J Biochem* (Tokyo) 104:537-43), WCI-2 (see Habu et al. 1992 J Biochem (Tokyo) 111:249-58), and WCI-x (Habu et al., supra) and 178330-95-5; and compounds with chymotrypsin inhibition activity described in patent publications JP 56092217 A2, U.S. Pat. No. 4,755,383, U.S. Pat. No. 4,755,383, U.S. Pat. No. 4,639,435, U.S. Pat. No. 4,620,005, U.S. Pat. No. 4,898,876, and EP0128007.

In a second aspect, pharmaceutical compositions for gastric retention of any of the compositions described herein are disclosed and provide sustained-release of the active agents. In certain embodiments, the pharmaceutical dosage form contains at least one bile acid sequestrant and a gastric-retention vehicle composition that contains one or more hydrogels such that the dosage form expands upon contact with gastric fluid.

In certain embodiments, the pharmaceutical dosage form is retained for a period of 6-24 hours (e.g., 6, 7, 8, 9, 10, 11, 12, 13, 14, 15, 16, 17, 18, 19, 20, 21, 22, 23, or 24 hours), or longer.

In certain embodiments, the active agent component can be in the form of a tablet and may additionally contain suitable diluents, glidants, lubricants, acidulants, stabilizers, swelling agents and other pharmaceutically acceptable excipients.

Exemplary hydrogels include, for example, hydroxypropyl methylcellulose, hydroxypropylcellulose, sodium carboxymethylcellulose, agar, agarose, locust bean gum, carageenan, alginic acid, konjac gum, guar gum, and xanthan gum.

In other embodiments, the gastric-retention vehicle composition can additionally include one or more of a superdisintegrant, a binder, and a gas-generating agent.

Exemplary superdisintegrants include, for example, crospovidone, croscarmellose sodium, and sodium starch glycolate.

Exemplary binders include, for example, poloxamers, polyethylene glycols, polyethylene glycol fatty acid esters, glyceryl palmitostearate, polyoxyethylene alkyl ethers, glyceryl behenate, stearoyl macrogol-32-glyceride, polyoxyethylene castor oil derivatives, polyoxyethylene sorbitan fatty acid derivatives, polyoxyethylene stearates, polyoxyethylene-polyoxypropylene copolymers, starches, gelatin, sugars such as lactose, sucrose, glucose and molasses, natural and synthetic gums such as acacia, sodium alginate, carboxymethylcellulose, methylcellulose, polyvinylpyrrolidone, ethyl cellulose and waxes.

Exemplary gas-generating agents include, for example, sodium hydrogen carbonate, sodium carbonate, potassium carbonate, calcium carbonate, magnesium carbonate, and sodium glycine carbonate.

In a third aspect, methods for treating or preventing an upper gastrointestinal tract disorder by administering to a patient in need thereof a composition containing a therapeutically effective amount of at least one bile acid sequestrant are disclosed.

In certain embodiments, the patient may be suffering from (or susceptible to developing) an upper GI tract disorder including, but not limited to, dyspepsia, heartburn, erosive esophagitis GERD, peptic ulcer, esophagitis, Barrett's Esophagus, and esophageal adenocarcinoma.

In other embodiments, the methods can include administering simultaneously, separately, or sequentially, a therapeutically effective amount of one or more proton pump inhibitors.

In still other embodiments, the methods can include administering simultaneously, separately, or sequentially one or more agents chosen from an antacid, a histamine $H_2$-receptor antagonist, a γ-aminobutyricacid-b (GABA-B) agonist, a prodrug of a GABA-B agonist, and a protease inhibitor.

In other embodiments, the composition is in a form suitable for oral administration.

In another aspect, methods for protecting stratified squamous epithelium against injury by a noxious substance by administering to an individual in need thereof a therapeutically effective amount of a composition comprising at least one bile acid sequestrant are disclosed.

In certain embodiments, the methods can include administering simultaneously, separately, or sequentially, a therapeutically effective amount of one or more proton pump inhibitors.

In other embodiments, the methods can include administering simultaneously, separately, or sequentially one or more agents chosen from an antacid, a histamine $H_2$-receptor antagonist, a γ-aminobutyricacid-b (GABA-B) agonist, a prodrug of a GABA-B agonist, and a protease inhibitor.

In yet another aspect, kits for treating an upper GI tract disorder comprising, in one or more containers, a therapeutically effective amount of the compositions as described in detail herein, and a label or packaging insert containing instructions for use are disclosed.

These, and other objects, features and advantages of this disclosure will become apparent from the following detailed description of the various aspects of the disclosure taken in conjunction with the accompanying Examples.

DETAILED DESCRIPTION

The present application discloses compositions containing at least one bile acid sequestrant, alone or in combination with other active agents, which are useful for treating or preventing a variety of upper gastrointestinal (GI) tract disorders and associated conditions.

The present application further discloses compositions including at least one proton pump inhibitor and at least one bile acid sequestrant which when administered to esophageal epithelial cell cultures, which are normally nonkeratinized, stratified squamous epithelium arranged in longitudinal folds, provide the benefit of inhibiting transformation into specialized columnar cells (indicating premalignancy) at a greater efficacy than either agent alone.

Accordingly, the compositions disclosed herein are useful in methods for treating or preventing a variety of upper gastrointestinal (GI) tract disorders and associated conditions such as, for example, gastroesophageal reflux disease (GERD) (including non-responsive GERD), heartburn, indigestion, dyspepsia, erosive esophagitis, peptic ulcer, gastric ulcer, NSAID-associated ulcers, duodenal ulcers, esophageal ulcers, esophagitis, laryngitis, ulcers arising from Meckel's diverticulum, Barrett's Esophagus, esophageal adenocarcinoma, and pharyngitis.

The present application includes compositions comprising therapeutically effective amounts of at least one bile acid sequestrant, or pharmaceutically acceptable salts thereof, formulated alone or in combination with a therapeutically effective amount of at least one proton pump inhibitor, or pharmaceutically acceptable salts thereof. In an embodiment, the compositions disclosed herein can also include, or be administered in combination (either simultaneously, separately, or sequentially) with, one or more commercially available antacids, histamine $H_2$-receptor antagonists, γ-aminobutyricacid-b (GABA-B) agonists, prodrugs of GABA-B agonists, and protease inhibitors.

In certain embodiments, any of the compositions disclosed herein can be provided as a sustained-release pharmaceutical dosage form that includes a therapeutically effective amount of one of the compositions described herein and a gastric-retention vehicle composition that contains one or more hydrogels, such that the dosage form expands upon contact with gastric fluid, thereby retaining the dosage form in the user's stomach for a longer period of time.

The present application also includes methods for treating or preventing an upper GI tract disorder by administering to a patient in need thereof a therapeutically effective amount of a pharmaceutical composition as disclosed and described in detail herein.

Similarly, the present application also includes methods for protecting stratified squamous epithelium against injury by a noxious substance by administering to a patient in need thereof a therapeutically effective amount of a pharmaceutical composition as disclosed and described in detail herein.

As employed above and throughout the disclosure, the following terms are provided to assist the reader. Unless otherwise defined, all terms of art, notations and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not necessarily be construed to represent a substantial difference over the definition of the term as generally understood in the art unless otherwise indicated.

As used herein, "treating" or "treatment of" a condition or subject refers to taking steps to obtain beneficial or desired results, including clinical results. For purposes of this disclosure, beneficial or desired clinical results include, but are not limited to, alleviation or amelioration of one or more disease, symptom, or condition related to lipid metabolism disorders, fatty liver disease, hepatitis, or erectile dysfunction.

As used herein, a "therapeutically effective amount" of a drug or pharmaceutical composition or formulation, or agent, described herein is an amount of a drug or agent that, when administered to a subject with a disease or condition, will have the intended therapeutic effect, e.g., alleviation, amelioration, palliation or elimination of one or more manifestations of the disease or condition in the subject. The full therapeutic effect does not necessarily occur by administration of one dose and may occur only after administration of a series of doses. Thus, a therapeutically effective amount may be administered in one or more administrations.

As used herein, a "prophylactically effective amount" of a drug or pharmaceutical composition or formulation, or agent, described herein is an amount of a drug or agent that, when administered to a subject, will have the intended prophylactic effect, e.g., preventing or delaying the onset (or reoccurrence) of disease or symptoms, or reducing the likelihood of the onset (or reoccurrence) of disease or symptoms. The full prophylactic effect does not necessarily occur by administration of one dose and may occur only after administration of a series of doses. Thus, a prophylactically effective amount may be administered in one or more administrations.

As used herein, and as would be understood by the person of skill in the art, the recitation of "a compound" or "a composition" is intended to include salts, solvates and inclusion complexes of that compound as well as any stereoisomeric form, or a mixture of any such forms of that compound in any ratio.

The term "pharmaceutically acceptable salt" refers to salts prepared from pharmaceutically acceptable non-toxic acids or bases including inorganic acids and bases and organic acids and bases. When the compounds of the present disclosure are basic, salts may be prepared from pharmaceutically acceptable non-toxic acids including inorganic and organic acids. Suitable pharmaceutically acceptable acid addition salts for the compounds of the present disclosure include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present disclosure include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

Administration of any of the compositions or formulations described in detail herein includes parallel administration (i.e., administration of elements of the formulation to the subject over a period-of time), co-administration or sequential administration (in which elements of the formulation are administered at approximately the same time, e.g., within about a few seconds to a few hours of one another), and simultaneous or co-formulation (in which elements of the formulation are combined or compounded into a single dosage form suitable for oral or parenteral administration).

Combination therapy can be achieved by administering two or more agents, e.g., a proton pump inhibitor and a bile acid sequestrant, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc.

A "subject" or "patient" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

A "susceptible individual" or "patient in need thereof" is an individual who suffers from, is suffering from, or is likely to or predisposed to suffer from an upper GI tract disorder. In humans these conditions may include, for example, gastroesophageal reflux disease (GERD), heartburn, indigestion, dyspepsia, erosive esophagitis, peptic ulcer, gastric ulcer, NSAID-associated ulcers, duodenal ulcers, esophageal ulcers, esophagitis, laryngitis, Meckel's diverticulum, Barrett's Esophagus, esophageal adenocarcinoma, or pharyngitis. In animals these conditions may include, for example, peptic ulcer of the forestomach.

As used herein "non-responsive GERD" refers to chronic reflux disorders that do not respond to current therapies used to treat such conditions. Such therapies include, for example, administration of proton pump inhibitors, $H_2$ blockers, and various antacids that are well known in the art.

A "noxious substance", as used herein, refers to a substance which causes injury to stratified squamous epithelium in vivo. Examples of such "noxious substances" include acids or other substances, including, but not limited to, gastric acid, HCl, N-acetylcysteine, pepsin, acid-pepsin, or other irritant which contacts epithelial tissue.

The terms "gastric fluid" and "gastric juice" are used interchangeably throughout and refer to the endogenous fluid medium of the stomach, including water and secretions. "Simulated gastric fluid" means any fluid that is generally recognized as providing a useful substitute for authentic gastric fluid in experiments designed to assess the chemical or biological behavior of substances in the stomach. One such simulated gastric fluid is aqueous 0.1 N HCl, pH 1.2. It will be understood that the term "gastric fluid" or "gastric juice" used throughout the disclosure and claims means authentic (i.e. endogenous) gastric fluid or simulated gastric fluid.

The term "gastro-retentive form" or "gastric retention vehicle" denotes dosage forms which effect sustained release of the active ingredient in comparison with conventional dosage forms, such as customary tablets or capsules, while avoiding an undesirably high initial dose, the release being effected continuously over a relatively long period and controlled at a therapeutically effective level by prolonged retention of the dosage form in the stomach.

This present disclosure provides, in various embodiments, pharmaceutical combination kits and oral drug dosage forms that contain at least one bile acid sequestrant alone or in combination with at least one proton pump inhibitor, optionally comprising one or more additional agents chosen from an antacid, a histamine $H_2$-receptor antagonist, a γ-aminobutyricacid-b (GABA-B) agonist, a prodrug of a GABA-B agonist, and a protease inhibitor. These agents may be contained in the same oral dosage form or in separate dosage forms that are administered sequentially or simultaneously.

The present disclosure also relates to a method for treating or preventing an upper gastrointestinal tract disorder, which is particularly useful as a first-line or initial therapy, comprising administering to a patient in need thereof a combination therapeutic regimen as described in the kits and dosage forms provided and discussed herein. "First-line" or "initial" treatment refers to treatment in the first instance after a new diagnosis of an upper gastrointestinal tract disorder, or after a relapse of an upper gastrointestinal tract disorder following cessation of treatment. However, the treatment method can be useful in any upper gastrointestinal tract disorder patient who is not responding to monotherapy with PPIs or bile acid sequestrants.

PPI drugs are substituted benzimidazole compounds that specifically inhibit gastric acid secretion by affecting the $H^+/K^+$ ATPase enzyme system (the proton pump). These drugs, for example esomeprazole, are rapidly absorbed and have very short half-lives. However, they exhibit prolonged binding to the $H^+/K^+$ ATPase enzyme. The anti-secretory effect reaches a maximum in about 4 days with once-daily dosing. Because of these characteristics, patients beginning PPI therapy do not receive maximum benefit of the drug and healing may not begin for up to 5 days after therapy begins when PPIs are used alone for initial therapy of upper GI tract disorders.

Proton pump inhibitors (PPIs) are potent inhibitors of gastric acid secretion, inhibiting $H^+/K^+$ ATPase, the enzyme involved in the final step of hydrogen ion production in the parietal cells. The term proton pump inhibitor includes, but is not limited to, omeprazole (as sold under the brand-names PRILOSEC®, LOSEC®, or ZEGERID®), lansoprazole (as sold under the brand-name PREVACID®, ZOTON®, or INHIBITOL®), rabeprazole (as sold under the brand-name RABECID®, ACIPHEX®, or PARIET®), pantoprazole (as sold under the brand-name PROTONIX®, PROTIUM®, SOMAC®, or PANTOLOC®), tenatoprazole (also referred to as benatoprazole), and leminoprazole, including isomers, enantiomers and tautomers thereof (e.g., esomeprazole (as sold under the brand-name NEXIUM®)), and alkaline salts thereof. The following patents describe various benzimidazole compounds suitable for use in the disclosure described herein: U.S. Pat. No. 4,045,563, U.S. Pat. No. 4,255,431, U.S. Pat. No. 4,359,465, U.S. Pat. No. 4,472,409, U.S. Pat. No. 4,508,905, JP-A-59181277, U.S. Pat. No. 4,628,098, U.S. Pat. No. 4,738,975, U.S. Pat. No. 5,045,321, U.S. Pat. No. 4,786,505, U.S. Pat. No. 4,853,230, U.S. Pat. No. 5,045,552, EP-A-295603, U.S. Pat. No. 5,312,824, EP-A-166287, U.S. Pat. No. 5,877,192, EP-A-519365, EP5129, EP 174,726, EP 166,287 and GB 2,163,747. All of the above patents are hereby incorporated herein by reference. Thus, proton pump inhibitors and their pharmaceutically acceptable salts, which are used in accordance with the present disclosure, are known compounds and can be produced by known processes. In certain embodiments, the proton pump inhibitor is omeprazole, either in racemic mixture or only the (−)enantiomer of omeprazole (i.e. esomeprazole), as set forth in U.S. Pat. No. 5,877,192, hereby incorporated by reference.

Omeprazole is typically administered in a 20 mg dose/day for active duodenal ulcer for 4-8 weeks; in a 20 mg dose/day for gastro-esophageal reflux disease (GERD) or severe erosive esophagitis for 4-8 weeks; in a 20 mg dose/twice a day for treatment of *Helicobacter pylori* (in combination with other agents); in a 60 mg dose/day for active duodenal ulcer for 4-8 weeks and up to 120 mg three times/day, and in a 40 mg dose/day for gastric ulcer for 4-8 weeks. Such dosages are contemplated to be within the scope of the present disclosure. Thus, in certain embodiments of the present disclosure, the amount of proton pump inhibitor which is included in the dosage form is an amount which is considered to be therapeutically effective, in accordance with the dosages set forth above for a variety of disease states. In other embodiments of the present disclosure, the dose of proton pump inhibitor is sub-therapeutic. For example, when the drug is omeprazole, the dosage form may contain from about 0.1 mg to about 120 mg omeprazole.

Lansoprazole is typically administered about 15-30 mg/day; rabeprazole is typically administered 20 mg/day and pantoprazole is typically administered 40 mg/day. However, any therapeutic or sub-therapeutic dose of these agents is considered within the scope of the present disclosure.

In certain embodiments, the proton pump inhibitor(s) included in the dosage forms of the present disclosure are protected from contact with acidic gastric juice, and transferred without exposure to gastric fluid until the dosage form reaches a part of the gastrointestinal tract where the pH is near neutral and where rapid absorption of omeprazole can occur.

Bile acids are steroid acids found predominantly in the bile of mammals. They are produced in the liver by the oxidation of cholesterol, and are stored in gallbladder and secreted into the intestine in the form of salts. They act as surfactants, emulsifying lipids and assisting with the absorption and digestion of dietary fat and cholesterol.

Synthesis of bile acids is a major consumer of cholesterol. The body synthesizes about 800 mg of cholesterol per day and about half of that is used for bile acid synthesis. In total about 20-30 grams of bile acids are secreted into the intestine daily; about 90% of excreted bile acids are reabsorbed (by active transport in the ileum) and recycled. This is referred to as the enterohepatic circulation.

Since bile acids are made from endogenous cholesterol, the enterohepatic circulation of bile acids may be disrupted as a way to lower cholesterol. This is the usual therapeutic rationale for administering bile acid sequestrants.

The principal bile acids are: Cholic acid, Chenodeoxycholic acid, Deoxycholic acid, Taurocholic acid, and Glycocholic acid. The chemical distinctions between different bile acids are minute, depending only on the presence or absence of hydroxyl groups on positions 3, 7, and 12. In humans, the most important bile acids are cholic acid and chenodeoxycholic acid, and their conjugates with taurine and glycine (glycocholate and taurocholate). Some mammals synthesize predominantly deoxycholic acid.

As surfactants or detergents, bile acids are potentially toxic to cells and their levels are tightly regulated. They function directly as signaling molecules in the liver and the intestines by activating a nuclear hormone receptor known as FXR and also NR1H4. This results in inhibition of bile acid synthesis in the liver when bile acid levels are too high. Emerging evidence associates FXR activation with alterations in triglyceride metabolism, glucose metabolism and liver growth.

Bile acid sequestrants bind bile acids in the small intestine and carry them out of the body. This causes the body to use more cholesterol to make more bile acids, which are secreted into the small intestine, bound to bile acid sequestrants, and carried out of the body. The end result is lower cholesterol levels. Bile acid sequestrants also prevent absorption of some dietary cholesterol.

Bile acid sequestrants currently approved for human use are polymeric compounds which serve as ion exchange resins. Bile acid sequestrants exchange anions such as chloride ions for bile acids. By doing so, they bind bile acids and sequester them from enterohepatic circulation. Since bile acid sequestrants are large polymeric structures, they are not well-absorbed from the gut into the bloodstream. Thus, bile acid sequestrants, along with any bile acids bound to the drug, are excreted via the feces after passage through the gastrointestinal tract. Exemplary bile acid sequestrants include, for example, cholestyramine (as sold under the brand-name QUESTRAN®), colesevelam (as sold under the brand-name WELCHOL®), and colestipol (as sold under the brand-name COLESTID®), and pharmaceutically acceptable salts thereof.

The present disclosure is also directed to a dosage form that provides for the release of at least one bile acid sequestrant to reduce bile acid reflux symptoms in a patient, as well as for the release of both at least one bile acid sequestrant and at least one proton pump inhibitor to reduce both bile acid reflux and gastric acid reflux symptoms in a patient. The dosage form can be prepared such that the active ingredients are for quick release or delayed release, or quick release of one active ingredient and delayed release of the other active ingredient.

The compositions comprising the active agents disclosed herein may also be formulated to include, or administered in conjunction with, other agents for treating the gastrointestinal tract, such as histamine $H_2$ receptor blockers, motility agents (gastroprokinetics), antacids, antiulcerative agents, γ-aminobutyricacid-b (GABA-B) agonists, prodrugs of GABA-B agonists, and/or protease inhibitors. Nonlimiting examples of these additional agents include those selected from the group consisting of cinitapride, cisapride, fedotozine, loxiglumide, alexitol sodium, almagate, aluminum hydroxide, aluminum magnesium silicate, aluminum phosphate, azulene, basic aluminum carbonate gel, bismuth aluminate, bismuth phosphate, bismuth subgallate, bismuth subnitrate, calcium carbonate, dihydroxyaluminum aminoacetate, dihydroxyaluminum sodium carbonate, ebimar, magaldrate, magnesium carbonate hydroxide, magnesium hydroxide, magnesium oxide, magnesium peroxide, magnesium phosphate (tribasic), magnesium silicates, potassium citrate, sodium bicarbonate, aceglutamide aluminum complex, acetoxolone, aldioxa, arbaprostil, benexate hydrochloride, carbenoxolone, cetraxate, cimetidine, colloidal bismuth subcitrate, ebrotidine, ecabet, enprostil, esaprazole, famotidine, gefamate, guaiazulene, irsogladine, misoprostol, nizatidine, omoprostil, γ-Oryzanol, pifamine, pirenzepine, plaunotol, polaprezinc, ranitidine, rebamipide, rioprostil, rosaprostol, rotraxate, roxatidine acetate, sofalcone, spizofarone, sucralfate, telenzepine, teprenone, trimoprostil, trithiozine, troxipide, zolimidine, baclofen, R-baclofen, XP19986 (CAS Registry No. 847353-30-4), pepstatin and other pepsin inhibitors (e.g., sodium benzoate); and chymotrypsin and trypsin inhibitors. A wide variety of trypsin and chymotrypsin inhibitors are known to those skilled in the art and can be used in the methods described herein. Such trypsin and chymotrypsin inhibitors can include tissue-factor-pathway inhibitor; α-2 antiplasmin; serpin α-1 antichymotrypsin family members; gelin; hirustasin; eglins including eglin C; inhibitors from *Bombyx mori* (see; e.g.; JP 4013698 A2 and JP 04013697 A2; CA registry No. 142628-93-1); hirudin and variants thereof; secretory leukocyte protease inhibitor (SLPI); α-1 antitrypsin; Bowman-Birk protease inhibitors (BBIs); chymotrypsin inhibitors represented by CAS registry Nos. 306762-66-3, 306762-67-4, 306762-68-5, 306762-69-6, 306762-70-9, 306762-71-0, 306762-72-1, 306762-73-2, 306762-74-3, 306762-75-4, 178330-92-2, 178330-93-3, 178330-94-4, 81459-62-3, 81459-79-2, 81460-01-7, 85476-59-1, 85476-62-6, 85476-63-7, 85476-67-1, 85476-70-6, 85858-66-8, 85858-68-0, 85858-69-1, 85858-70-4, 85858-71-5, 85858-72-6, 85858-73-7, 85858-75-9, 85858-77-1, 85858-79-3, 85858-81-7, 85858-83-9, 85858-84-0, 85858-85-1, 85858-87-3, 85858-89-5, 85858-90-8, 85858-92-0, 85879-03-4, 85879-05-6, 85879-06-7, 85879-08-9, 85858-74-8, 90186-24-6, 90185-93-6, 89703-10-6, 138320-33-9 (YS3025), 94149-41-4 (MR889), 85858-76-0, 89703-10-6, 90185-92-5, 90185-96-9, 90185-98-1, 90186-00-8, 90186-01-9, 90186-05-3, 90186-06-4, 90186-07-5, 90186-08-6, 90186-09-7, 90186-10-0, 90186-11-1, 90186-12-2, 90186-13-3, 90186-14-4, 90186-22-4, 90186-23-5, 90186-24-6, 90186-25-7, 90186-27-9, 90186-28-0, 90186-29-1, 90186-31-5, 90186-35-9, 90186-43-9, 90209-88-4, 90209-89-5, 90209-92-0, 90209-94-2, 90209-96-4, 90209-97-5, 90210-01-8, 90210-03-0, 90210-04-1, 90210-25-6, 90210-26-7, 90210-28-9, 90230-84-5, 90409-84-0, 95460-86-9, 95460-87-0, 95460-88-1, 95460-89-2, 95460-91-6, 114949-00-7, 114949-01-8, 114949-02-9, 114949-03-0, 114949-04-1, 114949-05-2, 114949-06-3, 114949-18-7, 114949-19-8, 114964-69-1, 114964-70-4, 9076-44-2 (chymostatin), 30827-99-7 (Pefabloc), 618-39-3 (benzamidine), 80449-31-6 (urinistatin), 130982-43-3, 197913-52-3, 179324-22-2, 274901-16-5, 792163-40-7, 339169-59-4, 243462-36-4, 654671-78-0, 55123-66-5 (leupeptin), 901-47-3, 4272-74-6, 51050-59-0, 221051-66-7, 80449-31-6, 55-91-4, 60-32-2, 88070-98-8, 87928-05-0, 402-71-1 (benzenesulfonamide), 139466-47-0, CI-2A (see U.S. Pat. No. 5,167,483), CI-2A (see WO9205239), WCI-3 (see Shibata et al. 1988 *J Biochem* (Tokyo) 104:537-43), WCI-2 (see Habu et al. 1992 J Biochem (Tokyo) 111:249-58), and WCI-x (Habu et al., supra) and 178330-95-5; and compounds with chymotrypsin inhibition activity described in patent publications JP 56092217 A2, U.S. Pat. No. 4,755,383, U.S. Pat. No. 4,755,383, U.S. Pat. No. 4,639,435, U.S. Pat. No. 4,620,005, U.S. Pat. No. 4,898,876, and EP0128007.

The active ingredients used in tablets, i.e., bile acid sequestrants alone or in combination with proton pump inhibitors, are well known in the art and many are commercially available. If desired, drugs can also be manufactured using methodology well known in the art.

Formulation and Administration

Making of Pharmaceutical Preparations: The active agents used in the compositions of the present disclosure will typically be formulated in accordance with methods that are standard in the art (see e.g., Remington: the Science and Practice of Pharmacy 19th Ed. 1995 Mack Publishing Co. Easton Pa.). Drugs may be prepared in admixture with conventional excipients, carriers, buffers, flavoring agents, etc.

Typical carriers include, but are not limited to: water; salt solutions; alcohols; gum arabic; vegetable oils; benzyl alcohols; polyethylene glycols; gelatin; carbohydrates, such as lactose, amylose or starch; magnesium stearate; talc; silicic acid; paraffin; perfume oil; fatty acid esters; hydroxymethylcellulose; polyvinyl pyrrolidone; etc. Pharmaceutical preparations can be sterilized and, if desired, mixed with auxiliary agents such as: lubricants; preservatives; disintegrants; stabilizers such as cyclodextrans; wetting agents; emulsifiers; salts; buffers; natural or artificial coloring agents; natural or artificial flavoring agents; or aromatic substances. Pharmaceutical preparations can also include one or more of the following: acetylated monoglyceride, aspartame, beta carotene, calcium stearate, carnauba wax, cellulose acetate phthalate, citric acid, citric acid anhydrous, colloidal silicon dioxide, confectioner's sugar, crospovidone, docusate sodium, ethyl alcohol, ferric oxide, fructose, gelatin, glycerine, glyceryl monostearate (e.g. glyceryl monostearate 40-50), glyceryl triacetate, HPMC (hydroxypropyl methylcellulose), hydroxypropyl cellulose, hypromellose, iron oxide, isopropyl alcohol, lactose monohydrate, low substituted hydroxypropyl cellulose, magnesium carbonate, magnesium stearate, maltol, mannitol, methacrylic acid, methacrylic acid copolymer (e.g. methacrylic acid copolymer type C), methylcellulose, microcrystalline cellulose, mono ammonium glycyrrhizinate, n-butyl alcohol, paraffin, pectin propylene glycol alginate, polyacrylate, polyethylene glycol (e.g. polyethylene glycol 6000), polysorbate 80, polyvinyl pyrrolidone, povidone, propylene glycol, shellac, silicon dioxide, sodium carbonate, sodium citrate, sodium hydroxide, sodium lauryl sulfate, sodium stearyl fumarate, sorbitol, starch, sucrose, sugar sphere, talc, titanium dioxide, triethyl citrate, and xanthan gum. In certain embodiments, buffers that can raise the pH of the stomach are used. For example bicarbonate buffers may be included in the outer coating or as a rapidly dissolving, separate layer immediately below the outer coating.

The enteric coating surrounding the core may be applied using standard coating techniques. Materials used to form the enteric coating may be dissolved or dispersed in organic or aqueous solvents and may include one or more of the following: methacrylic acid copolymers; shellac; hydroxypropylmethylcellulose phthalate; polyvinyl acetate phthalate; hydroxypropylmethylcellulose trimellitate; carboxymethylcellulose; cellulose acetate phthalate; or other suitable enteric coating polymers. The pH at which the enteric coat will dissolve can be controlled by the polymer or combination of polymers selected and/or ratio of pendant groups. For example, dissolution characteristics of the coating can be altered by the ratio of free carboxyl groups to ester groups. Enteric coating layers may also contain pharmaceutical plasticizers such as: triethyl citrate; dibutyl phthalate; triacetin; polyethylene glycols; polysorbates; etc. Additives such as dispersants, colorants, anti-adhering and anti-foaming agents may also be included.

Making of Tablet Dosage Forms: Tablets can be made using standard technology well known in the art. Drugs used in the core or the outer coating may be granulated by methods such as slugging, low-shear or high-shear granulation, wet granulation, or fluidized bed granulation. Outer coatings may be formed by preparing a mixture containing appropriate polymers and a sufficient amount of drug to produce a therapeutically effective dose. The solution may then be sprayed on preformed, enterically-coated cores to produce the final tablets. If desired, a buffer layer or layer containing other agents may be interspersed between the enterically coated core and the outer coating.

In certain embodiments a pharmaceutical composition is prepared by adding a pharmaceutically acceptable carrier to the aforementioned compound, a pharmaceutically acceptable salt thereof, or a hydrate thereof as an active ingredient of the medicament of the present disclosure. As the medicament of the present disclosure, a substance, per se, that is selected from the group consisting of the alkylenedioxybenzene derivative and a pharmaceutically acceptable salt thereof, and a hydrate thereof and a solvate thereof may be administered to a mammal including human. In certain embodiments, pharmaceutical compositions comprising one or more of the aforementioned substances as an active ingredient and one or more of pharmaceutical additives are administered to a patient.

A variety of administration routes can be used in accordance with the present disclosure. An effective amount of the peptide described herein can be administered parenterally, orally, by inhalation, nasally, buccally, or via an implanted reservoir.

Examples of the pharmaceutical composition include formulations for oral administration such as tablets, capsules, subtilized granules, powders, pills, troches, sublingual tablets and liquid preparations, and formulations for parenteral administration such as injections, suppositories, ointments, patches and the like.

In certain embodiments, formulations including those which slowly release the agent over time, such as found in lozenges, gums, and buccal patches are used. In other embodiments, formulations including agents in a bioadherent ingestible composition, such as those found in U.S. Pat. Nos. 5,858,391 and 5,670,163 to Cuca, et al. are used. The agent may also be formulated as a liquid or as a tablet, pill, capsule or powder to be dissolved in a liquid, and is preferably slowly sipped by the patient.

The protective agents disclosed herein and compositions comprising the agents may be administered by perfusion via a tube on to the surface of stratified squamous epithelia, by oral ingestion, gum or lozenge (for treatment of oropharyngeal, rumen, forestomach and esophageal epithelium), by mouth rinse (for oropharyngeal, tongue and buccal epithelium), by aerosol spray (for oropharyngeal, buccal, tongue, laryngeal or vocal cord epithelium), or by other means.

Certain embodiments encompass where the agent provides protection against damage by a noxious substance to the epithelium after a short period of contact with the epithelium. In certain embodiments the period of contact can be, for example, less than or equal to 1 hour, less than or equal to 30 minutes, less than or equal to 15 minutes, less than or equal to 10 minutes, less than or equal to 5 minutes, less than or equal to 1 minute. In a preferred embodiment the epithelium is contacted with or exposed to the agent for about 1 to 5 minutes.

Tablets and capsules for oral administration are usually provided in a unit dosage form, and can be prepared by adding ordinary pharmaceutical carriers such as binders, fillers, diluents, compressing agents, lubricants, disintegrating agents, coloring matters, flavoring agents, and moistening agents. Tablets may be coated according to a well known method, for example, by using an enteric coating agent. For example, fillers such as cellulose, mannitol and lactose; disintegrating agents such as starch, polyvinylpyrrolidone, starch derivatives and sodium starchglycolate; lubricants such as magnesium stearate; moistening agents such as sodium laurylsulfate and the like may be used.

Liquid preparations for oral administration can be provided in the forms of, for example, aqueous or oily suspensions, solutions, emulsions, syrups and elixirs, as well as dried formulations that is re-dissolvable before use by water or a suitable medium. Those liquid preparations may contain ordinary additives, for example, suspending agents such as sorbitol, syrups, methylcellulose, gelatin, hydroxyethylcellulose, carboxymethylcellulose, aluminum stearate gel and hydrogenated edible fats; emulsifiers such as lecitin, sorbitan monooleate and gum arabic; non-aqueous media including edible oils such as almond oil, rectified coconut oil, oily esters (e.g., esters of glycerin), propylene glycol and ethyl alcohol; preservatives such as methyl ester, ethyl ester and propyl ester of p-hydroxybenzoic acid and sorbic acid; and usual flavoring agents and coloring matters as required.

Formulations for oral administration can be manufactured according to a method well known in the art, for example, by mixing, filling, compressing and the like. In addition, it is also possible to disperse the active ingredient in a formulation containing a large amount of filler by repetitive mixing. Formulations for parenteral administration are generally provided as unit dosage form preparations containing the compound as the active ingredient and a sterilized medium. The solution for parenteral administration may generally be prepared by dissolving the compound in a medium, subjecting the resulting solution to filtration for sterilization, filling the solution in vials or ampoules, and sealing the vials or ampoules. It is also possible to freeze the composition and fill the result in vials, and then eliminate the moisture in vacuo to improve stability. Parenteral suspensions can be prepared by substantially the same method as that applied to solutions for parenteral administration; however, the suspensions can preferably be manufactured by suspending the active ingredient in a medium, and then subjecting the result to sterilization by using ethylene oxide or the like. Furthermore, surface active agents, moistening agents and so forth may also be added so that a uniform dispersion of the active ingredient can be obtained.

Combining two or more active ingredients in single dosage form results in the possibility of chemical interactions between the active drug substances. For example, acidic and basic active ingredients can react with each other and acidic active ingredients can facilitate the degradation of acid labile substances. Thus, in certain dosage forms, acidic and basic substances can be physically separated as two distinct or isolated layers in a compressed tablet, or in the core and shell of a press-coated tablet. Additional agents that are compatible with acidic as well as basic substances, have the flexibility of being placed in either layer. In certain multiple layer compositions at least one active ingredient can be enteric-coated. In certain embodiments thereof at least one active ingredient can be presented in a controlled release form. In certain embodiments where a combination of three or more active substances are used, they can be presented as physically isolated segments of a compressed multilayer tablet, which can be optionally film coated.

The therapeutic combinations described herein can be formulated as a tablet or capsule comprising a plurality of beads, granules, or pellets. All active ingredients including the vitamins of the combination are formulated into granules or beads or pellets that are further coated with a protective coat, an enteric coat, or a film coat to avoid the possible chemical interactions. Granulation and coating of granules or beads is done using techniques well known to a person skilled in the art. At least one active ingredient can present in a controlled release form. Finally these coated granules or beads are filled into hard gelatin capsules or compressed to form tablets.

The therapeutic combinations described herein can be formulated as a capsule comprising microtablets or minitablets of all active ingredients. Microtablets of the individual agents can be prepared using well known pharmaceutical procedures of tablet making like direct compression, dry granulation or wet granulation. Individual microtablets can be filled into hard gelatin capsules. A final dosage form may comprise one or more microtablets of each individual component. The microtablets may be film coated or enteric coated.

The therapeutic combinations described herein can be formulated as a capsule comprising one or more microtablets and powder, or one or more microtablets and granules or beads. In order to avoid interactions between drugs, some active ingredients of a said combination can be formulated as microtablets and the others filled into capsules as a powder, granules, or beads. The microtablets may be film coated or enteric coated. At least one active ingredient can be presented in controlled release form.

The therapeutic combinations described herein can be formulated wherein the active ingredients are distributed in the inner and outer phase of tablets. In an attempt to divide chemically incompatible components of proposed combination, few interacting components are converted in granules or beads using well known pharmaceutical procedures in prior art. The prepared granules or beads (inner phase) are then mixed with outer phase comprising the remaining active ingredients and at least one pharmaceutically acceptable excipient. The mixture thus comprising inner and outer phase is compressed into tablets or molded into tablets. The granules or beads can be controlled release or immediate release beads or granules, and can further be coated using an enteric polymer in an aqueous or non-aqueous system, using methods and materials that are known in the art.

The therapeutic combinations described herein can be formulated as single dosage unit comprising suitable buffering agent. All powdered ingredients of said combination are mixed and a suitable quantity of one or more buffering agents is added to the blend to minimize possible interactions.

The agents described herein, alone or in combination, can be combined with any pharmaceutically acceptable carrier or medium. Thus, they can be combined with materials that do not produce an adverse, allergic or otherwise unwanted reaction when administered to a patient. The carriers or mediums used can include solvents, dispersants, coatings, absorption promoting agents, controlled release agents, and one or more inert excipients (which include starches, polyols, granulating agents, microcrystalline cellulose, diluents, lubricants, binders, disintegrating agents, and the like), etc. If desired, tablet dosages of the disclosed compositions may be coated by standard aqueous or nonaqueous techniques. The agents described herein, alone or in combination, can be formulated using Nanocrystal® technology (Elan Corporation, Dublin, Ireland).

The agents can be a free acid or base, or a pharmacologically acceptable salt thereof. Solids can be dissolved or dispersed immediately prior to administration or earlier. In some circumstances the preparations include a preservative to prevent the growth of microorganisms. The pharmaceutical forms suitable for injection can include sterile aqueous or organic solutions or dispersions which include, e.g., water, an alcohol, an organic solvent, an oil or other solvent or dispersant (e.g., glycerol, propylene glycol, polyethylene glycol, and vegetable oils). The formulations may contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Pharmaceutical agents can be sterilized by filter sterilization or by other suitable means.

Suitable pharmaceutical compositions in accordance with the invention will generally include an amount of the active compound(s) with an acceptable pharmaceutical diluent or excipient, such as a sterile aqueous solution, to give a range of final concentrations, depending on the intended use. The techniques of preparation are generally well known in the art, as exemplified by Remington's Pharmaceutical Sciences, 19th Ed., Mack Publishing Company, 1995.

The agent can be in the form of a pharmaceutically acceptable salt. Such salts are prepared from pharmaceutically acceptable non-toxic bases including inorganic bases and organic bases. Examples of salts derived from inorganic bases include aluminum, ammonium, calcium, copper, ferric, ferrous, lithium, magnesium, manganic salts, manganous, potassium, sodium, zinc, and the like. In some embodiments, the salt can be an ammonium, calcium, magnesium, potassium, or sodium salt. Examples of salts derived from pharmaceutically acceptable organic non-toxic bases include salts of primary, secondary, and tertiary amines, benethamine, N,N'-dibenzylethylenediamine, diethylamine, 2-diethylaminoethanol, 2-dimethylaminoethanol, diethanolamine, ethanolamine, ethylenediamine, N-ethylmorpholine, N-ethylpiperidine, epolamine, glucamine, glucosamine, histidine, hydrabamine, isopropylamine, lysine, methylglucamine, meglumine, morpholine, piperazine, piperidine, polyamine resins, procaine, purines, theobromine, triethylamine, trimethylamine, tripropylamine, and trolamine, tromethamine Examples of other salts include tris, arecoline, arginine, barium, betaine, bismuth, chloroprocaine, choline, clemizole, deanol, imidazole, and morpholineethanol.

The agents of the invention can be administered orally, e.g., as a tablet or cachet containing a predetermined amount of the active ingredient, pellet, gel, paste, syrup, bolus, electuary, slurry, capsule; powder; granules; as a solution or a suspension in an aqueous liquid or a non-aqueous liquid; as an oil-in-water liquid emulsion or a water-in-oil liquid emulsion, via a liposomal formulation (see, e.g., EP736299) or in some other form. Orally administered compositions can include binders, lubricants, inert diluents, lubricating, surface active or dispersing agents, flavoring agents, and humectants. Orally administered formulations such as tablets may optionally be coated or scored and may be formulated so as to provide sustained, delayed or controlled release of the active ingredient therein.

Gastric-Retention Vehicles

A traditional oral sustained-release formulation releases most of the drug at the colon. Thus, clinically acceptable sustained release dosage forms prepared with conventional technology may not be successful where a particular drug has an absorption window in a particular region of the gastrointestinal tract, such as the duodenum and upper jejunem segments. In such cases, a gastroretentive drug delivery system can be employed to help retain the active ingredient in the stomach, thereby assisting in and improving the sustained delivery of the drug.

Several approaches are currently used to prolong gastric retention time. These include floating drug delivery systems, also known as hydrodynamically balanced systems, swelling and expanding systems, polymeric bioadhesive systems, modified-shape systems, high-density systems, and other delayed gastric emptying systems. For example, Dave et al. AAPS Pharm Sci Tech 2004; 5(2), 1-6, report on a gastroretentive drug delivery system of ranitidine hydrochloride using the principles of buoyant preparation, wherein guar gum, xanthan gum, and hydroxypropyl methylcellulose were evaluated for gel-forming properties, sodium bicarbonate was used as a gas-generating agent, and the effects of citric acid and stearic acid on drug release profile and floating properties were investigated. Similarly, Narendra et al. AAPS Pharm Sci Tech 2006, 7(2), E1-7, reports on the development of an optimized gastric floating drug delivery system containing metoprolol tartrate as a model drug, wherein the dosage form was prepared as a bilayer tablet comprising a drug-loading layer and a floating layer in a suitable ratio to provide a bulk density lower than that of gastric fluids to remain buoyant on the stomach contents.

Other variations of gastric-retention vehicle compositions are known to those skilled in the art and are suitable for use with the compositions and methods described in detail and disclosed herein. For example, in certain embodiments, the present invention provides methods of making a gastro-retentive dosage form of any of the compositions described herein, wherein said method comprises (a) forming a tablet comprising any composition described herein, a binder and a pharmaceutically-acceptable gas-generating agent, (b) surrounding the tablet with an expandable, hydrophilic, water-permeable and substantially gas-impermeable, membrane, and (c) sealing the membrane to retard the escape of gas from within the sealed membrane. A further optional step comprises (d) encapsulating the membrane-sealed tablet within a covering that disintegrates without delay upon contact with gastric fluid.

Active

The active ingredient in the gastro-retentive dosage forms of the present invention includes any of the compositions described in detail and disclosed herein in an amount as contemplated and described below.

The tablet component contains the active ingredient (e.g., at least one bile acid sequestrant, alone or in combination with at least one proton pump inhibitor and/or optionally one or more other agents) in a therapeutically effective amount. Typically, the active ingredient(s) is present in an amount from between 10% to about 50% of the total tablet weight, preferably between about 15% and about 40%. Other therapeutically effective dosages can be readily determined by one of skill in the pharmaceutical or medical arts.

Binder

The tablet component of the gastro-retentive dosage form comprises the active ingredient (for example, at least one bile acid sequestrant or combinations of at least one bile acid sequestrant and at least one proton pump inhibitor), a gas-generating agent and a binder. Binders (also called wetting agents) are agents used to improve the cohesiveness of the tablet formulation, ensuring that the tablet will remain intact after formation. Suitable binders for use in the gastric-retention vehicle for use with the present invention include but are not limited to poloxamers, polyethylene glycols (e.g., PEG 3350), polyethylene glycol fatty acid esters (e.g., Myrj), glyceryl palmitostearate (e.g. Precirol AT05), polyoxyethylene alkyl ethers, glyceryl behenate (e.g., Compritol 888), stearoyl macrogol-32-glyceride (e.g., Gelucire), polyoxyethylene castor oil derivatives, polyoxyethylene sorbitan fatty acid derivatives, polyoxyethylene stearates, polyoxyethylene-polyoxypropylene copolymers (e.g. Lutrol or Pluronics), starches, gelatin, sugars such as lactose, sucrose, glucose and molasses, natural and synthetic gums such as acacia, sodium alginate, carboxymethylcellulose, methylcellulose, polyvinylpyrrolidone, ethyl cellulose and waxes. Suitable binders also include Myrj52 (particularly Myrj52P or Myrj52FL), Lutrol F68, Compritol 888, Gelucire 50/13, PEG 3350, Precirol ATOS methylcellulose and polyvinyl pyrrolidone.

The binder is present in the tablet component in an amount effective to provide cohesion to the final tablet form. The appropriate amount of binder can be readily determined by one of ordinary skill in the pharmaceutical arts and will depend, inter alia, upon the particular binder used and the method of preparation of the tablet. The binder may be present in the tablet in an amount from between about 8% to about 15% of the total tablet weight.

Gas-Generating Agent

A gas-generating agent may be included in the tablet component to generate the carbon dioxide gas that results in the expansion of the membrane component upon contact with gastric juice. Suitable gas-generating agents are, for example, solids that liberate this gas itself, for example under the action of body fluid or the hydrogen ions present therein. Such gas-generating agents are, for example, those capable of releasing carbon dioxide and include, but are not limited to, pharmaceutically acceptable mono- and di-basic salts of carbonic acid, for example alkali metal hydrogen carbonates or alkali metal carbonates, alkaline earth metal carbonates or ammonium carbonate.

Such mono- or di-basic salts of carbonic acid are especially sodium hydrogen carbonate (sodium bicarbonate) or sodium carbonate, potassium carbonate, calcium carbonate, magnesium carbonate, sodium glycine carbonate, or mixtures thereof. In order to increase the evolution of carbon dioxide, there may be added to the mentioned carbonates the acid component customarily used in effervescent mixtures, for example sodium dihydrogen phosphate or disodium hydrogen phosphate, sodium tartrate, sodium ascorbate or sodium citrate. Also suitable are yeasts which are likewise capable of generating carbon dioxide gas. When yeasts, for example baker's yeast, are used, the necessary nutrients, for example glucose, are added to the formulation. In certain embodiments, the gas-generating agent will be sodium hydrogen carbonate.

The gas-generating agent may be present in the tablet component in an amount between about 30% and about 82% of the total tablet weight. In certain embodiments, the gas-generating agent is present at about 40% to about 82% of the total tablet weight.

Other Agents

In addition to the active ingredient, the binder and the gas-generating agent, the tablet component may also include one or more of diluents, glidants, lubricants, acidulants, swelling agents, surfactants and other pharmaceutically acceptable excipients. A diluent is a substance added to increase the bulk of a mixture to make a tablet a practical size for granulation, compression or molding when only a small amount of active is present. Suitable diluents include lactose, cellulose, dry starch, powdered sugar, dicalcium phosphate, calcium sulfate, sodium chloride, kaolin, mannitol, sorbitol, sucrose, inositol. In certain embodiments, the diluent is lactose, sorbitol, mannitol, cellulose or starch. A glidant (or flow-enhancing agent) is a substance that improves the flow characteristics of a powder mixture. Commonly used glidants include colloidal silicon dioxide, magnesium trisilicate, powdered cellulose, starch, tribasic calcium phosphate and talc. Glidants useful in this invention include these commonly used glidants. In certain embodiments, the glidant is Aerosil 200, colloidal silicon dioxide. A lubricant is a substance that has a number of functions in the preparation of the tablet component of this invention, including preventing the adhesion of the tablet material to the surface of the dies and punches, reducing interparticle friction, facilitating the ejection of the tablet from the die cavity and in some instances, improving the rate of flow of the tablet granulation. Commonly used lubricants include talc, magnesium stearate, calcium stearate, zinc stearate, stearic acid, glyceryl monostearate, glyceryl palmitostearate, hydrogenated vegetable oils, hydrogenated castor oil, light mineral oil, sodium benzoate, sodium stearyl fumarate and polyethylene glycol (PEG). Any of the commonly used lubricants are suitable for use in the present invention. In one embodiment, magnesium stearate is used as a lubricant. An acidulant may be added to increase the release of carbon dioxide from this sodium hydrogen carbonate. Commonly used acidulants include citric acid, fumaric acid, malic acid and tartaric acid. It will be apparent from the foregoing that a single substance may serve more than one of the purposes described above.

Swelling Agents

In addition to the afore-mentioned gas-generating agents, it is also possible for intensifying the action of the agent to use pharmaceutically acceptable hydrophilic swelling agents, for example partially etherified cellulose derivatives, starches, water-soluble, aliphatic or cyclic poly-N-vinylamides, polyvinyl alcohols, polyacrylates, polymethacrylates, polyethylene glycols or mixtures of these auxiliaries. In certain embodiments, the hydrophilic swelling agent may also serve as a binder.

Hydrophilic, partially etherified cellulose derivatives are, for example, lower alkyl ethers of cellulose having an average degree of molar substitution (MS) of more than 1 and less than 3 and an average degree of polymerisation of approximately 100-5000.

The degree of substitution is a measure of the substitution of the hydroxy groups by lower alkoxy groups per glucose unit. The average degree of molar substitution (MS) is a mean value and indicates the number of lower alkoxy groups per glucose unit in the polymer.

The average degree of polymerisation (DP) is likewise a mean value and indicates the average number of glucose units in the cellulose polymer.

Lower alkyl ethers of cellulose are, for example, cellulose derivatives that are substituted at the hydroxymethyl group (primary hydroxy group) of the glucose unit forming the cellulose chains and optionally at the second and third secondary hydroxy group by $C_1$-$C_4$ alkyl groups, especially methyl or ethyl, or by substituted $C_1$-$C_4$ alkyl groups, for example 2-hydroxyethyl, 3-hydroxy-n-propyl, carboxymethyl or 2-carboxyethyl.

Suitable lower alkyl ethers of cellulose include methylcellulose, ethylcellulose, methylhydroxyethylcellulose, methylhydroxypropylcellulose, ethylhydroxyethylcellulose, hydroxyethylcellulose, hydroxypropylcellulose, carboxymethylcellulose (in salt form, for example sodium salt form) or methylcarboxymethylcellulose (likewise in salt form, for example sodium salt form).

A starch suitable for use as hydrophilic swelling agent is, for example, a mixture of approximately 15-20% amylose (molar mass approximately 50,000 to 200,000) and 80-85% amylopectin (molar mass approximately 100,000 to 1,000,000), for example rice, wheat or potato starch, and also starch derivatives, such as partially synthetic amylopectin, for example sodium carboxymethylamylopectin, and alginates of the alginic acid type.

Water-soluble, aliphatic or cyclic poly-N-vinylamides include, for example, poly-N-vinyl-methylacetamide, poly-N-vinylethylacetamide, poly-N-vinylmethylpropionamide, poly-N-vinylethylpropionamide, poly-N-vinylmethylisobutyramide, poly-N-vinyl-2-pyrrolidone, poly-N-vinyl-2-piperidone, poly-N-vinyl-.epsilon.-caprolactam, poly-N-vinyl-5-methyl-2-pyrrolidone or poly-N-vinyl-3-methyl-2-pyrrolidon-e, especially poly-N-vinylpyrrolidone having a mean molar mass of approximately 10,000-360,000, for example the polyvinylpyrrolidone obtainable under the trade mark Kollidon® (BASF).

Suitable polyvinyl alcohols have a mean molar mass of approximately 15,000 to 250,000 and a degree of hydrolysis of approximately 70-99%. In certain embodiments, the polyvinyl alcohols have a degree of hydrolysis of approximately 70-88% (partially hydrolysed polyvinyl alcohol), for example the polyvinyl alcohol obtainable under the trade name Mowiol® (Hoechst) denoted by MOWIOL 3-83, 4-80, 4-88, 5-88 or 8-88.

Hydrophilic polyacrylates that can be used as swelling agents have a mean molecular weight of approximately $8.6 \times 10^5$ to $1.0 \times 10^6$. The polyacrylic acid chains carry a greater or smaller number of short side chains and so the individual commercial forms differ in this respect, as well as in having different molecular weights. In some embodiments, neutralised (for example with dilute aqueous sodium hydroxide solution) polyacrylic acid derivatives of the commercial form Carbopol® (Goodrich), for example CARBOPOL 934 P or CARBOPOL 940, are used.

Suitable polymethacrylates are likewise swellable and have a mean molecular weight of more than $1.0 \times 10^6$. Commercial forms that can be used include the polymers of methacrylic acid and methacrylic acid esters of the Eudragit® type, for example EUDRA-GIT L or EUDRAGIT S (Rohm GmbH).

Suitable polyethylene glycols have an average molecular weight of approximately 4000 to 6000. Pharmaceutical-quality commercial forms are preferred, for example polyethylene glycol such as Lutrol® (BASF), Polydiol®, Polywachs® (Huls), Polyglykol®, Lanogen® (Hoechst), Carbowax® (Union Carbide), Plurocol® (Wyandotte) or Tetronic® (Kuhlmann).

Suitable hydrophilic swelling agents are also homopolymers, such as polyhydroxyalkyl methacrylate having a molecular weight from 5,000 to 5,000,000 anionic or cationic hydrogels, mixtures of agar and carboxymethylcellulose, swellable agents consisting of methylcellulose in admixture with weakly cross-linked agar, or water-swellable polymers that can be produced by dispersion of a finely particulate copolymer of maleic acid anhydride and styrene, or tragacanth, gelatine or swellable ion exchange resins.

Swellable ion exchangers are, for example, copolymer resins having acidic groups, for example, sulfonic acid groups or salt forms thereof based on styrenedivinylbenzene. Such copolymer resins consist of cross-linked styrene polymers which are obtained by copolymerization of styrene with divinylbenzene as cross-linking agent. Customary derivisation reactions, for example sulfonation reactions, are used to incorporate acidic groups, such as sulfo groups, into the structure. The preparation and the properties of these resins are known. Reference is made to the article in Ullmanns Enzyklopdie der Technischen Chemie, 4th Edition, Vol. 13, pp. 279 ff., and to Kirk-Othmer, Encyclopaedia of Chemical Technology, J. Wiley, Vol. 13, pp. 678 ff., and to the numerous literature references cited therein.

Preferred ion exchange resins are those having quaternary ammonium groups or sulfonic acid groups based on styrenedivinylbenzene which are commercially available and are acceptable for use in pharmaceutical formulations, for example resins marketed by the firm Rohm and Haas under the trade mark Amberlite® IRP-69.

Surfactants

The tablet component can also contain the customary pharmaceutical formulation adjuncts that are used at present for the manufacture of oral dosage forms, such as tablets, for example surface-active substances, for example so-called surfactants, for example anionic surfactants of the alkyl sulfate type, for example sodium, potassium or magnesium n-dodecyl sulfate, n-tetradecyl sulfate, n-hexadecyl sulfate or n-octadecyl sulfate, alkyl ether sulfate, for example sodium, potassium or magnesium n-dodecyloxyethyl sulfate, n-tetradecyloxyethyl sulfate, n-hexadecyloxyethyl sulfate or n-octadecyloxyethyl sulfate, or alkanesulfonate, for example sodium, potassium or magnesium n-dodecanesulfonate, n-tetradecanesulfonate, n-hexadecanesulfonate or n-octadecanesulfonate.

Suitable surfactants are also nonionic surfactants of the fatty acid/polyhydroxy alcohol ester type, such as orbitan monolaurate, monooleate, monostearate or monopalmitate, sorbitan tristearate or trioleate, polyoxyethylene adducts of fatty acid/polyhydroxy alcohol esters, such as polyoxyethylene sorbitan monolaurate, monooleate, monostearate, monopalmitate, tristearate or trioleate, polyethylene glycol/fatty acid esters, such as polyoxyethylene stearate, polyethylene glycol 400 stearate or polyethylene glycol 2000 stearate, especially ethylene oxide/propylene oxide block copolymers of the Pluronics® (BWC) or Synperonic® (ICI) type, myristates and their condensation products, or ethylene oxide homopolymers having a degree of polymerisation of approximately 2,000 to 100,000, which are known, for example, under the trade name Polyox® (Union Carbide).

Expandable Membrane

The hydrophilic membrane, which is expandable at the site of use and is permeable to body fluid, consists of a plastic or wax-like, pharmaceutically acceptable polymeric material that is substantially gas-impermeable to the gas generated by the gas-generating agent. By "substantially gas-impermeable" is meant that the flow of gas through the membrane is impeded sufficiently to allow expansion of the membrane sachet or pouch upon the generation of gas from the gas-generating agent contained in the tablet component for a suitable period of time. Because of its hydrophilic properties, the membrane can absorb body fluid, such as gastric fluid, and can effect retarded and continuous release of controlled amounts of the active ingredients contained in the tablet component by means of diffusion or optionally by the use of osmosis.

Suitable plastic or wax-like polymeric materials for the expandable hydrophilic membrane include for example hydrophilic foils, for example foils of cellulose ethers, such as methyl- or ethyl-cellulose, hydroxypropylcellulose, methyl- or ethyl-hydroxyethylcellulose, methyl- or ethyl-hydroxypropylcellulose carboxymethylcellulose, polyvinyl alcohol, polyvinyl acetate, polyvinylpyrrolidone, polyacrylonitrile, mixtures of polyvinylpyrrolidone with polyvinyl alcohol, resins based on phthalic acid anhydride/polyhydroxy alcohol, urethanes, polyamides, shellac, etc.

In certain embodiments, polyvinyl alcohols having a degree of hydrolysis of more than 92% (fully hydrolysed polyvinyl alcohol), especially more than 97%, for example MOWIOL of the 98 series, for example MOWIOL 4-98, 10-98, 20-98, 28-99, 56-98 and 66-100, PVAU228-08 are used. In other embodiments, MOWIOL 28-99 and PVAU228-08 are utilized.

To these materials it is possible to add further adjuncts, for example plasticisers, which improve the elasticity of the membrane, for example glycerol, polyethylene glycol/fatty acid esters, such as polyethylene glycol 400 stearate or polyethylene glycol 2000 stearate, triethyl citrate, diethyl phthalate, diethyl sebacate, and the like. The amount of plasticiser added is approximately from 0.01 to 60% by weight, based on the total weight of the dosage form. Glycerol at 10-30% w/w may be used as the plasticizer, for example, at 20%.

In one embodiment, the expandable membrane is produced by preparing a homogeneous mixture of polyvinyl alcohol and additives, such as plasticisers, for example glycerol and/or polyethylene glycol 400 stearate, by dissolution in water, which is optionally heated, and evaporation to form layers of suitable thickness, for example 100 mm, or by allowing a solution of polyvinyl alcohol in water (without additives) to evaporate. The film or the foil which is obtainable after evaporation of an aqueous solution of polyvinyl alcohol, especially polyvinyl alcohol having a degree of hydrolysis of more than 97%, and polyethylene glycol/fatty acid ester, for example polyethylene glycol 400 stearate or polyethylene glycol 2000 stearate, optionally with the addition of plasticisers, such as glycerol, is distinguished by a high degree of extensibility. A film-like residue which can be obtained after evaporation of an aqueous solution containing approximately 40-85% polyvinyl alcohol, 0-40% polyethylene glycol stearate and 10-30% glycerol has particularly advantageous properties. This film is distinguished by particularly good extensibility. This film can be easily cut and formed into pouches or sachets to accommodate individual tablet components or used as a sheet to fold around the tablet component or several sheets of membrane film can be used to sandwich the tablet components.

Optional Covering

In certain embodiments, the gastro-retentive vehicle for use in accordance with the invention can be provided with a covering which surrounds or contains the tablet component and the membrane component and which disintegrates without delay under the action of body fluid at the site of use and which consists of a film coating or, preferably, a covering in capsule form.

Suitable film coatings delay the release of active ingredient only slightly or not at all. Water-soluble film coatings from approximately 20 µm to approximately 150 µm in thickness are preferred. Suitable film coating materials are especially hydrophilic cellulose derivatives, such as cellulose ethers, for example methylcellulose, hydroxypropylcellulose or especially hydroxypropylmethylcellulose, mixtures of polyvinylpyrrolidone or of a copolymer of polyvinylpyrrolidone and polyvinyl acetate with hydroxypropylmethylcellul-ose, mixtures of shellac with hydroxypropylmethylcellulose, polyvinyl acetate or copolymers thereof with polyvinylpyrrolidone, or mixtures of water-soluble cellulose derivatives, such as hydroxypropylmethylcellulose-, and water-insoluble ethylcellulose. These coating agents can, if desired, be used in admixture with other adjuncts, such as talc, wetting agents, for example polysorbates (for example to facilitate application), or pigments (for example for identification purposes). Depending upon the solubility of the components, these coatings are applied in aqueous solution or in organic solution (for example solutions of shellac or ethylcellulose in organic solvents). It is also possible to use mixtures of acrylates that are water-insoluble per se, for example the copolymer of ethyl acrylate and methyl methacrylate, which are used in aqueous dispersion, with water-soluble adjuncts, for example lactose, polyvinylpyrrolidone, polyethylene glycol or hydroxypropylmethylcellulose-.

Instead of using a film-like coating, the gastro-retentive vehicles for use in accordance with the invention can be provided with a covering in capsule form. Hard gelatin capsules having high watersolubility and/or swellability are preferred. Size 000, Size 00 and Size 0 dry-fill capsules such as by Capsugel are preferred, in order to accommodate the membrane enclosed tablets.

When present, the covering is preferably a dry-fill capsule, more preferably a hard gelatin dry-fill capsule.

Preparation of the Gastro-Retentive Vehicles

In an aspect, the present invention provides a method of making a gastro-retentive dosage form of the compositions described in detail and disclosed herein, which method comprises: forming a tablet comprising any of the compositions disclosed herein, a binder and a pharmaceutically-acceptable gas-generating agent, surrounding the tablet with an expandable, hydrophilic, water-permeable and substantially gas-impermeable membrane, and sealing the membrane to retard the escape of gas from within the sealed membrane. Optionally, the method comprises the additional step of encapsulating the sealed membrane within a covering that disintegrates without delay upon contact with gastric fluid.

As described above, the tablet component can be formed using any convenient tabletting method. Such methods are well known in the art and are described, for example, in Remington: the Science and Practice of Pharmacy 19th Ed. 1995 Mack Publishing Co. Easton Pa.

In one embodiment of the gastro-retentive dosage form of the present invention, the tablet component will be surrounded by the expandable membrane component. The membrane surrounds the tablet on all sides and is sealed to retard the escape of gas generated by the gas-generating agent contained in the tablet. This surrounding can be accomplished in various ways. The membrane may be a preformed sachet or pouch that contains an opening large enough for insertion of the tablet component. After insertion of the tablet, the opening is sealed by appropriate means, for example heat and/or pressure. Alternatively, the membrane may be formed around the tablet, for example as a coating on the tablet that completely surrounds the tablet, or may be formed by sandwiching the tablet component between two or more separate layers of membrane material, or one membrane layer folded over the tablet, and sealing the membrane layers together around the tablet by heat and/or pressure. Typically, the membrane pouch surrounding the tablet component will be as small as possible consistent with the need to accommodate the tablet component and provide for sufficient expansion of the dosage form in the stomach.

As mentioned, the hydrophilic membrane is typically prepared in the form of a sachet or pouch into which the tablet component can be inserted. Such a pouch or sachet is readily prepared from the membrane film prepared as described herein. After insertion of the tablet, the pouch can be sealed around the tablet to retard the escape of gas generated by the gas-generating agent in the tablet component. The sachet or pouch can be any convenient shape, typically will be rectangular or circular. Typically, the uninflated membrane sachet or pouch is about 20-25 mm in the longest dimension and may be shorter, depending on the size of the tablet component that must be accommodated. In some embodiments, the membrane film will not be preformed into pouches but will be used as a film layer to surround the tablet component, either by sandwiching the tablet between two (or more) membrane layers or by folding a single layer over the tablet. The membrane layers will be sealed on all sides surrounding the tablet and cut along the seal to produce the dosage form. Multiple dosage forms may be produced simultaneously in this way by using a membrane layer large enough to accommodate multiple tablets, sealing the membrane layers between the tablets and cutting at the sealed membrane to produce the dosage forms.

It is also possible for the tablet component to be surrounded not by one but by several coverings of expansible permeable material. With such a multi-layered arrangement, it is also possible for a formulation of the compositions disclosed herein, or constituents of the formulation, for example the gas-generating agent, such as sodium hydrogen carbonate, to be located between the individual layers. With a multi-layered arrangement it is possible to achieve an even longer dwell time of the dosage form at the site of action, for example in the stomach. In addition, the expansible membrane (b) may itself, contain physiologically active substances.

In a one form of the process, the expandable membrane surrounding tablet component is produced first, for example by preparing a homogeneous mixture of polyvinyl alcohol and additives, such as plasticisers, for example glycerol and/or polyethylene glycol 400 stearate, by dissolution in water, which is optionally heated, and evaporation to form layers of suitable thickness, for example 100 mm, or by allowing a solution of polyvinyl alcohol in water (without additives) to evaporate. The layers are cut into strips of a suitable size and the active ingredient formulation consisting of the tablet component is applied. This can be effected for example, by filling the still open sachet, which is then closed completely, for example by sealing, for example with heat and/or pressure. The sealed sachets can then be filled into dry-fill capsules.

The gastro-retentive dosage form according to the invention can be of various shapes and may be, for example, round, oval, oblong, tubular and so on, and may be of various sizes depending upon the size and shape of the tablet component. In addition, the dosage form may be transparent, colourless or coloured in order to impart to the product an individual appearance and the ability to be immediately recognised.

In some embodiments, the gastro-retentive dosage form can be prepared using microparticulates or nanoparticulates comprising the active (i.e., bile acid sequestrant or bile acid sequestrant:proton pump inhibitor combinations) in lieu of a tablet. The microparticulates or nanoparticulates will comprise the active ingredient, a binder and a gas-generating agent, optionally other agents as described herein, and other optional components as described for the tablets. The microparticulates or nanoparticulates are prepared using, for example, the granulation techniques described herein or other well known methods for preparing microparticulates and nanoparticulates.

Other gastro-retentive forms and methods of making and using the same are known to those skilled in the art and are also suitable for use in accordance with the compositions described in detail and disclosed herein, and include, for example, any of those described and disclosed in U.S. Pat. Nos. 4,996,058; 6,881,420; 6,776,999; 6,723,340; 6,685,962; 6,548,083; 5,972,389; 4,851,232; 4,735,804 and U.S. Published Application Nos. 20070269512; 20070196396; 20070190140; 20060013876; 20050202090; 20040180086; 20030104053; and 20030021845, each of which are incorporated herein by reference in its entirety.

Dosing and Regimen

Doses of the aforementioned compound as the active ingredient can be suitably decided depending on the purpose of administration, i.e., therapeutic or preventive treatment, nature of a disease to be treated or prevented, conditions, body weight, age, sexuality and the like of a patient. In the method for administering the pharmaceutical preparation according to the present disclosure, the proton pump inhibitor and/or other optional agent may be administered simultaneously with the bile acid sequestrant or the agent(s) may be sequentially administered in an optional order. The practically desirable method and sequence for administration varies depending on the purpose of administration, i.e., therapeutic or preventive treatment, nature of a disease to be treated or prevented, conditions, body weight, age, sexuality and the like of a patient. The optimum method and sequence for administration of the compounds described in detail herein under preset given conditions may be suitably selected by those skilled in the art with the aid of the routine technique and the information contained in the present specification.

Typically, an amount of about 2 g to 24 g of a bile acid sequestrant per day for an adult may be administered orally. Alternatively, an amount of about 10 mg to 80 mg of a proton pump inhibitor and about 2 g to 24 g of a bile acid sequestrant per day for an adult may be administered orally. Such doses may be desirably administered once a day to several times a day as divided portions. For example, the compositions of the present disclosure may be administered at least 1×, 2×, 3×, 4×, 5×, 6×, 8×, 10× or 20×. A preferred embodiment includes where the composition described herein is administered at least once a day for a period of days, weeks, months or years. The agent may be administered at least once, twice, three, or four times daily. Depending upon the desired therapeutic action, patient response and other factors, the dosage form may be administered between meals, during meals, prior to a meal (i.e., within 5, 10, 15, 20, 25, 30, 35, 40, 45, 50, 55, or 60 minutes, 2 hours, 4 hours, 8 hours, or 12 hours prior to eating) or after a meal (i.e., within 5, 10, 15, 20, 25, 30, 35, 40, 45, 50, 55, or 60 minutes, 2 hours, 4, hours, 8 hours, or 12 hours following a meal).

A dosage unit (e.g. an oral dosage unit) can include from, for example, at least about or less than about 1 g to at least about or less than about 30 g (e.g. at least about or less than about 1 g, at least about or less than about 2 g, at least about or less than about 3 g, at least about or less than about 4 g, at least about or less than about 5 g, at least about or less than about 6 g, at least about or less than about 7 g, at least about or less than about 8 g, at least about or less than about 9 g, at least about or less than about 10 g, at least about or less than about 11 g, at least about or less than about 12 g, at least about or less than about 13 g, at least about or less than about 14 g, at least about or less than about 15 g, at least about or less than about 16 g, at least about or less than about 17 g, at least about or less than about 18 g, at least about or less than about 19 g, at least about or less than about 20 g, at least about or less than about 21 g, at least about or less than about 22 g, at least about or less than about 23 g, at least about or less than about 24 g, at least about or less than about 25 g, at least about or less than about 26 g, at least about or less than about 27 g, at least about or less than about 28 g, at least about or less than about 29 g, at least about or less than about 30 g) of a bile acid sequestrant (e.g., cholestyramine, colesevelam, colesevelam-HCl, ursodeoxycholic acid). A dosage unit (e.g. an oral dosage unit) can include from, for example, at least about or less than about 1 to at least about or less than about 200 mg, at least about or less than about 5 mg to at least about or less than about 100 mg, at least about or less than about 10 to at least about or less than about 120 mg, at least about or less than about 20 to at least about or less than about 100 mg, at least about or less than about 40 mg to at least about or less than about 100 mg, at least about or less than about 5 to at least about or less than about 80 mg, at least about or less than about 10 to at least about or less than about 40 mg, at least about or less than about 10 mg to at least about or less than about 60 mg, at least about or less than about 1 mg, at least about or less than about 2 mg, at least about or less than about 3 mg, at least about or less than about 4 mg, at least about or less than about 5 mg, at least about or less than about 10 mg, at least about or less than about 15 mg, at least about or less than about 20 mg, at least about or less than about 25 mg, at least about or less than about 30 mg, at least about or less than about, at least about or less than about 35 mg, at least about or less than about 40 mg, at least about or less than about 45 mg, at least about or less than about 50 mg, at least about or less than about 55 mg, at least about or less than about 60 mg, at least about or less than about 65 mg, at least about or less than about 70 mg, at least about or less than about 75 mg, at least about or less than about 80 mg, at least about or less than about 85 mg, at least about or less than about 90 mg, at least about or less than about 95 mg, at least about or less than about 100 mg, at least about or less than about 105 mg, at least about or less than about 110 mg, at least about or less than about 115 mg, at least about or less than about 120 mg of a proton pump inhibitor (e.g. omeprazole, esomeprazole, lansoprazole, pantoprazole, rabeprazole, tenatoprazole, leminoprazole, dontoprazole, and ransoprazole) and from at least about or less than about 1 g to at least about or less than about 30 g (e.g. at least about or less than about 1 g, at least about or less than about 2 g, at least about or less than about 3 g, at least about or less than about 4 g, at least about or less than about 5 g, at least about or less than about 6 g, at least about or less than about 7 g, at least about or less than about 8 g, at least about or less than about 9 g, at least about or less than about 10 g, at least about or less than about 11 g, at least about or less than about 12 g, at least about or less than about 13 g, at least about or less than about 14 g, at least about or less than about 15 g, at least about or less than about 16 g, at least about or less than about 17 g, at least about or less than about 18 g, at least about or less than about 19 g, at least about or less than about 20 g, at least about or less than about 21 g, at least about or less than about 22 g, at least about or less than about 23 g, at least about or less than about 24 g, at least about or less than about 25 g, at least about or less than about 26 g, at least about or less than about 27 g, at least about or less than about 28 g, at least about or less than about 29 g, at least about or less than about 30 g) of a bile acid sequestrant (e.g., cholestyramine, colesevelam, colesevelam-HCl, ursodeoxycholic acid). A dosage unit (e.g. an oral dosage unit) can include from, for example, at least about or less than about 0.2 g to at least about or less than about 6 g (e.g. at least about or less than about 0.2 g, at least about or less than about 0.4 g, at least about or less than about 0.6 g, at least about or less than about 0.8 g, at least about or less than about 1 g, at least about or less than about 1.2 g, at least about or less than about 1.4 g, at least about or less than about 1.6 g, at least about or less than about 1.8 g, at least about or less than about 2 g, at least about or less than about 2.2 g, at least about or less than about 2.4 g, at least about or less than about 2.6 g, at least about or less than about 2.8 g, at least about or less than about 3 g, at least about or less than about 3.2 g, at least about or less than about 3.4 g, at least about or less than about 3.6 g, at least about or less than about 3.8 g, at least about or less than about 4 g, at least about or less than about 4.2 g, at least about or less than about 4.4 g, at least about or less than about 4.6 g, at least about or less than about 4.8 g, at least about or less than about 5 g, at least about or less than about 5.2 g, at least about or less than about 5.4 g, at least about or less than about 5.6 g, at least about or less than about 5.8 g, at least about or less than about 6 g) of a bile acid sequestrant (e.g., cholestyramine, colesevelam, colesevelam-HCl, ursodeoxycholic acid). A dosage unit (e.g. an oral dosage unit) can include from, for example, at least about or less than about 1 to at least about or less than about 200 mg, at least about or less than about 5 mg to at least about or less than about 100 mg, at least about or less than about 10 to at least about or less than about 120 mg, at least about or less than about 20 to at least about or less than about 100 mg, at least about or less than about 40 mg to at least about or less than about 100 mg, at least about or less than about 5 to at least about or less than about 80 mg, at least about or less than about 10 to at least about or less than about 40 mg, at least about or less than about 10 mg to at least about or less than about 60 mg, at least about or less than about 1 mg, at least about or less than about 2 mg, at least about or less than about 3 mg, at least about or less than about 4 mg, at least about or less than about 5 mg, at least about or less than about 10 mg, at least about or less than about 15 mg, at least about or less than about 20 mg, at least about or less than about 25 mg, at least about or less than about 30 mg, at least about or less than about 35 mg, at least about or less than about 35 mg, at least about or less than about 40 mg, at least about or less than about 45 mg, at least about or less than about 50 mg, at least about or less than about 55 mg, at least about or less than about 60 mg, at least about or less than about 65 mg, at least about or less than about 70 mg, at least about or less than about 75 mg, at least about or less than about 80 mg, at least about or less than about 85 mg, at least about or less than about 90 mg, at least about or less than about 95 mg, at least about or less than about 100 mg, at least about or less than about 105 mg, at least about or less than about 110 mg, at least about or less than about 115 mg, at least about or less than about 120 mg of a proton pump inhibitor (e.g. omeprazole, esomeprazole, lansoprazole, pantoprazole, rabeprazole, tenatoprazole, leminoprazole, dontoprazole, and ransoprazole) and from at least about or less than about 0.2 g to at least about or less than about 6 g (e.g. at least about or less than about 0.2 g, at least about or less than about 0.4 g, at least about or less than about 0.6 g, at least about or less than about 0.8 g, at least about or less than about 1 g, at least about or less than about 1.2 g, at least about or less than about 1.4 g, at least about or less than about 1.6 g, at least about or less than about 1.8 g, at least about or less than about 2 g, at least about or less than about 2.2 g, at least about or less than about 2.4 g, at least about or less than about 2.6 g, at least about or less than about 2.8 g, at least about or less than about 3 g, at least about or less than about 3.2 g, at least about or less than about 3.4 g, at least about or less than about 3.6 g, at least about or less than about 3.8 g, at least about or less than about 4 g, at least about or less than about 4.2 g, at least about or less than about 4.4 g, at least about or less than about 4.6 g, at least about or less than about 4.8 g, at least about or less than about 5 g, at least about or less than about 5.2 g, at least about or less than about 5.4 g, at least about or less than about 5.6 g, at least about or less than about 5.8 g, at least about or less than about 6 g) of a bile acid sequestrant (e.g., cholestyramine, colesevelam, colesevelam-HCl, ursodeoxycholic acid).

A dosage unit (e.g. an oral dosage unit) can include from, for example, from at least about or less than about 0.1 g to at least about or less than about 3 g (e.g. at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, at least about or less than about 3 g) of a bile acid sequestrant (e.g., cholestyramine, colesevelam, colesevelam-HCl, ursodeoxycholic acid). A dosage unit (e.g. an oral dosage unit) can include from, for example, at least about or less than about 1 to at least about or less than about 200 mg, at least about or less than about 5 mg to at least about or less than about 100 mg, at least about or less than about 10 to at least about or less than about 120 mg, at least about or less than about 20 to at least about or less than about 100 mg, at least about or less than about 40 mg to at least about or less than about 100 mg, at least about or less than about 5 to at least about or less than about 80 mg, at least about or less than about 10 to at least about or less than about 40 mg, at least about or less than about 10 mg to at least about or less than about 60 mg, at least about or less than about 1 mg, at least about or less than about 2 mg, at least about or less than about 3 mg, at least about or less than about 4 mg, at least about or less than about 5 mg, at least about or less than about 10 mg, at least about or less than about 15 mg, at least about or less than about 20 mg, at least about or less than about 25 mg, at least about or less than about 30 mg, at least about or less than about 35 mg, at least about or less than about 35 mg, at least about or less than about 40 mg, at least about or less than about 45 mg, at least about or less than about 50 mg, at least about or less than about 55 mg, at least about or less than about 60 mg, at least about or less than about 65 mg, at least about or less than about 70 mg, at least about or less than about 75 mg, at least about or less than about 80 mg, at least about or less than about 85 mg, at least about or less than about 90 mg, at least about or less than about 95 mg, at least about or less than about 100 mg, at least about or less than about 105 mg, at least about or less than about 110 mg, at least about or less than about 115 mg, at least about or less than about 120 mg of a proton pump inhibitor (e.g. omeprazole, esomeprazole, lansoprazole, pantoprazole, rabeprazole, tenatoprazole, leminoprazole, dontoprazole, and ransoprazole) and from at least about or less than about 0.1 g to at least about or less than about 3 g (e.g. at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, at least about or less than about 3 g) of a bile acid sequestrant (e.g., cholestyramine, colesevelam, colesevelam-HCl, ursodeoxycholic acid).

A dosage unit (e.g. an oral dosage unit) can include from, for example, from at least about or less than about 0.02 g to at least about or less than about 0.6 g (e.g. at least about or less than about 0.02 g, at least about or less than about 0.04 g, at least about or less than about 0.06 g, at least about or less than about 0.08 g, at least about or less than about 0.1 g, at least about or less than about 0.12 g, at least about or less than about 0.14 g, at least about or less than about 0.16 g, at least about or less than about 0.18 g, at least about or less than about 0.2 g, at least about or less than about 0.22 g, at least about or less than about 0.24 g, at least about or less than about 0.26 g, at least about or less than about 0.28 g, at least about or less than about 0.3 g, at least about or less than about 0.32 g, at least about or less than about 0.34 g, at least about or less than about 0.36 g, at least about or less than about 0.38 g, at least about or less than about 0.4 g, at least about or less than about 0.42 g, at least about or less than about 0.44 g, at least about or less than about 0.46 g, at least about or less than about 0.48 g, at least about or less than about 0.5 g, at least about or less than about 0.52 g, at least about or less than about 0.54 g, at least about or less than about 0.56 g, at least about or less than about 0.58 g, at least about or less than about 0.6 g) of a bile acid sequestrant (e.g., cholestyramine, colesevelam, colesevelam-HCl, ursodeoxycholic acid). A dosage unit (e.g. an oral dosage unit) can include from, for example, at least about or less than about 1 to at least about or less than about 200 mg, at least about or less than about 5 mg to at least about or less than about 100 mg, at least about or less than about 10 to at least about or less than about 120 mg, at least about or less than about 20 to at least about or less than about 100 mg, at least about or less than about 40 mg to at least about or less than about 100 mg, at least about or less than about 5 to at least about or less than about 80 mg, at least about or less than about 10 to at least about or less than about 40 mg, at least about or less than about 10 mg to at least about or less than about 60 mg, at least about or less than about 1 mg, at least about or less than about 2 mg, at least about or less than about 3 mg, at least about or less than about 4 mg, at least about or less than about 5 mg, at least about or less than about 10 mg, at least about or less than about 15 mg, at least about or less than about 20 mg, at least about or less than about 25 mg, at least about or less than about 30 mg, at least about or less than about 35 mg, at least about or less than about 35 mg, at least about or less than about 40 mg, at least about or less than about 45 mg, at least about or less than about 50 mg, at least about or less than about 55 mg, at least about or less than about 60 mg, at least about or less than about 65 mg, at least about or less than about 70 mg, at least about or less than about 75 mg, at least about or less than about 80 mg, at least about or less than about 85 mg, at least about or less than about 90 mg, at least about or less than about 95 mg, at least about or less than about 100 mg, at least about or less than about 105 mg, at least about or less than about 110 mg, at least about or less than about 115 mg, at least about or less than about 120 mg of a proton pump inhibitor (e.g. omeprazole, esomeprazole, lansoprazole, pantoprazole, rabeprazole, tenatoprazole, leminoprazole, dontoprazole, and ransoprazole) and from at least about or less than about 0.02 g to at least about or less than about 0.6 g (e.g. at least about or less than about 0.02 g, at least about or less than about 0.04 g, at least about or less than about 0.06 g, at least about or less than about 0.08 g, at least about or less than about 0.1 g, at least about or less than about 0.12 g, at least about or less than about 0.14 g, at least about or less than about 0.16 g, at least about or less than about 0.18 g, at least about or less than about 0.2 g, at least about or less than about 0.22 g, at least about or less than about 0.24 g, at least about or less than about 0.26 g, at least about or less than about 0.28 g, at least about or less than about 0.3 g, at least about or less than about 0.32 g, at least about or less than about 0.34 g, at least about or less than about 0.36 g, at least about or less than about 0.38 g, at least about or less than about 0.4 g, at least about or less than about 0.42 g, at least about or less than about 0.44 g, at least about or less than about 0.46 g, at least about or less than about 0.48 g, at least about or less than about 0.5 g, at least about or less than about 0.52 g, at least about or less than about 0.54 g, at least about or less than about 0.56 g, at least about or less than about 0.58 g, at least about or less than about 0.6 g) of a bile acid sequestrant (e.g., cholestyramine, colesevelam, colesevelam-HCl, ursodeoxycholic acid).

A dosage unit (e.g. an oral dosage unit) can include from, for example, from at least about or less than about 0.01 g to at least about or less than about 0.3 g (e.g. at least about or less than about 0.01 g, at least about or less than about 0.02 g, at least about or less than about 0.03 g, at least about or less than about 0.04 g, at least about or less than about 0.05 g, at least about or less than about 0.06 g, at least about or less than about 0.07 g, at least about or less than about 0.08 g, at least about or less than about 0.09 g, at least about or less than about 0.1 g, at least about or less than about 0.11 g, at least about or less than about 0.12 g, at least about or less than about 0.13 g, at least about or less than about 0.14 g, at least about or less than about 0.15 g, at least about or less than about 0.16 g, at least about or less than about 0.17 g, at least about or less than about 0.18 g, at least about or less than about 0.19 g, at least about or less than about 0.2 g, at least about or less than about 0.21 g, at least about or less than about 0.22 g, at least about or less than about 0.23 g, at least about or less than about 0.24 g, at least about or less than about 0.25 g, at least about or less than about 0.26 g, at least about or less than about 0.27 g, at least about or less than about 0.28 g, at least about or less than about 0.29 g, at least about or less than about 0.3 g) of a bile acid sequestrant (e.g., cholestyramine, colesevelam, colesevelam-HCl, ursodeoxycholic acid, sevelamer). A dosage unit (e.g. an oral dosage unit) can include from, for example, at least about or less than about 1 to at least about or less than about 200 mg, at least about or less than about 5 mg to at least about or less than about 100 mg, at least about or less than about 10 to at least about or less than about 120 mg, at least about or less than about 20 to at least about or less than about 100 mg, at least about or less than about 40 mg to at least about or less than about 100 mg, at least about or less than about 5 to at least about or less than about 80 mg, at least about or less than about 10 to at least about or less than about 40 mg, at least about or less than about 10 mg to at least about or less than about 60 mg, at least about or less than about 1 mg, at least about or less than about 2 mg, at least about or less than about 3 mg, at least about or less than about 4 mg, at least about or less than about 5 mg, at least about or less than about 10 mg, at least about or less than about 15 mg, at least about or less than about 20 mg, at least about or less than about 25 mg, at least about or less than about 30 mg, at least about or less than about 35 mg, at least about or less than about 35 mg, at least about or less than about 40 mg, at least about or less than about 45 mg, at least about or less than about 50 mg, at least about or less than about 55 mg, at least about or less than about 60 mg, at least about or less than about 65 mg, at least about or less than about 70 mg, at least about or less than about 75 mg, at least about or less than about 80 mg, at least about or less than about 85 mg, at least about or less than about 90 mg, at least about or less than about 95 mg, at least about or less than about 100 mg, at least about or less than about 105 mg, at least about or less than about 110 mg, at least about or less than about 115 mg, at least about or less than about 120 mg of a proton pump inhibitor (e.g. omeprazole, esomeprazole, lansoprazole, pantoprazole, rabeprazole, tenatoprazole, leminoprazole, dontoprazole, and ransoprazole) and from at least about or less than about 0.01 g to at least about or less than about 0.3 g (e.g. at least about or less than about 0.01 g, at least about or less than about 0.02 g, at least about or less than about 0.03 g, at least about or less than about 0.04 g, at least about or less than about 0.05 g, at least about or less than about 0.06 g, at least about or less than about 0.07 g, at least about or less than about 0.08 g, at least about or less than about 0.09 g, at least about or less than about 0.1 g, at least about or less than about 0.11 g, at least about or less than about 0.12 g, at least about or less than about 0.13 g, at least about or less than about 0.14 g, at least about or less than about 0.15 g, at least about or less than about 0.16 g, at least about or less than about 0.17 g, at least about or less than about 0.18 g, at least about or less than about 0.19 g, at least about or less than about 0.2 g, at least about or less than about 0.21 g, at least about or less than about 0.22 g, at least about or less than about 0.23 g, at least about or less than about 0.24 g, at least about or less than about 0.25 g, at least about or less than about 0.26 g, at least about or less than about 0.27 g, at least about or less than about 0.28 g, at least about or less than about 0.29 g, at least about or less than about 0.3 g) of a bile acid sequestrant (e.g., cholestyramine, colesevelam, colesevelam-HCl, ursodeoxycholic acid, sevelamer).

A dosage unit (e.g. an oral dosage unit) can include from, for example, from at least about or less than about 5 g to at least about or less than about 150 g (e.g. at least about or less than about 5 g, at least about or less than about 10 g, at least about or less than about 15 g, at least about or less than about 20 g, at least about or less than about 25 g, at least about or less than about 30 g, at least about or less than about 35 g, at least about or less than about 40 g, at least about or less than about 45 g, at least about or less than about 50 g, at least about or less than about 55 g, at least about or less than about 60 g, at least about or less than about 65 g, at least about or less than about 70 g, at least about or less than about 75 g, at least about or less than about 80 g, at least about or less than about 85 g, at least about or less than about 90 g, at least about or less than about 95 g, at least about or less than about 100 g, at least about or less than about 105 g, at least about or less than about 110 g, at least about or less than about 115 g, at least about or less than about 120 g, at least about or less than about 125 g, at least about or less than about 130 g, at least about or less than about 135 g, at least about or less than about 140 g, at least about or less than about 145 g, at least about or less than about 150 g) of a bile acid sequestrant (e.g., cholestyramine, colesevelam, colesevelam-HCl, ursodeoxycholic acid). A dosage unit (e.g. an oral dosage unit) can include from, for example, at least about or less than about 1 to 200 mg, at least about or less than about 5 mg to at least about or less than about 100 mg, at least about or less than about 10 to at least about or less than about 120 mg, at least about or less than about 20 to at least about or less than about 100 mg, at least about or less than about 40 mg to at least about or less than about 100 mg, at least about or less than about 5 to at least about or less than about 80 mg, at least about or less than about 10 to at least about or less than about 40 mg, at least about or less than about 10 mg to at least about or less than about 60 mg, at least about or less than about 1 mg, at least about or less than about 2 mg, at least about or less than about 3 mg, at least about or less than about 4 mg, at least about or less than about 5 mg, at least about or less than about 10 mg, at least about or less than about 15 mg, at least about or less than about 20 mg, at least about or less than about 25 mg, at least about or less than about 30 mg, at least about or less than about 35 mg, at least about or less than about 35 mg, at least about or less than about 40 mg, at least about or less than about 45 mg, at least about or less than about 50 mg, at least about or less than about 55 mg, at least about or less than about 60 mg, at least about or less than about 65 mg, at least about or less than about 70 mg, at least about or less than about 75 mg, at least about or less than about 80 mg, at least about or less than about 85 mg, at least about or less than about 90 mg, at least about or less than about 95 mg, at least about or less than about 100 mg, at least about or less than about 105 mg, at least about or less than about 110 mg, at least about or less than about 115 mg, at least about or less than about 120 mg of a proton pump inhibitor (e.g. omeprazole, esomeprazole, lansoprazole, pantoprazole, rabeprazole, tenatoprazole, leminoprazole, dontoprazole, and ransoprazole) and from at least about or less than about 5 g to at least about or less than about 150 g (e.g. at least about or less than about 5 g, at least about or less than about 10 g, at least about or less than about 15 g, at least about or less than about 20 g, at least about or less than about 25 g, at least about or less than about 30 g, at least about or less than about 35 g, at least about or less than about 40 g, at least about or less than about 45 g, at least about or less than about 50 g, at least about or less than about 55 g, at least about or less than about 60 g, at least about or less than about 65 g, at least about or less than about 70 g, at least about or less than about 75 g, at least about or less than about 80 g, at least about or less than about 85 g, at least about or less than about 90 g, at least about or less than about 95 g, at least about or less than about 100 g, at least about or less than about 105 g, at least about or less than about 110 g, at least about or less than about 115 g, at least about or less than about 120 g, at least about or less than about 125 g, at least about or less than about 130 g, at least about or less than about 135 g, at least about or less than about 140 g, at least about or less than about 145 g, at least about or less than about 150 g) of a bile acid sequestrant (e.g., cholestyramine, colesevelam, colesevelam-HCl, ursodeoxycholic acid).

A dosage unit (e.g. an oral dosage unit) can include from, for example, from at least about or less than about 2 g to at least about or less than about 60 g (e.g. at least about or less than about 2 g, at least about or less than about 4 g, at least about or less than about 6 g, at least about or less than about 8 g, at least about or less than about 10 g, at least about or less than about 12 g, at least about or less than about 14 g, at least about or less than about 16 g, at least about or less than about 18 g, at least about or less than about 20 g, at least about or less than about 22 g, at least about or less than about 24 g, at least about or less than about 26 g, at least about or less than about 28 g, at least about or less than about 30 g, at least about or less than about 32 g, at least about or less than about 34 g, at least about or less than about 36 g, at least about or less than about 38 g, at least about or less than about 40 g, at least about or less than about 42 g, at least about or less than about 44 g, at least about or less than about 46 g, at least about or less than about 48 g, at least about or less than about 50 g, at least about or less than about 52 g, at least about or less than about 54 g, at least about or less than about 56 g, at least about or less than about 58 g, at least about or less than about 60 g) of a bile acid sequestrant (e.g., cholestyramine, colesevelam, colesevelam-HCl, ursodeoxycholic acid). A dosage unit (e.g. an oral dosage unit) can include from, for example, at least about or less than about 1 to at least about or less than about 200 mg, at least about or less than about 5 mg to at least about or less than about 100 mg, at least about or less than about 10 to at least about or less than about 120 mg, at least about or less than about 20 to at least about or less than about 100 mg, at least about or less than about 40 mg to at least about or less than about 100 mg, at least about or less than about 5 to at least about or less than about 80 mg, at least about or less than about 10 to at least about or less than about 40 mg, at least about or less than about 10 mg to at least about or less than about 60 mg, at least about or less than about 1 mg, at least about or less than about 2 mg, at least about or less than about 3 mg, at least about or less than about 4 mg, at least about or less than about 5 mg, at least about or less than about 10 mg, at least about or less than about 15 mg, at least about or less than about 20 mg, at least about or less than about 25 mg, at least about or less than about 30 mg, at least about or less than about 35 mg, at least about or less than about 35 mg, at least about or less than about 40 mg, at least about or less than about 45 mg, at least about or less than about 50 mg, at least about or less than about 55 mg, at least about or less than about 60 mg, at least about or less than about 65 mg, at least about or less than about 70 mg, at least about or less than about 75 mg, at least about or less than about 80 mg, at least about or less than about 85 mg, at least about or less than about 90 mg, at least about or less than about 95 mg, at least about or less than about 100 mg, at least about or less than about 105 mg, at least about or less than about 110 mg, at least about or less than about 115 mg, at least about or less than about 120 mg of a proton pump inhibitor (e.g. omeprazole, esomeprazole, lansoprazole, pantoprazole, rabeprazole, tenatoprazole, leminoprazole, dontoprazole, and ransoprazole) and from at least about or less than about 2 g to at least about or less than about 60 g (e.g. at least about or less than about 2 g, at least about or less than about 4 g, at least about or less than about 6 g, at least about or less than about 8 g, at least about or less than about 10 g, at least about or less than about 12 g, at least about or less than about 14 g, at least about or less than about 16 g, at least about or less than about 18 g, at least about or less than about 20 g, at least about or less than about 22 g, at least about or less than about 24 g, at least about or less than about 26 g, at least about or less than about 28 g, at least about or less than about 30 g, at least about or less than about 32 g, at least about or less than about 34 g, at least about or less than about 36 g, at least about or less than about 38 g, at least about or less than about 40 g, at least about or less than about 42 g, at least about or less than about 44 g, at least about or less than about 46 g, at least about or less than about 48 g, at least about or less than about 50 g, at least about or less than about 52 g, at least about or less than about 54 g, at least about or less than about 56 g, at least about or less than about 58 g, at least about or less than about 60 g) of a bile acid sequestrant (e.g., cholestyramine, colesevelam, colesevelam-HCl, ursodeoxycholic acid).

A dosage unit (e.g. an oral dosage unit) can include from, for example, from at least about or less than about 10 g to at least about or less than about 300 g (e.g. at least about or less than about 10 g, at least about or less than about 20 g, at least about or less than about 30 g, at least about or less than about 40 g, at least about or less than about 50 g, at least about or less than about 60 g, at least about or less than about 70 g, at least about or less than about 80 g, at least about or less than about 90 g, at least about or less than about 100 g, at least about or less than about 110 g, at least about or less than about 120 g, at least about or less than about 130 g, at least about or less than about 140 g, at least about or less than about 150 g, at least about or less than about 160 g, at least about or less than about 170 g, at least about or less than about 180 g, at least about or less than about 190 g, at least about or less than about 200 g, at least about or less than about 210 g, at least about or less than about 220 g, at least about or less than about 230 g, at least about or less than about 240 g, at least about or less than about 250 g, at least about or less than about 260 g, at least about or less than about 270 g, at least about or less than about 280 g, at least about or less than about 290 g, at least about or less than about 300 g) of a bile acid sequestrant (e.g., cholestyramine, colesevelam, colesevelam-HCl, ursodeoxycholic acid). A dosage unit (e.g. an oral dosage unit) can include from, for example, at least about or less than about 1 to at least about or less than about 200 mg, at least about or less than about 5 mg to at least about or less than about 100 mg, at least about or less than about 10 to at least about or less than about 120 mg, at least about or less than about 20 to at least about or less than about 100 mg, at least about or less than about 40 mg to at least about or less than about 100 mg, at least about or less than about 5 to at least about or less than about 80 mg, at least about or less than about 10 to at least about or less than about 40 mg, at least about or less than about 10 mg to at least about or less than about 60 mg, at least about or less than about 1 mg, at least about or less than about 2 mg, at least about or less than about 3 mg, at least about or less than about 4 mg, at least about or less than about 5 mg, at least about or less than about 10 mg, at least about or less than about 15 mg, at least about or less than about 20 mg, at least about or less than about 25 mg, at least about or less than about 30 mg, at least about or less than about 35 mg, at least about or less than about 35 mg, at least about or less than about 40 mg, at least about or less than about 45 mg, at least about or less than about 50 mg, at least about or less than about 55 mg, at least about or less than about 60 mg, at least about or less than about 65 mg, at least about or less than about 70 mg, at least about or less than about 75 mg, at least about or less than about 80 mg, at least about or less than about 85 mg, at least about or less than about 90 mg, at least about or less than about 95 mg, at least about or less than about 100 mg, at least about or less than about 105 mg, at least about or less than about 110 mg, at least about or less than about 115 mg, at least about or less than about 120 mg of a proton pump inhibitor (e.g. omeprazole, esomeprazole, lansoprazole, pantoprazole, rabeprazole, tenatoprazole, leminoprazole, dontoprazole, and ransoprazole) and from at least about or less than about 10 g to at least about or less than about 300 g (e.g. at least about or less than about 10 g, at least about or less than about 20 g, at least about or less than about 30 g, at least about or less than about 40 g, at least about or less than about 50 g, at least about or less than about 60 g, at least about or less than about 70 g, at least about or less than about 80 g, at least about or less than about 90 g, at least about or less than about 100 g, at least about or less than about 110 g, at least about or less than about 120 g, at least about or less than about 130 g, at least about or less than about 140 g, at least about or less than about 150 g, at least about or less than about 160 g, at least about or less than about 170 g, at least about or less than about 180 g, at least about or less than about 190 g, at least about or less than about 200 g, at least about or less than about 210 g, at least about or less than about 220 g, at least about or less than about 230 g, at least about or less than about 240 g, at least about or less than about 250 g, at least about or less than about 260 g, at least about or less than about 270 g, at least about or less than about 280 g, at least about or less than about 290 g, at least about or less than about 300 g) of a bile acid sequestrant (e.g., cholestyramine, colesevelam, colesevelam-HCl, ursodeoxycholic acid).

In certain embodiments, the dosage unit comprises at least about or less than about 5 mg of at least one proton pump inhibitor and at least about or less than about 1 g, at least about or less than about 2 g, at least about or less than about 3 g, at least about or less than about 4 g, at least about or less than about 5 g, at least about or less than about 6 g, at least about or less than about 7 g, at least about or less than about 8 g, at least about or less than about 9 g, at least about or less than about 10 g, at least about or less than about 11 g, at least about or less than about 12 g, at least about or less than about 13 g, at least about or less than about 14 g, at least about or less than about 15 g, at least about or less than about 16 g, at least about or less than about 17 g, at least about or less than about 18 g, at least about or less than about 19 g, at least about or less than about 20 g, at least about or less than about 21 g, at least about or less than about 22 g, at least about or less than about 23 g, at least about or less than about 24 g, at least about or less than about 25 g, at least about or less than about 26 g, at least about or less than about 27 g, at least about or less than about 28 g, at least about or less than about 29 g, or at least about or less than about 30 g of at least one bile acid sequestrant. In certain embodiments, the dosage unit comprises at least about or less than about 10 mg of at least one proton pump inhibitor and at least about or less than about 1 g, at least about or less than about 2 g, at least about or less than about 3 g, at least about or less than about 4 g, at least about or less than about 5 g, at least about or less than about 6 g, at least about or less than about 7 g, at least about or less than about 8 g, at least about or less than about 9 g, at least about or less than about 10 g, at least about or less than about 11 g, at least about or less than about 12 g, at least about or less than about 13 g, at least about or less than about 14 g, at least about or less than about 15 g, at least about or less than about 16 g, at least about or less than about 17 g, at least about or less than about 18 g, at least about or less than about 19 g, at least about or less than about 20 g, at least about or less than about 21 g, at least about or less than about 22 g, at least about or less than about 23 g, at least about or less than about 24 g, at least about or less than about 25 g, at least about or less than about 26 g, at least about or less than about 27 g, at least about or less than about 28 g, at least about or less than about 29 g, or at least about or less than about 30 g of at least one bile acid sequestrant. In certain embodiments, the dosage unit comprises at least about or less than about 15 mg of at least one proton pump inhibitor and at least about or less than about 1 g, at least about or less than about 2 g, at least about or less than about 3 g, at least about or less than about 4 g, at least about or less than about 5 g, at least about or less than about 6 g, at least about or less than about 7 g, at least about or less than about 8 g, at least about or less than about 9 g, at least about or less than about 10 g, at least about or less than about 11 g, at least about or less than about 12 g, at least about or less than about 13 g, at least about or less than about 14 g, at least about or less than about 15 g, at least about or less than about 16 g, at least about or less than about 17 g, at least about or less than about 18 g, at least about or less than about 19 g, at least about or less than about 20 g, at least about or less than about 21 g, at least about or less than about 22 g, at least about or less than about 23 g, at least about or less than about 24 g, at least about or less than about 25 g, at least about or less than about 26 g, at least about or less than about 27 g, at least about or less than about 28 g, at least about or less than about 29 g, or at least about or less than about 30 g of at least one bile acid sequestrant. In certain embodiments, the dosage unit comprises at least about or less than about 20 mg of at least one proton pump inhibitor and at least about or less than about 1 g, at least about or less than about 2 g, at least about or less than about 3 g, at least about or less than about 4 g, at least about or less than about 5 g, at least about or less than about 6 g, at least about or less than about 7 g, at least about or less than about 8 g, at least about or less than about 9 g, at least about or less than about 10 g, at least about or less than about 11 g, at least about or less than about 12 g, at least about or less than about 13 g, at least about or less than about 14 g, at least about or less than about 15 g, at least about or less than about 16 g, at least about or less than about 17 g, at least about or less than about 18 g, at least about or less than about 19 g, at least about or less than about 20 g, at least about or less than about 21 g, at least about or less than about 22 g, at least about or less than about 23 g, at least about or less than about 24 g, at least about or less than about 25 g, at least about or less than about 26 g, at least about or less than about 27 g, at least about or less than about 28 g, at least about or less than about 29 g, or at least about or less than about 30 g of at least one bile acid sequestrant. In certain embodiments, the dosage unit comprises at least about or less than about 25 mg of at least one proton pump inhibitor and at least about or less than about 1 g, at least about or less than about 2 g, at least about or less than about 3 g, at least about or less than about 4 g, at least about or less than about 5 g, at least about or less than about 6 g, at least about or less than about 7 g, at least about or less than about 8 g, at least about or less than about 9 g, at least about or less than about 10 g, at least about or less than about 11 g, at least about or less than about 12 g, at least about or less than about 13 g, at least about or less than about 14 g, at least about or less than about 15 g, at least about or less than about 16 g, at least about or less than about 17 g, at least about or less than about 18 g, at least about or less than about 19 g, at least about or less than about 20 g, at least about or less than about 21 g, at least about or less than about 22 g, at least about or less than about 23 g, at least about or less than about 24 g, at least about or less than about 25 g, at least about or less than about 26 g, at least about or less than about 27 g, at least about or less than about 28 g, at least about or less than about 29 g, or at least about or less than about 30 g of at least one bile acid sequestrant. In certain embodiments, the dosage unit comprises at least about or less than about 30 mg of at least one proton pump inhibitor and at least about or less than about 1 g, at least about or less than about 2 g, at least about or less than about 3 g, at least about or less than about 4 g, at least about or less than about 5 g, at least about or less than about 6 g, at least about or less than about 7 g, at least about or less than about 8 g, at least about or less than about 9 g, at least about or less than about 10 g, at least about or less than about 11 g, at least about or less than about 12 g, at least about or less than about 13 g, at least about or less than about 14 g, at least about or less than about 15 g, at least about or less than about 16 g, at least about or less than about 17 g, at least about or less than about 18 g, at least about or less than about 19 g, at least about or less than about 20 g, at least about or less than about 21 g, at least about or less than about 22 g, at least about or less than about 23 g, at least about or less than about 24 g, at least about or less than about 25 g, at least about or less than about 26 g, at least about or less than about 27 g, at least about or less than about 28 g, at least about or less than about 29 g, or at least about or less than about 30 g of at least one bile acid sequestrant. In certain embodiments, the dosage unit comprises at least about or less than about 35 mg of at least one proton pump inhibitor and at least about or less than about 1 g, at least about or less than about 2 g, at least about or less than about 3 g, at least about or less than about 4 g, at least about or less than about 5 g, at least about or less than about 6 g, at least about or less than about 7 g, at least about or less than about 8 g, at least about or less than about 9 g, at least about or less than about 10 g, at least about or less than about 11 g, at least about or less than about 12 g, at least about or less than about 13 g, at least about or less than about 14 g, at least about or less than about 15 g, at least about or less than about 16 g, at least about or less than about 17 g, at least about or less than about 18 g, at least about or less than about 19 g, at least about or less than about 20 g, at least about or less than about 21 g, at least about or less than about 22 g, at least about or less than about 23 g, at least about or less than about 24 g, at least about or less than about 25 g, at least about or less than about 26 g, at least about or less than about 27 g, at least about or less than about 28 g, at least about or less than about 29 g, or at least about or less than about 30 g of at least one bile acid sequestrant. In certain embodiments, the dosage unit comprises at least about or less than about 40 mg of at least one proton pump inhibitor and at least about or less than about 1 g, at least about or less than about 2 g, at least about or less than about 3 g, at least about or less than about 4 g, at least about or less than about 5 g, at least about or less than about 6 g, at least about or less than about 7 g, at least about or less than about 8 g, at least about or less than about 9 g, at least about or less than about 10 g, at least about or less than about 11 g, at least about or less than about 12 g, at least about or less than about 13 g, at least about or less than about 14 g, at least about or less than about 15 g, at least about or less than about 16 g, at least about or less than about 17 g, at least about or less than about 18 g, at least about or less than about 19 g, at least about or less than about 20 g, at least about or less than about 21 g, at least about or less than about 22 g, at least about or less than about 23 g, at least about or less than about 24 g, at least about or less than about 25 g, at least about or less than about 26 g, at least about or less than about 27 g, at least about or less than about 28 g, at least about or less than about 29 g, or at least about or less than about 30 g of at least one bile acid sequestrant. In certain embodiments, the dosage unit comprises at least about or less than about 45 mg of at least one proton pump inhibitor and at least about or less than about 1 g, at least about or less than about 2 g, at least about or less than about 3 g, at least about or less than about 4 g, at least about or less than about 5 g, at least about or less than about 6 g, at least about or less than about 7 g, at least about or less than about 8 g, at least about or less than about 9 g, at least about or less than about 10 g, at least about or less than about 11 g, at least about or less than about 12 g, at least about or less than about 13 g, at least about or less than about 14 g, at least about or less than about 15 g, at least about or less than about 16 g, at least about or less than about 17 g, at least about or less than about 18 g, at least about or less than about 19 g, at least about or less than about 20 g, at least about or less than about 21 g, at least about or less than about 22 g, at least about or less than about 23 g, at least about or less than about 24 g, at least about or less than about 25 g, at least about or less than about 26 g, at least about or less than about 27 g, at least about or less than about 28 g, at least about or less than about 29 g, or at least about or less than about 30 g of at least one bile acid sequestrant. In certain embodiments, the dosage unit comprises at least about or less than about 50 mg of at least one proton pump inhibitor and at least about or less than about 1 g, at least about or less than about 2 g, at least about or less than about 3 g, at least about or less than about 4 g, at least about or less than about 5 g, at least about or less than about 6 g, at least about or less than about 7 g, at least about or less than about 8 g, at least about or less than about 9 g, at least about or less than about 10 g, at least about or less than about 11 g, at least about or less than about 12 g, at least about or less than about 13 g, at least about or less than about 14 g, at least about or less than about 15 g, at least about or less than about 16 g, at least about or less than about 17 g, at least about or less than about 18 g, at least about or less than about 19 g, at least about or less than about 20 g, at least about or less than about 21 g, at least about or less than about 22 g, at least about or less than about 23 g, at least about or less than about 24 g, at least about or less than about 25 g, at least about or less than about 26 g, at least about or less than about 27 g, at least about or less than about 28 g, at least about or less than about 29 g, or at least about or less than about 30 g of at least one bile acid sequestrant. In certain embodiments, the dosage unit comprises at least about or less than about 55 mg of at least one proton pump inhibitor and at least about or less than about 1 g, at least about or less than about 2 g, at least about or less than about 3 g, at least about or less than about 4 g, at least about or less than about 5 g, at least about or less than about 6 g, at least about or less than about 7 g, at least about or less than about 8 g, at least about or less than about 9 g, at least about or less than about 10 g, at least about or less than about 11 g, at least about or less than about 12 g, at least about or less than about 13 g, at least about or less than about 14 g, at least about or less than about 15 g, at least about or less than about 16 g, at least about or less than about 17 g, at least about or less than about 18 g, at least about or less than about 19 g, at least about or less than about 20 g, at least about or less than about 21 g, at least about or less than about 22 g, at least about or less than about 23 g, at least about or less than about 24 g, at least about or less than about 25 g, at least about or less than about 26 g, at least about or less than about 27 g, at least about or less than about 28 g, at least about or less than about 29 g, or at least about or less than about 30 g of at least one bile acid sequestrant. In certain embodiments, the dosage unit comprises at least about or less than about 60 mg of at least one proton pump inhibitor and at least about or less than about 1 g, at least about or less than about 2 g, at least about or less than about 3 g, at least about or less than about 4 g, at least about or less than about 5 g, at least about or less than about 6 g, at least about or less than about 7 g, at least about or less than about 8 g, at least about or less than about 9 g, at least about or less than about 10 g, at least about or less than about 11 g, at least about or less than about 12 g, at least about or less than about 13 g, at least about or less than about 14 g, at least about or less than about 15 g, at least about or less than about 16 g, at least about or less than about 17 g, at least about or less than about 18 g, at least about or less than about 19 g, at least about or less than about 20 g, at least about or less than about 21 g, at least about or less than about 22 g, at least about or less than about 23 g, at least about or less than about 24 g, at least about or less than about 25 g, at least about or less than about 26 g, at least about or less than about 27 g, at least about or less than about 28 g, at least about or less than about 29 g, or at least about or less than about 30 g of at least one bile acid sequestrant. In certain embodiments, the dosage unit comprises at least about or less than about 65 mg of at least one proton pump inhibitor and at least about or less than about 1 g, at least about or less than about 2 g, at least about or less than about 3 g, at least about or less than about 4 g, at least about or less than about 5 g, at least about or less than about 6 g, at least about or less than about 7 g, at least about or less than about 8 g, at least about or less than about 9 g, at least about or less than about 10 g, at least about or less than about 11 g, at least about or less than about 12 g, at least about or less than about 13 g, at least about or less than about 14 g, at least about or less than about 15 g, at least about or less than about 16 g, at least about or less than about 17 g, at least about or less than about 18 g, at least about or less than about 19 g, at least about or less than about 20 g, at least about or less than about 21 g, at least about or less than about 22 g, at least about or less than about 23 g, at least about or less than about 24 g, at least about or less than about 25 g, at least about or less than about 26 g, at least about or less than about 27 g, at least about or less than about 28 g, at least about or less than about 29 g, or at least about or less than about 30 g of at least one bile acid sequestrant. In certain embodiments, the dosage unit comprises at least about or less than about 70 mg of at least one proton pump inhibitor and at least about or less than about 1 g, at least about or less than about 2 g, at least about or less than about 3 g, at least about or less than about 4 g, at least about or less than about 5 g, at least about or less than about 6 g, at least about or less than about 7 g, at least about or less than about 8 g, at least about or less than about 9 g, at least about or less than about 10 g, at least about or less than about 11 g, at least about or less than about 12 g, at least about or less than about 13 g, at least about or less than about 14 g, at least about or less than about 15 g, at least about or less than about 16 g, at least about or less than about 17 g, at least about or less than about 18 g, at least about or less than about 19 g, at least about or less than about 20 g, at least about or less than about 21 g, at least about or less than about 22 g, at least about or less than about 23 g, at least about or less than about 24 g, at least about or less than about 25 g, at least about or less than about 26 g, at least about or less than about 27 g, at least about or less than about 28 g, at least about or less than about 29 g, or at least about or less than about 30 g of at least one bile acid sequestrant. In certain embodiments, the dosage unit comprises at least about or less than about 75 mg of at least one proton pump inhibitor and at least about or less than about 1 g, at least about or less than about 2 g, at least about or less than about 3 g, at least about or less than about 4 g, at least about or less than about 5 g, at least about or less than about 6 g, at least about or less than about 7 g, at least about or less than about 8 g, at least about or less than about 9 g, at least about or less than about 10 g, at least about or less than about 11 g, at least about or less than about 12 g, at least about or less than about 13 g, at least about or less than about 14 g, at least about or less than about 15 g, at least about or less than about 16 g, at least about or less than about 17 g, at least about or less than about 18 g, at least about or less than about 19 g, at least about or less than about 20 g, at least about or less than about 21 g, at least about or less than about 22 g, at least about or less than about 23 g, at least about or less than about 24 g, at least about or less than about 25 g, at least about or less than about 26 g, at least about or less than about 27 g, at least about or less than about 28 g, at least about or less than about 29 g, or at least about or less than about 30 g of at least one bile acid sequestrant. In certain embodiments, the dosage unit comprises at least about or less than about 80 mg of at least one proton pump inhibitor and at least about or less than about 1 g, at least about or less than about 2 g, at least about or less than about 3 g, at least about or less than about 4 g, at least about or less than about 5 g, at least about or less than about 6 g, at least about or less than about 7 g, at least about or less than about 8 g, at least about or less than about 9 g, at least about or less than about 10 g, at least about or less than about 11 g, at least about or less than about 12 g, at least about or less than about 13 g, at least about or less than about 14 g, at least about or less than about 15 g, at least about or less than about 16 g, at least about or less than about 17 g, at least about or less than about 18 g, at least about or less than about 19 g, at least about or less than about 20 g, at least about or less than about 21 g, at least about or less than about 22 g, at least about or less than about 23 g, at least about or less than about 24 g, at least about or less than about 25 g, at least about or less than about 26 g, at least about or less than about 27 g, at least about or less than about 28 g, at least about or less than about 29 g, or at least about or less than about 30 g of at least one bile acid sequestrant. In certain embodiments, the dosage unit comprises at least about or less than about 85 mg of at least one proton pump inhibitor and at least about or less than about 1 g, at least about or less than about 2 g, at least about or less than about 3 g, at least about or less than about 4 g, at least about or less than about 5 g, at least about or less than about 6 g, at least about or less than about 7 g, at least about or less than about 8 g, at least about or less than about 9 g, at least about or less than about 10 g, at least about or less than about 11 g, at least about or less than about 12 g, at least about or less than about 13 g, at least about or less than about 14 g, at least about or less than about 15 g, at least about or less than about 16 g, at least about or less than about 17 g, at least about or less than about 18 g, at least about or less than about 19 g, at least about or less than about 20 g, at least about or less than about 21 g, at least about or less than about 22 g, at least about or less than about 23 g, at least about or less than about 24 g, at least about or less than about 25 g, at least about or less than about 26 g, at least about or less than about 27 g, at least about or less than about 28 g, at least about or less than about 29 g, or at least about or less than about 30 g of at least one bile acid sequestrant. In certain embodiments, the dosage unit comprises at least about or less than about 90 mg of at least one proton pump inhibitor and at least about or less than about 1 g, at least about or less than about 2 g, at least about or less than about 3 g, at least about or less than about 4 g, at least about or less than about 5 g, at least about or less than about 6 g, at least about or less than about 7 g, at least about or less than about 8 g, at least about or less than about 9 g, at least about or less than about 10 g, at least about or less than about 11 g, at least about or less than about 12 g, at least about or less than about 13 g, at least about or less than about 14 g, at least about or less than about 15 g, at least about or less than about 16 g, at least about or less than about 17 g, at least about or less than about 18 g, at least about or less than about 19 g, at least about or less than about 20 g, at least about or less than about 21 g, at least about or less than about 22 g, at least about or less than about 23 g, at least about or less than about 24 g, at least about or less than about 25 g, at least about or less than about 26 g, at least about or less than about 27 g, at least about or less than about 28 g, at least about or less than about 29 g, or at least about or less than about 30 g of at least one bile acid sequestrant. In certain embodiments, the dosage unit comprises at least about or less than about 95 mg of at least one proton pump inhibitor and at least about or less than about 1 g, at least about or less than about 2 g, at least about or less than about 3 g, at least about or less than about 4 g, at least about or less than about 5 g, at least about or less than about 6 g, at least about or less than about 7 g, at least about or less than about 8 g, at least about or less than about 9 g, at least about or less than about 10 g, at least about or less than about 11 g, at least about or less than about 12 g, at least about or less than about 13 g, at least about or less than about 14 g, at least about or less than about 15 g, at least about or less than about 16 g, at least about or less than about 17 g, at least about or less than about 18 g, at least about or less than about 19 g, at least about or less than about 20 g, at least about or less than about 21 g, at least about or less than about 22 g, at least about or less than about 23 g, at least about or less than about 24 g, at least about or less than about 25 g, at least about or less than about 26 g, at least about or less than about 27 g, at least about or less than about 28 g, at least about or less than about 29 g, or at least about or less than about 30 g of at least one bile acid sequestrant. In certain embodiments, the dosage unit comprises at least about or less than about 100 mg of at least one proton pump inhibitor and at least about or less than about 1 g, at least about or less than about 2 g, at least about or less than about 3 g, at least about or less than about 4 g, at least about or less than about 5 g, at least about or less than about 6 g, at least about or less than about 7 g, at least about or less than about 8 g, at least about or less than about 9 g, at least about or less than about 10 g, at least about or less than about 11 g, at least about or less than about 12 g, at least about or less than about 13 g, at least about or less than about 14 g, at least about or less than about 15 g, at least about or less than about 16 g, at least about or less than about 17 g, at least about or less than about 18 g, at least about or less than about 19 g, at least about or less than about 20 g, at least about or less than about 21 g, at least about or less than about 22 g, at least about or less than about 23 g, at least about or less than about 24 g, at least about or less than about 25 g, at least about or less than about 26 g, at least about or less than about 27 g, at least about or less than about 28 g, at least about or less than about 29 g, or at least about or less than about 30 g of at least one bile acid sequestrant. In certain embodiments the at least one proton pump inhibitor is omeprazole. In certain embodiments the at least one proton pump inhibitor is esomeprazole. In certain embodiments the at least one proton pump inhibitor is lansoprazole. In certain embodiments the at least one proton pump inhibitor is pantoprazole. In certain embodiments the at least one proton pump inhibitor is rabeprazole. In certain embodiments the at least one proton pump inhibitor is tenatoprazole. In certain embodiments the at least one bile acid sequestrant is cholestyramine. In certain embodiments the at least one bile acid sequestrant is colesevelam. In certain embodiments the at least one bile acid sequestrant is colesevelam-HCl. In certain embodiments the at least one bile acid sequestrant is colestipol. In certain embodiments the at least one proton pump inhibitor is omeprazole and the at least one bile acid sequestrant is cholestyramine. In certain embodiments the at least one proton pump inhibitor is omeprazole and the at least one bile acid sequestrant is colesevelam. In certain embodiments the at least one proton pump inhibitor is omeprazole and the at least one bile acid sequestrant is colesevelam-HCl. In certain embodiments the at least one proton pump inhibitor is omeprazole and the at least one bile acid sequestrant is colestipol. In certain embodiments the at least one proton pump inhibitor is esomeprazole and the at least one bile acid sequestrant is cholestyramine. In certain embodiments the at least one proton pump inhibitor is esomeprazole and the at least one bile acid sequestrant is colesevelam. In certain embodiments the at least one proton pump inhibitor is esomeprazole and the at least one bile acid sequestrant is colesevelam-HCl. In certain embodiments the at least one proton pump inhibitor is esomeprazole and the at least one bile acid sequestrant is colestipol. In certain embodiments the at least one proton pump inhibitor is lansoprazole and the at least one bile acid sequestrant is cholestyramine. In certain embodiments the at least one proton pump inhibitor is lansoprazole and the at least one bile acid sequestrant is colesevelam. In certain embodiments the at least one proton pump inhibitor is lansoprazole and the at least one bile acid sequestrant is colesevelam-HCl. In certain embodiments the at least one proton pump inhibitor is lansoprazole and the at least one bile acid sequestrant is colestipol. In certain embodiments the at least one proton pump inhibitor is pantoprazole and the at least one bile acid sequestrant is cholestyramine. In certain embodiments the at least one proton pump inhibitor is pantoprazole and the at least one bile acid sequestrant is colesevelam. In certain embodiments the at least one proton pump inhibitor is pantoprazole and the at least one bile acid sequestrant is colesevelam-HCl. In certain embodiments the at least one proton pump inhibitor is pantoprazole and the at least one bile acid sequestrant is colestipol. In certain embodiments the at least one proton pump inhibitor is rabeprazole and the at least one bile acid sequestrant is cholestyramine. In certain embodiments the at least one proton pump inhibitor is rabeprazole and the at least one bile acid sequestrant is colesevelam. In certain embodiments the at least one proton pump inhibitor is rabeprazole and the at least one bile acid sequestrant is colesevelam-HCl. In certain embodiments the at least one proton pump inhibitor is rabeprazole and the at least one bile acid sequestrant is colestipol. In certain embodiments the at least one proton pump inhibitor is tenatoprazole and the at least one bile acid sequestrant is cholestyramine. In certain embodiments the at least one proton pump inhibitor is tenatoprazole and the at least one bile acid sequestrant is colesevelam. In certain embodiments the at least one proton pump inhibitor is tenatoprazole and the at least one bile acid sequestrant is colesevelam-HCl. In certain embodiments the at least one proton pump inhibitor is tenatoprazole and the at least one bile acid sequestrant is colestipol. In certain embodiments the dosage unit and daily dose are equivalent. In various embodiments, the dosage unit is administered with food at anytime of the day, without food at anytime of the day, with food after an overnight fast (e.g. with breakfast), at bedtime after a low fat snack. In various embodiments, the dosage unit is administered once a day, twice a day, three times a day, four times a day. The dosage unit can optionally comprise other agents such as at least one antacid, at least one histamine $H_2$-receptor antagonist, or combinations thereof.

In certain embodiments, the dosage unit comprises at least about or less than about 5 mg of at least one proton pump inhibitor and at least about or less than about 0.2 g, at least about or less than about 0.4 g, at least about or less than about 0.6 g, at least about or less than about 0.8 g, at least about or less than about 1 g, at least about or less than about 1.2 g, at least about or less than about 1.4 g, at least about or less than about 1.6 g, at least about or less than about 1.8 g, at least about or less than about 2 g, at least about or less than about 2.2 g, at least about or less than about 2.4 g, at least about or less than about 2.6 g, at least about or less than about 2.8 g, at least about or less than about 3 g, at least about or less than about 3.2 g, at least about or less than about 3.4 g, at least about or less than about 3.6 g, at least about or less than about 3.8 g, at least about or less than about 4 g, at least about or less than about 4.2 g, at least about or less than about 4.4 g, at least about or less than about 4.6 g, at least about or less than about 4.8 g, at least about or less than about 5 g, at least about or less than about 5.2 g, at least about or less than about 5.4 g, at least about or less than about 5.6 g, at least about or less than about 5.8 g, or at least about or less than about 6 g of at least one bile acid sequestrant. In certain embodiments, the dosage unit comprises at least about or less than about 10 mg of at least one proton pump inhibitor and at least about or less than about 0.2 g, at least about or less than about 0.4 g, at least about or less than about 0.6 g, at least about or less than about 0.8 g, at least about or less than about 1 g, at least about or less than about 1.2 g, at least about or less than about 1.4 g, at least about or less than about 1.6 g, at least about or less than about 1.8 g, at least about or less than about 2 g, at least about or less than about 2.2 g, at least about or less than about 2.4 g, at least about or less than about 2.6 g, at least about or less than about 2.8 g, at least about or less than about 3 g, at least about or less than about 3.2 g, at least about or less than about 3.4 g, at least about or less than about 3.6 g, at least about or less than about 3.8 g, at least about or less than about 4 g, at least about or less than about 4.2 g, at least about or less than about 4.4 g, at least about or less than about 4.6 g, at least about or less than about 4.8 g, at least about or less than about 5 g, at least about or less than about 5.2 g, at least about or less than about 5.4 g, at least about or less than about 5.6 g, at least about or less than about 5.8 g, or at least about or less than about 6 g of at least one bile acid sequestrant. In certain embodiments, the dosage unit comprises at least about or less than about 15 mg of at least one proton pump inhibitor and at least about or less than about 0.2 g, at least about or less than about 0.4 g, at least about or less than about 0.6 g, at least about or less than about 0.8 g, at least about or less than about 1 g, at least about or less than about 1.2 g, at least about or less than about 1.4 g, at least about or less than about 1.6 g, at least about or less than about 1.8 g, at least about or less than about 2 g, at least about or less than about 2.2 g, at least about or less than about 2.4 g, at least about or less than about 2.6 g, at least about or less than about 2.8 g, at least about or less than about 3 g, at least about or less than about 3.2 g, at least about or less than about 3.4 g, at least about or less than about 3.6 g, at least about or less than about 3.8 g, at least about or less than about 4 g, at least about or less than about 4.2 g, at least about or less than about 4.4 g, at least about or less than about 4.6 g, at least about or less than about 4.8 g, at least about or less than about 5 g, at least about or less than about 5.2 g, at least about or less than about 5.4 g, at least about or less than about 5.6 g, at least about or less than about 5.8 g, or at least about or less than about 6 g of at least one bile acid sequestrant. In certain embodiments, the dosage unit comprises at least about or less than about 20 mg of at least one proton pump inhibitor and at least about or less than about 0.2 g, at least about or less than about 0.4 g, at least about or less than about 0.6 g, at least about or less than about 0.8 g, at least about or less than about 1 g, at least about or less than about 1.2 g, at least about or less than about 1.4 g, at least about or less than about 1.6 g, at least about or less than about 1.8 g, at least about or less than about 2 g, at least about or less than about 2.2 g, at least about or less than about 2.4 g, at least about or less than about 2.6 g, at least about or less than about 2.8 g, at least about or less than about 3 g, at least about or less than about 3.2 g, at least about or less than about 3.4 g, at least about or less than about 3.6 g, at least about or less than about 3.8 g, at least about or less than about 4 g, at least about or less than about 4.2 g, at least about or less than about 4.4 g, at least about or less than about 4.6 g, at least about or less than about 4.8 g, at least about or less than about 5 g, at least about or less than about 5.2 g, at least about or less than about 5.4 g, at least about or less than about 5.6 g, at least about or less than about 5.8 g, or at least about or less than about 6 g of at least one bile acid sequestrant. In certain embodiments, the dosage unit comprises at least about or less than about 25 mg of at least one proton pump inhibitor and at least about or less than about 0.2 g, at least about or less than about 0.4 g, at least about or less than about 0.6 g, at least about or less than about 0.8 g, at least about or less than about 1 g, at least about or less than about 1.2 g, at least about or less than about 1.4 g, at least about or less than about 1.6 g, at least about or less than about 1.8 g, at least about or less than about 2 g, at least about or less than about 2.2 g, at least about or less than about 2.4 g, at least about or less than about 2.6 g, at least about or less than about 2.8 g, at least about or less than about 3 g, at least about or less than about 3.2 g, at least about or less than about 3.4 g, at least about or less than about 3.6 g, at least about or less than about 3.8 g, at least about or less than about 4 g, at least about or less than about 4.2 g, at least about or less than about 4.4 g, at least about or less than about 4.6 g, at least about or less than about 4.8 g, at least about or less than about 5 g, at least about or less than about 5.2 g, at least about or less than about 5.4 g, at least about or less than about 5.6 g, at least about or less than about 5.8 g, or at least about or less than about 6 g of at least one bile acid sequestrant. In certain embodiments, the dosage unit comprises at least about or less than about 30 mg of at least one proton pump inhibitor and at least about or less than about 0.2 g, at least about or less than about 0.4 g, at least about or less than about 0.6 g, at least about or less than about 0.8 g, at least about or less than about 1 g, at least about or less than about 1.2 g, at least about or less than about 1.4 g, at least about or less than about 1.6 g, at least about or less than about 1.8 g, at least about or less than about 2 g, at least about or less than about 2.2 g, at least about or less than about 2.4 g, at least about or less than about 2.6 g, at least about or less than about 2.8 g, at least about or less than about 3 g, at least about or less than about 3.2 g, at least about or less than about 3.4 g, at least about or less than about 3.6 g, at least about or less than about 3.8 g, at least about or less than about 4 g, at least about or less than about 4.2 g, at least about or less than about 4.4 g, at least about or less than about 4.6 g, at least about or less than about 4.8 g, at least about or less than about 5 g, at least about or less than about 5.2 g, at least about or less than about 5.4 g, at least about or less than about 5.6 g, at least about or less than about 5.8 g, or at least about or less than about 6 g of at least one bile acid sequestrant. In certain embodiments, the dosage unit comprises at least about or less than about 35 mg of at least one proton pump inhibitor and at least about or less than about 0.2 g, at least about or less than about 0.4 g, at least about or less than about 0.6 g, at least about or less than about 0.8 g, at least about or less than about 1 g, at least about or less than about 1.2 g, at least about or less than about 1.4 g, at least about or less than about 1.6 g, at least about or less than about 1.8 g, at least about or less than about 2 g, at least about or less than about 2.2 g, at least about or less than about 2.4 g, at least about or less than about 2.6 g, at least about or less than about 2.8 g, at least about or less than about 3 g, at least about or less than about 3.2 g, at least about or less than about 3.4 g, at least about or less than about 3.6 g, at least about or less than about 3.8 g, at least about or less than about 4 g, at least about or less than about 4.2 g, at least about or less than about 4.4 g, at least about or less than about 4.6 g, at least about or less than about 4.8 g, at least about or less than about 5 g, at least about or less than about 5.2 g, at least about or less than about 5.4 g, at least about or less than about 5.6 g, at least about or less than about 5.8 g, or at least about or less than about 6 g of at least one bile acid sequestrant. In certain embodiments, the dosage unit comprises at least about or less than about 40 mg of at least one proton pump inhibitor and at least about or less than about 0.2 g, at least about or less than about 0.4 g, at least about or less than about 0.6 g, at least about or less than about 0.8 g, at least about or less than about 1 g, at least about or less than about 1.2 g, at least about or less than about 1.4 g, at least about or less than about 1.6 g, at least about or less than about 1.8 g, at least about or less than about 2 g, at least about or less than about 2.2 g, at least about or less than about 2.4 g, at least about or less than about 2.6 g, at least about or less than about 2.8 g, at least about or less than about 3 g, at least about or less than about 3.2 g, at least about or less than about 3.4 g, at least about or less than about 3.6 g, at least about or less than about 3.8 g, at least about or less than about 4 g, at least about or less than about 4.2 g, at least about or less than about 4.4 g, at least about or less than about 4.6 g, at least about or less than about 4.8 g, at least about or less than about 5 g, at least about or less than about 5.2 g, at least about or less than about 5.4 g, at least about or less than about 5.6 g, at least about or less than about 5.8 g, or at least about or less than about 6 g of at least one bile acid sequestrant. In certain embodiments, the dosage unit comprises at least about or less than about 45 mg of at least one proton pump inhibitor and at least about or less than about 0.2 g, at least about or less than about 0.4 g, at least about or less than about 0.6 g, at least about or less than about 0.8 g, at least about or less than about 1 g, at least about or less than about 1.2 g, at least about or less than about 1.4 g, at least about or less than about 1.6 g, at least about or less than about 1.8 g, at least about or less than about 2 g, at least about or less than about 2.2 g, at least about or less than about 2.4 g, at least about or less than about 2.6 g, at least about or less than about 2.8 g, at least about or less than about 3 g, at least about or less than about 3.2 g, at least about or less than about 3.4 g, at least about or less than about 3.6 g, at least about or less than about 3.8 g, at least about or less than about 4 g, at least about or less than about 4.2 g, at least about or less than about 4.4 g, at least about or less than about 4.6 g, at least about or less than about 4.8 g, at least about or less than about 5 g, at least about or less than about 5.2 g, at least about or less than about 5.4 g, at least about or less than about 5.6 g, at least about or less than about 5.8 g, or at least about or less than about 6 g of at least one bile acid sequestrant. In certain embodiments, the dosage unit comprises at least about or less than about 50 mg of at least one proton pump inhibitor and at least about or less than about 0.2 g, at least about or less than about 0.4 g, at least about or less than about 0.6 g, at least about or less than about 0.8 g, at least about or less than about 1 g, at least about or less than about 1.2 g, at least about or less than about 1.4 g, at least about or less than about 1.6 g, at least about or less than about 1.8 g, at least about or less than about 2 g, at least about or less than about 2.2 g, at least about or less than about 2.4 g, at least about or less than about 2.6 g, at least about or less than about 2.8 g, at least about or less than about 3 g, at least about or less than about 3.2 g, at least about or less than about 3.4 g, at least about or less than about 3.6 g, at least about or less than about 3.8 g, at least about or less than about 4 g, at least about or less than about 4.2 g, at least about or less than about 4.4 g, at least about or less than about 4.6 g, at least about or less than about 4.8 g, at least about or less than about 5 g, at least about or less than about 5.2 g, at least about or less than about 5.4 g, at least about or less than about 5.6 g, at least about or less than about 5.8 g, or at least about or less than about 6 g of at least one bile acid sequestrant. In certain embodiments, the dosage unit comprises at least about or less than about 55 mg of at least one proton pump inhibitor and at least about or less than about 0.2 g, at least about or less than about 0.4 g, at least about or less than about 0.6 g, at least about or less than about 0.8 g, at least about or less than about 1 g, at least about or less than about 1.2 g, at least about or less than about 1.4 g, at least about or less than about 1.6 g, at least about or less than about 1.8 g, at least about or less than about 2 g, at least about or less than about 2.2 g, at least about or less than about 2.4 g, at least about or less than about 2.6 g, at least about or less than about 2.8 g, at least about or less than about 3 g, at least about or less than about 3.2 g, at least about or less than about 3.4 g, at least about or less than about 3.6 g, at least about or less than about 3.8 g, at least about or less than about 4 g, at least about or less than about 4.2 g, at least about or less than about 4.4 g, at least about or less than about 4.6 g, at least about or less than about 4.8 g, at least about or less than about 5 g, at least about or less than about 5.2 g, at least about or less than about 5.4 g, at least about or less than about 5.6 g, at least about or less than about 5.8 g, or at least about or less than about 6 g of at least one bile acid sequestrant. In certain embodiments, the dosage unit comprises at least about or less than about 60 mg of at least one proton pump inhibitor and at least about or less than about 0.2 g, at least about or less than about 0.4 g, at least about or less than about 0.6 g, at least about or less than about 0.8 g, at least about or less than about 1 g, at least about or less than about 1.2 g, at least about or less than about 1.4 g, at least about or less than about 1.6 g, at least about or less than about 1.8 g, at least about or less than about 2 g, at least about or less than about 2.2 g, at least about or less than about 2.4 g, at least about or less than about 2.6 g, at least about or less than about 2.8 g, at least about or less than about 3 g, at least about or less than about 3.2 g, at least about or less than about 3.4 g, at least about or less than about 3.6 g, at least about or less than about 3.8 g, at least about or less than about 4 g, at least about or less than about 4.2 g, at least about or less than about 4.4 g, at least about or less than about 4.6 g, at least about or less than about 4.8 g, at least about or less than about 5 g, at least about or less than about 5.2 g, at least about or less than about 5.4 g, at least about or less than about 5.6 g, at least about or less than about 5.8 g, or at least about or less than about 6 g of at least one bile acid sequestrant. In certain embodiments, the dosage unit comprises at least about or less than about 65 mg of at least one proton pump inhibitor and at least about or less than about 0.2 g, at least about or less than about 0.4 g, at least about or less than about 0.6 g, at least about or less than about 0.8 g, at least about or less than about 1 g, at least about or less than about 1.2 g, at least about or less than about 1.4 g, at least about or less than about 1.6 g, at least about or less than about 1.8 g, at least about or less than about 2 g, at least about or less than about 2.2 g, at least about or less than about 2.4 g, at least about or less than about 2.6 g, at least about or less than about 2.8 g, at least about or less than about 3 g, at least about or less than about 3.2 g, at least about or less than about 3.4 g, at least about or less than about 3.6 g, at least about or less than about 3.8 g, at least about or less than about 4 g, at least about or less than about 4.2 g, at least about or less than about 4.4 g, at least about or less than about 4.6 g, at least about or less than about 4.8 g, at least about or less than about 5 g, at least about or less than about 5.2 g, at least about or less than about 5.4 g, at least about or less than about 5.6 g, at least about or less than about 5.8 g, or at least about or less than about 6 g of at least one bile acid sequestrant. In certain embodiments, the dosage unit comprises at least about or less than about 70 mg of at least one proton pump inhibitor and at least about or less than about 0.2 g, at least about or less than about 0.4 g, at least about or less than about 0.6 g, at least about or less than about 0.8 g, at least about or less than about 1 g, at least about or less than about 1.2 g, at least about or less than about 1.4 g, at least about or less than about 1.6 g, at least about or less than about 1.8 g, at least about or less than about 2 g, at least about or less than about 2.2 g, at least about or less than about 2.4 g, at least about or less than about 2.6 g, at least about or less than about 2.8 g, at least about or less than about 3 g, at least about or less than about 3.2 g, at least about or less than about 3.4 g, at least about or less than about 3.6 g, at least about or less than about 3.8 g, at least about or less than about 4 g, at least about or less than about 4.2 g, at least about or less than about 4.4 g, at least about or less than about 4.6 g, at least about or less than about 4.8 g, at least about or less than about 5 g, at least about or less than about 5.2 g, at least about or less than about 5.4 g, at least about or less than about 5.6 g, at least about or less than about 5.8 g, or at least about or less than about 6 g of at least one bile acid sequestrant. In certain embodiments, the dosage unit comprises at least about or less than about 75 mg of at least one proton pump inhibitor and at least about or less than about 0.2 g, at least about or less than about 0.4 g, at least about or less than about 0.6 g, at least about or less than about 0.8 g, at least about or less than about 1 g, at least about or less than about 1.2 g, at least about or less than about 1.4 g, at least about or less than about 1.6 g, at least about or less than about 1.8 g, at least about or less than about 2 g, at least about or less than about 2.2 g, at least about or less than about 2.4 g, at least about or less than about 2.6 g, at least about or less than about 2.8 g, at least about or less than about 3 g, at least about or less than about 3.2 g, at least about or less than about 3.4 g, at least about or less than about 3.6 g, at least about or less than about 3.8 g, at least about or less than about 4 g, at least about or less than about 4.2 g, at least about or less than about 4.4 g, at least about or less than about 4.6 g, at least about or less than about 4.8 g, at least about or less than about 5 g, at least about or less than about 5.2 g, at least about or less than about 5.4 g, at least about or less than about 5.6 g, at least about or less than about 5.8 g, or at least about or less than about 6 g of at least one bile acid sequestrant. In certain embodiments, the dosage unit comprises at least about or less than about 80 mg of at least one proton pump inhibitor and at least about or less than about 0.2 g, at least about or less than about 0.4 g, at least about or less than about 0.6 g, at least about or less than about 0.8 g, at least about or less than about 1 g, at least about or less than about 1.2 g, at least about or less than about 1.4 g, at least about or less than about 1.6 g, at least about or less than about 1.8 g, at least about or less than about 2 g, at least about or less than about 2.2 g, at least about or less than about 2.4 g, at least about or less than about 2.6 g, at least about or less than about 2.8 g, at least about or less than about 3 g, at least about or less than about 3.2 g, at least about or less than about 3.4 g, at least about or less than about 3.6 g, at least about or less than about 3.8 g, at least about or less than about 4 g, at least about or less than about 4.2 g, at least about or less than about 4.4 g, at least about or less than about 4.6 g, at least about or less than about 4.8 g, at least about or less than about 5 g, at least about or less than about 5.2 g, at least about or less than about 5.4 g, at least about or less than about 5.6 g, at least about or less than about 5.8 g, or at least about or less than about 6 g of at least one bile acid sequestrant. In certain embodiments, the dosage unit comprises at least about or less than about 85 mg of at least one proton pump inhibitor and at least about or less than about 0.2 g, at least about or less than about 0.4 g, at least about or less than about 0.6 g, at least about or less than about 0.8 g, at least about or less than about 1 g, at least about or less than about 1.2 g, at least about or less than about 1.4 g, at least about or less than about 1.6 g, at least about or less than about 1.8 g, at least about or less than about 2 g, at least about or less than about 2.2 g, at least about or less than about 2.4 g, at least about or less than about 2.6 g, at least about or less than about 2.8 g, at least about or less than about 3 g, at least about or less than about 3.2 g, at least about or less than about 3.4 g, at least about or less than about 3.6 g, at least about or less than about 3.8 g, at least about or less than about 4 g, at least about or less than about 4.2 g, at least about or less than about 4.4 g, at least about or less than about 4.6 g, at least about or less than about 4.8 g, at least about or less than about 5 g, at least about or less than about 5.2 g, at least about or less than about 5.4 g, at least about or less than about 5.6 g, at least about or less than about 5.8 g, or at least about or less than about 6 g of at least one bile acid sequestrant. In certain embodiments, the dosage unit comprises at least about or less than about 90 mg of at least one proton pump inhibitor and at least about or less than about 0.2 g, at least about or less than about 0.4 g, at least about or less than about 0.6 g, at least about or less than about 0.8 g, at least about or less than about 1 g, at least about or less than about 1.2 g, at least about or less than about 1.4 g, at least about or less than about 1.6 g, at least about or less than about 1.8 g, at least about or less than about 2 g, at least about or less than about 2.2 g, at least about or less than about 2.4 g, at least about or less than about 2.6 g, at least about or less than about 2.8 g, at least about or less than about 3 g, at least about or less than about 3.2 g, at least about or less than about 3.4 g, at least about or less than about 3.6 g, at least about or less than about 3.8 g, at least about or less than about 4 g, at least about or less than about 4.2 g, at least about or less than about 4.4 g, at least about or less than about 4.6 g, at least about or less than about 4.8 g, at least about or less than about 5 g, at least about or less than about 5.2 g, at least about or less than about 5.4 g, at least about or less than about 5.6 g, at least about or less than about 5.8 g, or at least about or less than about 6 g of at least one bile acid sequestrant. In certain embodiments, the dosage unit comprises at least about or less than about 95 mg of at least one proton pump inhibitor and at least about or less than about 0.2 g, at least about or less than about 0.4 g, at least about or less than about 0.6 g, at least about or less than about 0.8 g, at least about or less than about 1 g, at least about or less than about 1.2 g, at least about or less than about 1.4 g, at least about or less than about 1.6 g, at least about or less than about 1.8 g, at least about or less than about 2 g, at least about or less than about 2.2 g, at least about or less than about 2.4 g, at least about or less than about 2.6 g, at least about or less than about 2.8 g, at least about or less than about 3 g, at least about or less than about 3.2 g, at least about or less than about 3.4 g, at least about or less than about 3.6 g, at least about or less than about 3.8 g, at least about or less than about 4 g, at least about or less than about 4.2 g, at least about or less than about 4.4 g, at least about or less than about 4.6 g, at least about or less than about 4.8 g, at least about or less than about 5 g, at least about or less than about 5.2 g, at least about or less than about 5.4 g, at least about or less than about 5.6 g, at least about or less than about 5.8 g, or at least about or less than about 6 g of at least one bile acid sequestrant. In certain embodiments, the dosage unit comprises at least about or less than about 100 mg of at least one proton pump inhibitor and at least about or less than about 0.2 g, at least about or less than about 0.4 g, at least about or less than about 0.6 g, at least about or less than about 0.8 g, at least about or less than about 1 g, at least about or less than about 1.2 g, at least about or less than about 1.4 g, at least about or less than about 1.6 g, at least about or less than about 1.8 g, at least about or less than about 2 g, at least about or less than about 2.2 g, at least about or less than about 2.4 g, at least about or less than about 2.6 g, at least about or less than about 2.8 g, at least about or less than about 3 g, at least about or less than about 3.2 g, at least about or less than about 3.4 g, at least about or less than about 3.6 g, at least about or less than about 3.8 g, at least about or less than about 4 g, at least about or less than about 4.2 g, at least about or less than about 4.4 g, at least about or less than about 4.6 g, at least about or less than about 4.8 g, at least about or less than about 5 g, at least about or less than about 5.2 g, at least about or less than about 5.4 g, at least about or less than about 5.6 g, at least about or less than about 5.8 g, or at least about or less than about 6 g of at least one bile acid sequestrant. In certain embodiments the at least one proton pump inhibitor is omeprazole. In certain embodiments the at least one proton pump inhibitor is esomeprazole. In certain embodiments the at least one proton pump inhibitor is lansoprazole. In certain embodiments the at least one proton pump inhibitor is pantoprazole. In certain embodiments the at least one proton pump inhibitor is rabeprazole. In certain embodiments the at least one proton pump inhibitor is tenatoprazole. In certain embodiments the at least one bile acid sequestrant is cholestyramine. In certain embodiments the at least one bile acid sequestrant is colesevelam. In certain embodiments the at least one bile acid sequestrant is colesevelam-HCl. In certain embodiments the at least one bile acid sequestrant is colestipol. In certain embodiments the at least one proton pump inhibitor is omeprazole and the at least one bile acid sequestrant is cholestyramine. In certain embodiments the at least one proton pump inhibitor is omeprazole and the at least one bile acid sequestrant is colesevelam. In certain embodiments the at least one proton pump inhibitor is omeprazole and the at least one bile acid sequestrant is colesevelam-HCl. In certain embodiments the at least one proton pump inhibitor is omeprazole and the at least one bile acid sequestrant is colestipol. In certain embodiments the at least one proton pump inhibitor is esomeprazole and the at least one bile acid sequestrant is cholestyramine. In certain embodiments the at least one proton pump inhibitor is esomeprazole and the at least one bile acid sequestrant is colesevelam. In certain embodiments the at least one proton pump inhibitor is esomeprazole and the at least one bile acid sequestrant is colesevelam-HCl. In certain embodiments the at least one proton pump inhibitor is esomeprazole and the at least one bile acid sequestrant is colestipol. In certain embodiments the at least one proton pump inhibitor is lansoprazole and the at least one bile acid sequestrant is cholestyramine. In certain embodiments the at least one proton pump inhibitor is lansoprazole and the at least one bile acid sequestrant is colesevelam. In certain embodiments the at least one proton pump inhibitor is lansoprazole and the at least one bile acid sequestrant is colesevelam-HCl. In certain embodiments the at least one proton pump inhibitor is lansoprazole and the at least one bile acid sequestrant is colestipol. In certain embodiments the at least one proton pump inhibitor is pantoprazole and the at least one bile acid sequestrant is cholestyramine. In certain embodiments the at least one proton pump inhibitor is pantoprazole and the at least one bile acid sequestrant is colesevelam. In certain embodiments the at least one proton pump inhibitor is pantoprazole and the at least one bile acid sequestrant is colesevelam-HCl. In certain embodiments the at least one proton pump inhibitor is pantoprazole and the at least one bile acid sequestrant is colestipol. In certain embodiments the at least one proton pump inhibitor is rabeprazole and the at least one bile acid sequestrant is cholestyramine. In certain embodiments the at least one proton pump inhibitor is rabeprazole and the at least one bile acid sequestrant is colesevelam. In certain embodiments the at least one proton pump inhibitor is rabeprazole and the at least one bile acid sequestrant is colesevelam-HCl. In certain embodiments the at least one proton pump inhibitor is rabeprazole and the at least one bile acid sequestrant is colestipol. In certain embodiments the at least one proton pump inhibitor is tenatoprazole and the at least one bile acid sequestrant is cholestyramine. In certain embodiments the at least one proton pump inhibitor is tenatoprazole and the at least one bile acid sequestrant is colesevelam. In certain embodiments the at least one proton pump inhibitor is tenatoprazole and the at least one bile acid sequestrant is colesevelam-HCl. In certain embodiments the at least one proton pump inhibitor is tenatoprazole and the at least one bile acid sequestrant is colestipol. In certain embodiments the dosage unit and daily dose are equivalent. In various embodiments, the dosage unit is administered with food at anytime of the day, without food at anytime of the day, with food after an overnight fast (e.g. with breakfast), at bedtime after a low fat snack. In various embodiments, the dosage unit is administered once a day, twice a day, three times a day, four times a day. The dosage unit can optionally comprise other agents such as at least one antacid, at least one histamine $H_2$-receptor antagonist, or combinations thereof.

In certain embodiments, the dosage unit comprises at least about or less than about 5 mg of at least one proton pump inhibitor and at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, or at least about or less than about 3 g of at least one bile acid sequestrant. In certain embodiments, the dosage unit comprises at least about or less than about 10 mg of at least one proton pump inhibitor and at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, or at least about or less than about 3 g of at least one bile acid sequestrant. In certain embodiments, the dosage unit comprises at least about or less than about 5 mg of at least one proton pump inhibitor and at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, or at least about or less than about 3 g of at least one bile acid sequestrant. In certain embodiments, the dosage unit comprises at least about or less than about 15 mg of at least one proton pump inhibitor and at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, or at least about or less than about 3 g of at least one bile acid sequestrant. In certain embodiments, the dosage unit comprises at least about or less than about 20 mg of at least one proton pump inhibitor and at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, or at least about or less than about 3 g of at least one bile acid sequestrant. In certain embodiments, the dosage unit comprises at least about or less than about 25 mg of at least one proton pump inhibitor and at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, or at least about or less than about 3 g of at least one bile acid sequestrant. In certain embodiments, the dosage unit comprises at least about or less than about 30 mg of at least one proton pump inhibitor and at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, or at least about or less than about 3 g of at least one bile acid sequestrant. In certain embodiments, the dosage unit comprises at least about or less than about 35 mg of at least one proton pump inhibitor and at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, or at least about or less than about 3 g of at least one bile acid sequestrant. In certain embodiments, the dosage unit comprises at least about or less than about 40 mg of at least one proton pump inhibitor and at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, or at least about or less than about 3 g of at least one bile acid sequestrant. In certain embodiments, the dosage unit comprises at least about or less than about 45 mg of at least one proton pump inhibitor and at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, or at least about or less than about 3 g of at least one bile acid sequestrant. In certain embodiments, the dosage unit comprises at least about or less than about 50 mg of at least one proton pump inhibitor and at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, or at least about or less than about 3 g of at least one bile acid sequestrant. In certain embodiments, the dosage unit comprises at least about or less than about 55 mg of at least one proton pump inhibitor and at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, or at least about or less than about 3 g of at least one bile acid sequestrant. In certain embodiments, the dosage unit comprises at least about or less than about 60 mg of at least one proton pump inhibitor and at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, or at least about or less than about 3 g of at least one bile acid sequestrant. In certain embodiments, the dosage unit comprises at least about or less than about 65 mg of at least one proton pump inhibitor and at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, or at least about or less than about 3 g of at least one bile acid sequestrant. In certain embodiments, the dosage unit comprises at least about or less than about 70 mg of at least one proton pump inhibitor and at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, or at least about or less than about 3 g of at least one bile acid sequestrant. In certain embodiments, the dosage unit comprises at least about or less than about 75 mg of at least one proton pump inhibitor and at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, or at least about or less than about 3 g of at least one bile acid sequestrant. In certain embodiments, the dosage unit comprises at least about or less than about 80 mg of at least one proton pump inhibitor and at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, or at least about or less than about 3 g of at least one bile acid sequestrant. In certain embodiments, the dosage unit comprises at least about or less than about 85 mg of at least one proton pump inhibitor and at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, or at least about or less than about 3 g of at least one bile acid sequestrant. In certain embodiments, the dosage unit comprises at least about or less than about 90 mg of at least one proton pump inhibitor and at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, or at least about or less than about 3 g of at least one bile acid sequestrant. In certain embodiments, the dosage unit comprises at least about or less than about 95 mg of at least one proton pump inhibitor and at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, or at least about or less than about 3 g of at least one bile acid sequestrant. In certain embodiments, the dosage unit comprises at least about or less than about 100 mg of at least one proton pump inhibitor and at least about or less than about 0.1 g, at least about or less than about 0.2 g, at least about or less than about 0.3 g, at least about or less than about 0.4 g, at least about or less than about 0.5 g, at least about or less than about 0.6 g, at least about or less than about 0.7 g, at least about or less than about 0.8 g, at least about or less than about 0.9 g, at least about or less than about 1 g, at least about or less than about 1.1 g, at least about or less than about 1.2 g, at least about or less than about 1.3 g, at least about or less than about 1.4 g, at least about or less than about 1.5 g, at least about or less than about 1.6 g, at least about or less than about 1.7 g, at least about or less than about 1.8 g, at least about or less than about 1.9 g, at least about or less than about 2 g, at least about or less than about 2.1 g, at least about or less than about 2.2 g, at least about or less than about 2.3 g, at least about or less than about 2.4 g, at least about or less than about 2.5 g, at least about or less than about 2.6 g, at least about or less than about 2.7 g, at least about or less than about 2.8 g, at least about or less than about 2.9 g, or at least about or less than about 3 g of at least one bile acid sequestrant. In certain embodiments the at least one proton pump inhibitor is omeprazole. In certain embodiments the at least one proton pump inhibitor is esomeprazole. In certain embodiments the at least one proton pump inhibitor is lansoprazole. In certain embodiments the at least one proton pump inhibitor is pantoprazole. In certain embodiments the at least one proton pump inhibitor is rabeprazole. In certain embodiments the at least one proton pump inhibitor is tenatoprazole. In certain embodiments the at least one bile acid sequestrant is cholestyramine. In certain embodiments the at least one bile acid sequestrant is colesevelam. In certain embodiments the at least one bile acid sequestrant is colesevelam-HCl. In certain embodiments the at least one bile acid sequestrant is colestipol. In certain embodiments the at least one proton pump inhibitor is omeprazole and the at least one bile acid sequestrant is cholestyramine. In certain embodiments the at least one proton pump inhibitor is omeprazole and the at least one bile acid sequestrant is colesevelam. In certain embodiments the at least one proton pump inhibitor is omeprazole and the at least one bile acid sequestrant is colesevelam-HCl. In certain embodiments the at least one proton pump inhibitor is omeprazole and the at least one bile acid sequestrant is colestipol. In certain embodiments the at least one proton pump inhibitor is esomeprazole and the at least one bile acid sequestrant is cholestyramine. In certain embodiments the at least one proton pump inhibitor is esomeprazole and the at least one bile acid sequestrant is colesevelam. In certain embodiments the at least one proton pump inhibitor is esomeprazole and the at least one bile acid sequestrant is colesevelam-HCl. In certain embodiments the at least one proton pump inhibitor is esomeprazole and the at least one bile acid sequestrant is colestipol. In certain embodiments the at least one proton pump inhibitor is lansoprazole and the at least one bile acid sequestrant is cholestyramine. In certain embodiments the at least one proton pump inhibitor is lansoprazole and the at least one bile acid sequestrant is colesevelam. In certain embodiments the at least one proton pump inhibitor is lansoprazole and the at least one bile acid sequestrant is colesevelam-HCl. In certain embodiments the at least one proton pump inhibitor is lansoprazole and the at least one bile acid sequestrant is colestipol. In certain embodiments the at least one proton pump inhibitor is pantoprazole and the at least one bile acid sequestrant is cholestyramine. In certain embodiments the at least one proton pump inhibitor is pantoprazole and the at least one bile acid sequestrant is colesevelam. In certain embodiments the at least one proton pump inhibitor is pantoprazole and the at least one bile acid sequestrant is colesevelam-HCl. In certain embodiments the at least one proton pump inhibitor is pantoprazole and the at least one bile acid sequestrant is colestipol. In certain embodiments the at least one proton pump inhibitor is rabeprazole and the at least one bile acid sequestrant is cholestyramine. In certain embodiments the at least one proton pump inhibitor is rabeprazole and the at least one bile acid sequestrant is colesevelam. In certain embodiments the at least one proton pump inhibitor is rabeprazole and the at least one bile acid sequestrant is colesevelam-HCl. In certain embodiments the at least one proton pump inhibitor is rabeprazole and the at least one bile acid sequestrant is colestipol. In certain embodiments the at least one proton pump inhibitor is tenatoprazole and the at least one bile acid sequestrant is cholestyramine. In certain embodiments the at least one proton pump inhibitor is tenatoprazole and the at least one bile acid sequestrant is colesevelam. In certain embodiments the at least one proton pump inhibitor is tenatoprazole and the at least one bile acid sequestrant is colesevelam-HCl. In certain embodiments the at least one proton pump inhibitor is tenatoprazole and the at least one bile acid sequestrant is colestipol. In certain embodiments the dosage unit and daily dose are equivalent. In various embodiments, the dosage unit is administered with food at anytime of the day, without food at anytime of the day, with food after an overnight fast (e.g. with breakfast), at bedtime after a low fat snack. In various embodiments, the dosage unit is administered once a day, twice a day, three times a day, four times a day. The dosage unit can optionally comprise other agents such as at least one antacid, at least one histamine H$_2$-receptor antagonist, or combinations thereof.

In certain embodiments, the dosage unit comprises at least about or less than about 5 mg of at least one proton pump inhibitor and at least about or less than about 0.02 g, at least about or less than about 0.04 g, at least about or less than about 0.06 g, at least about or less than about 0.08 g, at least about or less than about 0.1 g, at least about or less than about 0.12 g, at least about or less than about 0.14 g, at least about or less than about 0.16 g, at least about or less than about 0.18 g, at least about or less than about 0.2 g, at least about or less than about 0.22 g, at least about or less than about 0.24 g, at least about or less than about 0.26 g, at least about or less than about 0.28 g, at least about or less than about 0.3 g, at least about or less than about 0.32 g, at least about or less than about 0.34 g, at least about or less than about 0.36 g, at least about or less than about 0.38 g, at least about or less than about 0.4 g, at least about or less than about 0.42 g, at least about or less than about 0.44 g, at least about or less than about 0.46 g, at least about or less than about 0.48 g, at least about or less than about 0.5 g, at least about or less than about 0.52 g, at least about or less than about 0.54 g, at least about or less than about 0.56 g, at least about or less than about 0.58 g, or at least about or less than about 0.6 g of at least one bile acid sequestrant. In certain embodiments, the dosage unit comprises at least about or less than about 10 mg of at least one proton pump inhibitor and at least about or less than about 0.02 g, at least about or less than about 0.04 g, at least about or less than about 0.06 g, at least about or less than about 0.08 g, at least about or less than about 0.1 g, at least about or less than about 0.12 g, at least about or less than about 0.14 g, at least about or less than about 0.16 g, at least about or less than about 0.18 g, at least about or less than about 0.2 g, at least about or less than about 0.22 g, at least about or less than about 0.24 g, at least about or less than about 0.26 g, at least about or less than about 0.28 g, at least about or less than about 0.3 g, at least about or less than about 0.32 g, at least about or less than about 0.34 g, at least about or less than about 0.36 g, at least about or less than about 0.38 g, at least about or less than about 0.4 g, at least about or less than about 0.42 g, at least about or less than about 0.44 g, at least about or less than about 0.46 g, at least about or less than about 0.48 g, at least about or less than about 0.5 g, at least about or less than about 0.52 g, at least about or less than about 0.54 g, at least about or less than about 0.56 g, at least about or less than about 0.58 g, or at least about or less than about 0.6 g of at least one bile acid sequestrant. In certain embodiments, the dosage unit comprises at least about or less than about 15 mg of at least one proton pump inhibitor and at least about or less than about 0.02 g, at least about or less than about 0.04 g, at least about or less than about 0.06 g, at least about or less than about 0.08 g, at least about or less than about 0.1 g, at least about or less than about 0.12 g, at least about or less than about 0.14 g, at least about or less than about 0.16 g, at least about or less than about 0.18 g, at least about or less than about 0.2 g, at least about or less than about 0.22 g, at least about or less than about 0.24 g, at least about or less than about 0.26 g, at least about or less than about 0.28 g, at least about or less than about 0.3 g, at least about or less than about 0.32 g, at least about or less than about 0.34 g, at least about or less than about 0.36 g, at least about or less than about 0.38 g, at least about or less than about 0.4 g, at least about or less than about 0.42 g, at least about or less than about 0.44 g, at least about or less than about 0.46 g, at least about or less than about 0.48 g, at least about or less than about 0.5 g, at least about or less than about 0.52 g, at least about or less than about 0.54 g, at least about or less than about 0.56 g, at least about or less than about 0.58 g, or at least about or less than about 0.6 g of at least one bile acid sequestrant. In certain embodiments, the dosage unit comprises at least about or less than about 20 mg of at least one proton pump inhibitor and at least about or less than about 0.02 g, at least about or less than about 0.04 g, at least about or less than about 0.06 g, at least about or less than about 0.08 g, at least about or less than about 0.1 g, at least about or less than about 0.12 g, at least about or less than about 0.14 g, at least about or less than about 0.16 g, at least about or less than about 0.18 g, at least about or less than about 0.2 g, at least about or less than about 0.22 g, at least about or less than about 0.24 g, at least about or less than about 0.26 g, at least about or less than about 0.28 g, at least about or less than about 0.3 g, at least about or less than about 0.32 g, at least about or less than about 0.34 g, at least about or less than about 0.36 g, at least about or less than about 0.38 g, at least about or less than about 0.4 g, at least about or less than about 0.42 g, at least about or less than about 0.44 g, at least about or less than about 0.46 g, at least about or less than about 0.48 g, at least about or less than about 0.5 g, at least about or less than about 0.52 g, at least about or less than about 0.54 g, at least about or less than about 0.56 g, at least about or less than about 0.58 g, or at least about or less than about 0.6 g of at least one bile acid sequestrant. In certain embodiments, the dosage unit comprises at least about or less than about 25 mg of at least one proton pump inhibitor and at least about or less than about 0.02 g, at least about or less than about 0.04 g, at least about or less than about 0.06 g, at least about or less than about 0.08 g, at least about or less than about 0.1 g, at least about or less than about 0.12 g, at least about or less than about 0.14 g, at least about or less than about 0.16 g, at least about or less than about 0.18 g, at least about or less than about 0.2 g, at least about or less than about 0.22 g, at least about or less than about 0.24 g, at least about or less than about 0.26 g, at least about or less than about 0.28 g, at least about or less than about 0.3 g, at least about or less than about 0.32 g, at least about or less than about 0.34 g, at least about or less than about 0.36 g, at least about or less than about 0.38 g, at least about or less than about 0.4 g, at least about or less than about 0.42 g, at least about or less than about 0.44 g, at least about or less than about 0.46 g, at least about or less than about 0.48 g, at least about or less than about 0.5 g, at least about or less than about 0.52 g, at least about or less than about 0.54 g, at least about or less than about 0.56 g, at least about or less than about 0.58 g, or at least about or less than about 0.6 g of at least one bile acid sequestrant. In certain embodiments, the dosage unit comprises at least about or less than about 30 mg of at least one proton pump inhibitor and at least about or less than about 0.02 g, at least about or less than about 0.04 g, at least about or less than about 0.06 g, at least about or less than about 0.08 g, at least about or less than about 0.1 g, at least about or less than about 0.12 g, at least about or less than about 0.14 g, at least about or less than about 0.16 g, at least about or less than about 0.18 g, at least about or less than about 0.2 g, at least about or less than about 0.22 g, at least about or less than about 0.24 g, at least about or less than about 0.26 g, at least about or less than about 0.28 g, at least about or less than about 0.3 g, at least about or less than about 0.32 g, at least about or less than about 0.34 g, at least about or less than about 0.36 g, at least about or less than about 0.38 g, at least about or less than about 0.4 g, at least about or less than about 0.42 g, at least about or less than about 0.44 g, at least about or less than about 0.46 g, at least about or less than about 0.48 g, at least about or less than about 0.5 g, at least about or less than about 0.52 g, at least about or less than about 0.54 g, at least about or less than about 0.56 g, at least about or less than about 0.58 g, or at least about or less than about 0.6 g of at least one bile acid sequestrant. In certain embodiments, the dosage unit comprises at least about or less than about 35 mg of at least one proton pump inhibitor and at least about or less than about 0.02 g, at least about or less than about 0.04 g, at least about or less than about 0.06 g, at least about or less than about 0.08 g, at least about or less than about 0.1 g, at least about or less than about 0.12 g, at least about or less than about 0.14 g, at least about or less than about 0.16 g, at least about or less than about 0.18 g, at least about or less than about 0.2 g, at least about or less than about 0.22 g, at least about or less than about 0.24 g, at least about or less than about 0.26 g, at least about or less than about 0.28 g, at least about or less than about 0.3 g, at least about or less than about 0.32 g, at least about or less than about 0.34 g, at least about or less than about 0.36 g, at least about or less than about 0.38 g, at least about or less than about 0.4 g, at least about or less than about 0.42 g, at least about or less than about 0.44 g, at least about or less than about 0.46 g, at least about or less than about 0.48 g, at least about or less than about 0.5 g, at least about or less than about 0.52 g, at least about or less than about 0.54 g, at least about or less than about 0.56 g, at least about or less than about 0.58 g, or at least about or less than about 0.6 g of at least one bile acid sequestrant. In certain embodiments, the dosage unit comprises at least about or less than about 40 mg of at least one proton pump inhibitor and at least about or less than about 0.02 g, at least about or less than about 0.04 g, at least about or less than about 0.06 g, at least about or less than about 0.08 g, at least about or less than about 0.1 g, at least about or less than about 0.12 g, at least about or less than about 0.14 g, at least about or less than about 0.16 g, at least about or less than about 0.18 g, at least about or less than about 0.2 g, at least about or less than about 0.22 g, at least about or less than about 0.24 g, at least about or less than about 0.26 g, at least about or less than about 0.28 g, at least about or less than about 0.3 g, at least about or less than about 0.32 g, at least about or less than about 0.34 g, at least about or less than about 0.36 g, at least about or less than about 0.38 g, at least about or less than about 0.4 g, at least about or less than about 0.42 g, at least about or less than about 0.44 g, at least about or less than about 0.46 g, at least about or less than about 0.48 g, at least about or less than about 0.5 g, at least about or less than about 0.52 g, at least about or less than about 0.54 g, at least about or less than about 0.56 g, at least about or less than about 0.58 g, or at least about or less than about 0.6 g of at least one bile acid sequestrant. In certain embodiments, the dosage unit comprises at least about or less than about 45 mg of at least one proton pump inhibitor and at least about or less than about 0.02 g, at least about or less than about 0.04 g, at least about or less than about 0.06 g, at least about or less than about 0.08 g, at least about or less than about 0.1 g, at least about or less than about 0.12 g, at least about or less than about 0.14 g, at least about or less than about 0.16 g, at least about or less than about 0.18 g, at least about or less than about 0.2 g, at least about or less than about 0.22 g, at least about or less than about 0.24 g, at least about or less than about 0.26 g, at least about or less than about 0.28 g, at least about or less than about 0.3 g, at least about or less than about 0.32 g, at least about or less than about 0.34 g, at least about or less than about 0.36 g, at least about or less than about 0.38 g, at least about or less than about 0.4 g, at least about or less than about 0.42 g, at least about or less than about 0.44 g, at least about or less than about 0.46 g, at least about or less than about 0.48 g, at least about or less than about 0.5 g, at least about or less than about 0.52 g, at least about or less than about 0.54 g, at least about or less than about 0.56 g, at least about or less than about 0.58 g, or at least about or less than about 0.6 g of at least one bile acid sequestrant. In certain embodiments, the dosage unit comprises at least about or less than about 50 mg of at least one proton pump inhibitor and at least about or less than about 0.02 g, at least about or less than about 0.04 g, at least about or less than about 0.06 g, at least about or less than about 0.08 g, at least about or less than about 0.1 g, at least about or less than about 0.12 g, at least about or less than about 0.14 g, at least about or less than about 0.16 g, at least about or less than about 0.18 g, at least about or less than about 0.2 g, at least about or less than about 0.22 g, at least about or less than about 0.24 g, at least about or less than about 0.26 g, at least about or less than about 0.28 g, at least about or less than about 0.3 g, at least about or less than about 0.32 g, at least about or less than about 0.34 g, at least about or less than about 0.36 g, at least about or less than about 0.38 g, at least about or less than about 0.4 g, at least about or less than about 0.42 g, at least about or less than about 0.44 g, at least about or less than about 0.46 g, at least about or less than about 0.48 g, at least about or less than about 0.5 g, at least about or less than about 0.52 g, at least about or less than about 0.54 g, at least about or less than about 0.56 g, at least about or less than about 0.58 g, or at least about or less than about 0.6 g of at least one bile acid sequestrant. In certain embodiments, the dosage unit comprises at least about or less than about 55 mg of at least one proton pump inhibitor and at least about or less than about 0.02 g, at least about or less than about 0.04 g, at least about or less than about 0.06 g, at least about or less than about 0.08 g, at least about or less than about 0.1 g, at least about or less than about 0.12 g, at least about or less than about 0.14 g, at least about or less than about 0.16 g, at least about or less than about 0.18 g, at least about or less than about 0.2 g, at least about or less than about 0.22 g, at least about or less than about 0.24 g, at least about or less than about 0.26 g, at least about or less than about 0.28 g, at least about or less than about 0.3 g, at least about or less than about 0.32 g, at least about or less than about 0.34 g, at least about or less than about 0.36 g, at least about or less than about 0.38 g, at least about or less than about 0.4 g, at least about or less than about 0.42 g, at least about or less than about 0.44 g, at least about or less than about 0.46 g, at least about or less than about 0.48 g, at least about or less than about 0.5 g, at least about or less than about 0.52 g, at least about or less than about 0.54 g, at least about or less than about 0.56 g, at least about or less than about 0.58 g, or at least about or less than about 0.6 g of at least one bile acid sequestrant. In certain embodiments, the dosage unit comprises at least about or less than about 60 mg of at least one proton pump inhibitor and at least about or less than about 0.02 g, at least about or less than about 0.04 g, at least about or less than about 0.06 g, at least about or less than about 0.08 g, at least about or less than about 0.1 g, at least about or less than about 0.12 g, at least about or less than about 0.14 g, at least about or less than about 0.16 g, at least about or less than about 0.18 g, at least about or less than about 0.2 g, at least about or less than about 0.22 g, at least about or less than about 0.24 g, at least about or less than about 0.26 g, at least about or less than about 0.28 g, at least about or less than about 0.3 g, at least about or less than about 0.32 g, at least about or less than about 0.34 g, at least about or less than about 0.36 g, at least about or less than about 0.38 g, at least about or less than about 0.4 g, at least about or less than about 0.42 g, at least about or less than about 0.44 g, at least about or less than about 0.46 g, at least about or less than about 0.48 g, at least about or less than about 0.5 g, at least about or less than about 0.52 g, at least about or less than about 0.54 g, at least about or less than about 0.56 g, at least about or less than about 0.58 g, or at least about or less than about 0.6 g of at least one bile acid sequestrant. In certain embodiments, the dosage unit comprises at least about or less than about 65 mg of at least one proton pump inhibitor and at least about or less than about 0.02 g, at least about or less than about 0.04 g, at least about or less than about 0.06 g, at least about or less than about 0.08 g, at least about or less than about 0.1 g, at least about or less than about 0.12 g, at least about or less than about 0.14 g, at least about or less than about 0.16 g, at least about or less than about 0.18 g, at least about or less than about 0.2 g, at least about or less than about 0.22 g, at least about or less than about 0.24 g, at least about or less than about 0.26 g, at least about or less than about 0.28 g, at least about or less than about 0.3 g, at least about or less than about 0.32 g, at least about or less than about 0.34 g, at least about or less than about 0.36 g, at least about or less than about 0.38 g, at least about or less than about 0.4 g, at least about or less than about 0.42 g, at least about or less than about 0.44 g, at least about or less than about 0.46 g, at least about or less than about 0.48 g, at least about or less than about 0.5 g, at least about or less than about 0.52 g, at least about or less than about 0.54 g, at least about or less than about 0.56 g, at least about or less than about 0.58 g, or at least about or less than about 0.6 g of at least one bile acid sequestrant. In certain embodiments, the dosage unit comprises at least about or less than about 70 mg of at least one proton pump inhibitor and at least about or less than about 0.02 g, at least about or less than about 0.04 g, at least about or less than about 0.06 g, at least about or less than about 0.08 g, at least about or less than about 0.1 g, at least about or less than about 0.12 g, at least about or less than about 0.14 g, at least about or less than about 0.16 g, at least about or less than about 0.18 g, at least about or less than about 0.2 g, at least about or less than about 0.22 g, at least about or less than about 0.24 g, at least about or less than about 0.26 g, at least about or less than about 0.28 g, at least about or less than about 0.3 g, at least about or less than about 0.32 g, at least about or less than about 0.34 g, at least about or less than about 0.36 g, at least about or less than about 0.38 g, at least about or less than about 0.4 g, at least about or less than about 0.42 g, at least about or less than about 0.44 g, at least about or less than about 0.46 g, at least about or less than about 0.48 g, at least about or less than about 0.5 g, at least about or less than about 0.52 g, at least about or less than about 0.54 g, at least about or less than about 0.56 g, at least about or less than about 0.58 g, or at least about or less than about 0.6 g of at least one bile acid sequestrant. In certain embodiments, the dosage unit comprises at least about or less than about 75 mg of at least one proton pump inhibitor and at least about or less than about 0.02 g, at least about or less than about 0.04 g, at least about or less than about 0.06 g, at least about or less than about 0.08 g, at least about or less than about 0.1 g, at least about or less than about 0.12 g, at least about or less than about 0.14 g, at least about or less than about 0.16 g, at least about or less than about 0.18 g, at least about or less than about 0.2 g, at least about or less than about 0.22 g, at least about or less than about 0.24 g, at least about or less than about 0.26 g, at least about or less than about 0.28 g, at least about or less than about 0.3 g, at least about or less than about 0.32 g, at least about or less than about 0.34 g, at least about or less than about 0.36 g, at least about or less than about 0.38 g, at least about or less than about 0.4 g, at least about or less than about 0.42 g, at least about or less than about 0.44 g, at least about or less than about 0.46 g, at least about or less than about 0.48 g, at least about or less than about 0.5 g, at least about or less than about 0.52 g, at least about or less than about 0.54 g, at least about or less than about 0.56 g, at least about or less than about 0.58 g, or at least about or less than about 0.6 g of at least one bile acid sequestrant. In certain embodiments, the dosage unit comprises at least about or less than about 80 mg of at least one proton pump inhibitor and at least about or less than about 0.02 g, at least about or less than about 0.04 g, at least about or less than about 0.06 g, at least about or less than about 0.08 g, at least about or less than about 0.1 g, at least about or less than about 0.12 g, at least about or less than about 0.14 g, at least about or less than about 0.16 g, at least about or less than about 0.18 g, at least about or less than about 0.2 g, at least about or less than about 0.22 g, at least about or less than about 0.24 g, at least about or less than about 0.26 g, at least about or less than about 0.28 g, at least about or less than about 0.3 g, at least about or less than about 0.32 g, at least about or less than about 0.34 g, at least about or less than about 0.36 g, at least about or less than about 0.38 g, at least about or less than about 0.4 g, at least about or less than about 0.42 g, at least about or less than about 0.44 g, at least about or less than about 0.46 g, at least about or less than about 0.48 g, at least about or less than about 0.5 g, at least about or less than about 0.52 g, at least about or less than about 0.54 g, at least about or less than about 0.56 g, at least about or less than about 0.58 g, or at least about or less than about 0.6 g of at least one bile acid sequestrant. In certain embodiments, the dosage unit comprises at least about or less than about 85 mg of at least one proton pump inhibitor and at least about or less than about 0.02 g, at least about or less than about 0.04 g, at least about or less than about 0.06 g, at least about or less than about 0.08 g, at least about or less than about 0.1 g, at least about or less than about 0.12 g, at least about or less than about 0.14 g, at least about or less than about 0.16 g, at least about or less than about 0.18 g, at least about or less than about 0.2 g, at least about or less than about 0.22 g, at least about or less than about 0.24 g, at least about or less than about 0.26 g, at least about or less than about 0.28 g, at least about or less than about 0.3 g, at least about or less than about 0.32 g, at least about or less than about 0.34 g, at least about or less than about 0.36 g, at least about or less than about 0.38 g, at least about or less than about 0.4 g, at least about or less than about 0.42 g, at least about or less than about 0.44 g, at least about or less than about 0.46 g, at least about or less than about 0.48 g, at least about or less than about 0.5 g, at least about or less than about 0.52 g, at least about or less than about 0.54 g, at least about or less than about 0.56 g, at least about or less than about 0.58 g, or at least about or less than about 0.6 g of at least one bile acid sequestrant. In certain embodiments, the dosage unit comprises at least about or less than about 90 mg of at least one proton pump inhibitor and at least about or less than about 0.02 g, at least about or less than about 0.04 g, at least about or less than about 0.06 g, at least about or less than about 0.08 g, at least about or less than about 0.1 g, at least about or less than about 0.12 g, at least about or less than about 0.14 g, at least about or less than about 0.16 g, at least about or less than about 0.18 g, at least about or less than about 0.2 g, at least about or less than about 0.22 g, at least about or less than about 0.24 g, at least about or less than about 0.26 g, at least about or less than about 0.28 g, at least about or less than about 0.3 g, at least about or less than about 0.32 g, at least about or less than about 0.34 g, at least about or less than about 0.36 g, at least about or less than about 0.38 g, at least about or less than about 0.4 g, at least about or less than about 0.42 g, at least about or less than about 0.44 g, at least about or less than about 0.46 g, at least about or less than about 0.48 g, at least about or less than about 0.5 g, at least about or less than about 0.52 g, at least about or less than about 0.54 g, at least about or less than about 0.56 g, at least about or less than about 0.58 g, or at least about or less than about 0.6 g of at least one bile acid sequestrant. In certain embodiments, the dosage unit comprises at least about or less than about 95 mg of at least one proton pump inhibitor and at least about or less than about 0.02 g, at least about or less than about 0.04 g, at least about or less than about 0.06 g, at least about or less than about 0.08 g, at least about or less than about 0.1 g, at least about or less than about 0.12 g, at least about or less than about 0.14 g, at least about or less than about 0.16 g, at least about or less than about 0.18 g, at least about or less than about 0.2 g, at least about or less than about 0.22 g, at least about or less than about 0.24 g, at least about or less than about 0.26 g, at least about or less than about 0.28 g, at least about or less than about 0.3 g, at least about or less than about 0.32 g, at least about or less than about 0.34 g, at least about or less than about 0.36 g, at least about or less than about 0.38 g, at least about or less than about 0.4 g, at least about or less than about 0.42 g, at least about or less than about 0.44 g, at least about or less than about 0.46 g, at least about or less than about 0.48 g, at least about or less than about 0.5 g, at least about or less than about 0.52 g, at least about or less than about 0.54 g, at least about or less than about 0.56 g, at least about or less than about 0.58 g, or at least about or less than about 0.6 g of at least one bile acid sequestrant. In certain embodiments, the dosage unit comprises at least about or less than about 100 mg of at least one proton pump inhibitor and at least about or less than about 0.02 g, at least about or less than about 0.04 g, at least about or less than about 0.06 g, at least about or less than about 0.08 g, at least about or less than about 0.1 g, at least about or less than about 0.12 g, at least about or less than about 0.14 g, at least about or less than about 0.16 g, at least about or less than about 0.18 g, at least about or less than about 0.2 g, at least about or less than about 0.22 g, at least about or less than about 0.24 g, at least about or less than about 0.26 g, at least about or less than about 0.28 g, at least about or less than about 0.3 g, at least about or less than about 0.32 g, at least about or less than about 0.34 g, at least about or less than about 0.36 g, at least about or less than about 0.38 g, at least about or less than about 0.4 g, at least about or less than about 0.42 g, at least about or less than about 0.44 g, at least about or less than about 0.46 g, at least about or less than about 0.48 g, at least about or less than about 0.5 g, at least about or less than about 0.52 g, at least about or less than about 0.54 g, at least about or less than about 0.56 g, at least about or less than about 0.58 g, or at least about or less than about 0.6 g of at least one bile acid sequestrant. In certain embodiments the at least one proton pump inhibitor is omeprazole. In certain embodiments the at least one proton pump inhibitor is esomeprazole. In certain embodiments the at least one proton pump inhibitor is lansoprazole. In certain embodiments the at least one proton pump inhibitor is pantoprazole. In certain embodiments the at least one proton pump inhibitor is rabeprazole. In certain embodiments the at least one proton pump inhibitor is tenatoprazole. In certain embodiments the at least one bile acid sequestrant is cholestyramine. In certain embodiments the at least one bile acid sequestrant is colesevelam. In certain embodiments the at least one bile acid sequestrant is colesevelam-HCl. In certain embodiments the at least one bile acid sequestrant is colestipol. In certain embodiments the at least one proton pump inhibitor is omeprazole and the at least one bile acid sequestrant is cholestyramine. In certain embodiments the at least one proton pump inhibitor is omeprazole and the at least one bile acid sequestrant is colesevelam. In certain embodiments the at least one proton pump inhibitor is omeprazole and the at least one bile acid sequestrant is colesevelam-HCl. In certain embodiments the at least one proton pump inhibitor is omeprazole and the at least one bile acid sequestrant is colestipol. In certain embodiments the at least one proton pump inhibitor is esomeprazole and the at least one bile acid sequestrant is cholestyramine. In certain embodiments the at least one proton pump inhibitor is esomeprazole and the at least one bile acid sequestrant is colesevelam. In certain embodiments the at least one proton pump inhibitor is esomeprazole and the at least one bile acid sequestrant is colesevelam-HCl. In certain embodiments the at least one proton pump inhibitor is esomeprazole and the at least one bile acid sequestrant is colestipol. In certain embodiments the at least one proton pump inhibitor is lansoprazole and the at least one bile acid sequestrant is cholestyramine. In certain embodiments the at least one proton pump inhibitor is lansoprazole and the at least one bile acid sequestrant is colesevelam. In certain embodiments the at least one proton pump inhibitor is lansoprazole and the at least one bile acid sequestrant is colesevelam-HCl. In certain embodiments the at least one proton pump inhibitor is lansoprazole and the at least one bile acid sequestrant is colestipol. In certain embodiments the at least one proton pump inhibitor is pantoprazole and the at least one bile acid sequestrant is cholestyramine. In certain embodiments the at least one proton pump inhibitor is pantoprazole and the at least one bile acid sequestrant is colesevelam. In certain embodiments the at least one proton pump inhibitor is pantoprazole and the at least one bile acid sequestrant is colesevelam-HCl. In certain embodiments the at least one proton pump inhibitor is pantoprazole and the at least one bile acid sequestrant is colestipol. In certain embodiments the at least one proton pump inhibitor is rabeprazole and the at least one bile acid sequestrant is cholestyramine. In certain embodiments the at least one proton pump inhibitor is rabeprazole and the at least one bile acid sequestrant is colesevelam. In certain embodiments the at least one proton pump inhibitor is rabeprazole and the at least one bile acid sequestrant is colesevelam-HCl. In certain embodiments the at least one proton pump inhibitor is rabeprazole and the at least one bile acid sequestrant is colestipol. In certain embodiments the at least one proton pump inhibitor is tenatoprazole and the at least one bile acid sequestrant is cholestyramine. In certain embodiments the at least one proton pump inhibitor is tenatoprazole and the at least one bile acid sequestrant is colesevelam. In certain embodiments the at least one proton pump inhibitor is tenatoprazole and the at least one bile acid sequestrant is colesevelam-HCl. In certain embodiments the at least one proton pump inhibitor is tenatoprazole and the at least one bile acid sequestrant is colestipol. In certain embodiments the dosage unit and daily dose are equivalent. In various embodiments, the dosage unit is administered with food at anytime of the day, without food at anytime of the day, with food after an overnight fast (e.g. with breakfast), at bedtime after a low fat snack. In various embodiments, the dosage unit is administered once a day, twice a day, three times a day, four times a day. The dosage unit can optionally comprise other agents such as at least one antacid, at least one histamine $H_2$-receptor antagonist, or combinations thereof.

In certain embodiments, the dosage unit comprises at least about or less than about 5 mg of at least one proton pump inhibitor and at least about or less than about 0.01 g, at least about or less than about 0.02 g, at least about or less than about 0.03 g, at least about or less than about 0.04 g, at least about or less than about 0.05 g, at least about or less than about 0.06 g, at least about or less than about 0.07 g, at least about or less than about 0.08 g, at least about or less than about 0.09 g, at least about or less than about 0.1 g, at least about or less than about 0.11 g, at least about or less than about 0.12 g, at least about or less than about 0.13 g, at least about or less than about 0.14 g, at least about or less than about 0.15 g, at least about or less than about 0.16 g, at least about or less than about 0.17 g, at least about or less than about 0.18 g, at least about or less than about 0.19 g, at least about or less than about 0.2 g, at least about or less than about 0.21 g, at least about or less than about 0.22 g, at least about or less than about 0.23 g, at least about or less than about 0.24 g, at least about or less than about 0.25 g, at least about or less than about 0.26 g, at least about or less than about 0.27 g, at least about or less than about 0.28 g, at least about or less than about 0.29 g, or at least about or less than about 0.3 g of at least one bile acid sequestrant. In certain embodiments, the dosage unit comprises at least about or less than about 10 mg of at least one proton pump inhibitor and at least about or less than about 0.01 g, at least about or less than about 0.02 g, at least about or less than about 0.03 g, at least about or less than about 0.04 g, at least about or less than about 0.05 g, at least about or less than about 0.06 g, at least about or less than about 0.07 g, at least about or less than about 0.08 g, at least about or less than about 0.09 g, at least about or less than about 0.1 g, at least about or less than about 0.11 g, at least about or less than about 0.12 g, at least about or less than about 0.13 g, at least about or less than about 0.14 g, at least about or less than about 0.15 g, at least about or less than about 0.16 g, at least about or less than about 0.17 g, at least about or less than about 0.18 g, at least about or less than about 0.19 g, at least about or less than about 0.2 g, at least about or less than about 0.21 g, at least about or less than about 0.22 g, at least about or less than about 0.23 g, at least about or less than about 0.24 g, at least about or less than about 0.25 g, at least about or less than about 0.26 g, at least about or less than about 0.27 g, at least about or less than about 0.28 g, at least about or less than about 0.29 g, or at least about or less than about 0.3 g of at least one bile acid sequestrant. In certain embodiments, the dosage unit comprises at least about or less than about 15 mg of at least one proton pump inhibitor and at least about or less than about 0.01 g, at least about or less than about 0.02 g, at least about or less than about 0.03 g, at least about or less than about 0.04 g, at least about or less than about 0.05 g, at least about or less than about 0.06 g, at least about or less than about 0.07 g, at least about or less than about 0.08 g, at least about or less than about 0.09 g, at least about or less than about 0.1 g, at least about or less than about 0.11 g, at least about or less than about 0.12 g, at least about or less than about 0.13 g, at least about or less than about 0.14 g, at least about or less than about 0.15 g, at least about or less than about 0.16 g, at least about or less than about 0.17 g, at least about or less than about 0.18 g, at least about or less than about 0.19 g, at least about or less than about 0.2 g, at least about or less than about 0.21 g, at least about or less than about 0.22 g, at least about or less than about 0.23 g, at least about or less than about 0.24 g, at least about or less than about 0.25 g, at least about or less than about 0.26 g, at least about or less than about 0.27 g, at least about or less than about 0.28 g, at least about or less than about 0.29 g, or at least about or less than about 0.3 g of at least one bile acid sequestrant. In certain embodiments, the dosage unit comprises at least about or less than about 20 mg of at least one proton pump inhibitor and at least about or less than about 0.01 g, at least about or less than about 0.02 g, at least about or less than about 0.03 g, at least about or less than about 0.04 g, at least about or less than about 0.05 g, at least about or less than about 0.06 g, at least about or less than about 0.07 g, at least about or less than about 0.08 g, at least about or less than about 0.09 g, at least about or less than about 0.1 g, at least about or less than about 0.11 g, at least about or less than about 0.12 g, at least about or less than about 0.13 g, at least about or less than about 0.14 g, at least about or less than about 0.15 g, at least about or less than about 0.16 g, at least about or less than about 0.17 g, at least about or less than about 0.18 g, at least about or less than about 0.19 g, at least about or less than about 0.2 g, at least about or less than about 0.21 g, at least about or less than about 0.22 g, at least about or less than about 0.23 g, at least about or less than about 0.24 g, at least about or less than about 0.25 g, at least about or less than about 0.26 g, at least about or less than about 0.27 g, at least about or less than about 0.28 g, at least about or less than about 0.29 g, or at least about or less than about 0.3 g of at least one bile acid sequestrant. In certain embodiments, the dosage unit comprises at least about or less than about 25 mg of at least one proton pump inhibitor and at least about or less than about 0.01 g, at least about or less than about 0.02 g, at least about or less than about 0.03 g, at least about or less than about 0.04 g, at least about or less than about 0.05 g, at least about or less than about 0.06 g, at least about or less than about 0.07 g, at least about or less than about 0.08 g, at least about or less than about 0.09 g, at least about or less than about 0.1 g, at least about or less than about 0.11 g, at least about or less than about 0.12 g, at least about or less than about 0.13 g, at least about or less than about 0.14 g, at least about or less than about 0.15 g, at least about or less than about 0.16 g, at least about or less than about 0.17 g, at least about or less than about 0.18 g, at least about or less than about 0.19 g, at least about or less than about 0.2 g, at least about or less than about 0.21 g, at least about or less than about 0.22 g, at least about or less than about 0.23 g, at least about or less than about 0.24 g, at least about or less than about 0.25 g, at least about or less than about 0.26 g, at least about or less than about 0.27 g, at least about or less than about 0.28 g, at least about or less than about 0.29 g, or at least about or less than about 0.3 g of at least one bile acid sequestrant. In certain embodiments, the dosage unit comprises at least about or less than about 30 mg of at least one proton pump inhibitor and at least about or less than about 0.01 g, at least about or less than about 0.02 g, at least about or less than about 0.03 g, at least about or less than about 0.04 g, at least about or less than about 0.05 g, at least about or less than about 0.06 g, at least about or less than about 0.07 g, at least about or less than about 0.08 g, at least about or less than about 0.09 g, at least about or less than about 0.1 g, at least about or less than about 0.11 g, at least about or less than about 0.12 g, at least about or less than about 0.13 g, at least about or less than about 0.14 g, at least about or less than about 0.15 g, at least about or less than about 0.16 g, at least about or less than about 0.17 g, at least about or less than about 0.18 g, at least about or less than about 0.19 g, at least about or less than about 0.2 g, at least about or less than about 0.21 g, at least about or less than about 0.22 g, at least about or less than about 0.23 g, at least about or less than about 0.24 g, at least about or less than about 0.25 g, at least about or less than about 0.26 g, at least about or less than about 0.27 g, at least about or less than about 0.28 g, at least about or less than about 0.29 g, or at least about or less than about 0.3 g of at least one bile acid sequestrant. In certain embodiments, the dosage unit comprises at least about or less than about 35 mg of at least one proton pump inhibitor and at least about or less than about 0.01 g, at least about or less than about 0.02 g, at least about or less than about 0.03 g, at least about or less than about 0.04 g, at least about or less than about 0.05 g, at least about or less than about 0.06 g, at least about or less than about 0.07 g, at least about or less than about 0.08 g, at least about or less than about 0.09 g, at least about or less than about 0.1 g, at least about or less than about 0.11 g, at least about or less than about 0.12 g, at least about or less than about 0.13 g, at least about or less than about 0.14 g, at least about or less than about 0.15 g, at least about or less than about 0.16 g, at least about or less than about 0.17 g, at least about or less than about 0.18 g, at least about or less than about 0.19 g, at least about or less than about 0.2 g, at least about or less than about 0.21 g, at least about or less than about 0.22 g, at least about or less than about 0.23 g, at least about or less than about 0.24 g, at least about or less than about 0.25 g, at least about or less than about 0.26 g, at least about or less than about 0.27 g, at least about or less than about 0.28 g, at least about or less than about 0.29 g, or at least about or less than about 0.3 g of at least one bile acid sequestrant. In certain embodiments, the dosage unit comprises at least about or less than about 40 mg of at least one proton pump inhibitor and at least about or less than about 0.01 g, at least about or less than about 0.02 g, at least about or less than about 0.03 g, at least about or less than about 0.04 g, at least about or less than about 0.05 g, at least about or less than about 0.06 g, at least about or less than about 0.07 g, at least about or less than about 0.08 g, at least about or less than about 0.09 g, at least about or less than about 0.1 g, at least about or less than about 0.11 g, at least about or less than about 0.12 g, at least about or less than about 0.13 g, at least about or less than about 0.14 g, at least about or less than about 0.15 g, at least about or less than about 0.16 g, at least about or less than about 0.17 g, at least about or less than about 0.18 g, at least about or less than about 0.19 g, at least about or less than about 0.2 g, at least about or less than about 0.21 g, at least about or less than about 0.22 g, at least about or less than about 0.23 g, at least about or less than about 0.24 g, at least about or less than about 0.25 g, at least about or less than about 0.26 g, at least about or less than about 0.27 g, at least about or less than about 0.28 g, at least about or less than about 0.29 g, or at least about or less than about 0.3 g of at least one bile acid sequestrant. In certain embodiments, the dosage unit comprises at least about or less than about 45 mg of at least one proton pump inhibitor and at least about or less than about 0.01 g, at least about or less than about 0.02 g, at least about or less than about 0.03 g, at least about or less than about 0.04 g, at least about or less than about 0.05 g, at least about or less than about 0.06 g, at least about or less than about 0.07 g, at least about or less than about 0.08 g, at least about or less than about 0.09 g, at least about or less than about 0.1 g, at least about or less than about 0.11 g, at least about or less than about 0.12 g, at least about or less than about 0.13 g, at least about or less than about 0.14 g, at least about or less than about 0.15 g, at least about or less than about 0.16 g, at least about or less than about 0.17 g, at least about or less than about 0.18 g, at least about or less than about 0.19 g, at least about or less than about 0.2 g, at least about or less than about 0.21 g, at least about or less than about 0.22 g, at least about or less than about 0.23 g, at least about or less than about 0.24 g, at least about or less than about 0.25 g, at least about or less than about 0.26 g, at least about or less than about 0.27 g, at least about or less than about 0.28 g, at least about or less than about 0.29 g, or at least about or less than about 0.3 g of at least one bile acid sequestrant. In certain embodiments, the dosage unit comprises at least about or less than about 50 mg of at least one proton pump inhibitor and at least about or less than about 0.01 g, at least about or less than about 0.02 g, at least about or less than about 0.03 g, at least about or less than about 0.04 g, at least about or less than about 0.05 g, at least about or less than about 0.06 g, at least about or less than about 0.07 g, at least about or less than about 0.08 g, at least about or less than about 0.09 g, at least about or less than about 0.1 g, at least about or less than about 0.11 g, at least about or less than about 0.12 g, at least about or less than about 0.13 g, at least about or less than about 0.14 g, at least about or less than about 0.15 g, at least about or less than about 0.16 g, at least about or less than about 0.17 g, at least about or less than about 0.18 g, at least about or less than about 0.19 g, at least about or less than about 0.2 g, at least about or less than about 0.21 g, at least about or less than about 0.22 g, at least about or less than about 0.23 g, at least about or less than about 0.24 g, at least about or less than about 0.25 g, at least about or less than about 0.26 g, at least about or less than about 0.27 g, at least about or less than about 0.28 g, at least about or less than about 0.29 g, or at least about or less than about 0.3 g of at least one bile acid sequestrant. In certain embodiments, the dosage unit comprises at least about or less than about 55 mg of at least one proton pump inhibitor and at least about or less than about 0.01 g, at least about or less than about 0.02 g, at least about or less than about 0.03 g, at least about or less than about 0.04 g, at least about or less than about 0.05 g, at least about or less than about 0.06 g, at least about or less than about 0.07 g, at least about or less than about 0.08 g, at least about or less than about 0.09 g, at least about or less than about 0.1 g, at least about or less than about 0.11 g, at least about or less than about 0.12 g, at least about or less than about 0.13 g, at least about or less than about 0.14 g, at least about or less than about 0.15 g, at least about or less than about 0.16 g, at least about or less than about 0.17 g, at least about or less than about 0.18 g, at least about or less than about 0.19 g, at least about or less than about 0.2 g, at least about or less than about 0.21 g, at least about or less than about 0.22 g, at least about or less than about 0.23 g, at least about or less than about 0.24 g, at least about or less than about 0.25 g, at least about or less than about 0.26 g, at least about or less than about 0.27 g, at least about or less than about 0.28 g, at least about or less than about 0.29 g, or at least about or less than about 0.3 g of at least one bile acid sequestrant. In certain embodiments, the dosage unit comprises at least about or less than about 60 mg of at least one proton pump inhibitor and at least about or less than about 0.01 g, at least about or less than about 0.02 g, at least about or less than about 0.03 g, at least about or less than about 0.04 g, at least about or less than about 0.05 g, at least about or less than about 0.06 g, at least about or less than about 0.07 g, at least about or less than about 0.08 g, at least about or less than about 0.09 g, at least about or less than about 0.1 g, at least about or less than about 0.11 g, at least about or less than about 0.12 g, at least about or less than about 0.13 g, at least about or less than about 0.14 g, at least about or less than about 0.15 g, at least about or less than about 0.16 g, at least about or less than about 0.17 g, at least about or less than about 0.18 g, at least about or less than about 0.19 g, at least about or less than about 0.2 g, at least about or less than about 0.21 g, at least about or less than about 0.22 g, at least about or less than about 0.23 g, at least about or less than about 0.24 g, at least about or less than about 0.25 g, at least about or less than about 0.26 g, at least about or less than about 0.27 g, at least about or less than about 0.28 g, at least about or less than about 0.29 g, or at least about or less than about 0.3 g of at least one bile acid sequestrant. In certain embodiments, the dosage unit comprises at least about or less than about 65 mg of at least one proton pump inhibitor and at least about or less than about 0.01 g, at least about or less than about 0.02 g, at least about or less than about 0.03 g, at least about or less than about 0.04 g, at least about or less than about 0.05 g, at least about or less than about 0.06 g, at least about or less than about 0.07 g, at least about or less than about 0.08 g, at least about or less than about 0.09 g, at least about or less than about 0.1 g, at least about or less than about 0.11 g, at least about or less than about 0.12 g, at least about or less than about 0.13 g, at least about or less than about 0.14 g, at least about or less than about 0.15 g, at least about or less than about 0.16 g, at least about or less than about 0.17 g, at least about or less than about 0.18 g, at least about or less than about 0.19 g, at least about or less than about 0.2 g, at least about or less than about 0.21 g, at least about or less than about 0.22 g, at least about or less than about 0.23 g, at least about or less than about 0.24 g, at least about or less than about 0.25 g, at least about or less than about 0.26 g, at least about or less than about 0.27 g, at least about or less than about 0.28 g, at least about or less than about 0.29 g, or at least about or less than about 0.3 g of at least one bile acid sequestrant. In certain embodiments, the dosage unit comprises at least about or less than about 70 mg of at least one proton pump inhibitor and at least about or less than about 0.01 g, at least about or less than about 0.02 g, at least about or less than about 0.03 g, at least about or less than about 0.04 g, at least about or less than about 0.05 g, at least about or less than about 0.06 g, at least about or less than about 0.07 g, at least about or less than about 0.08 g, at least about or less than about 0.09 g, at least about or less than about 0.1 g, at least about or less than about 0.11 g, at least about or less than about 0.12 g, at least about or less than about 0.13 g, at least about or less than about 0.14 g, at least about or less than about 0.15 g, at least about or less than about 0.16 g, at least about or less than about 0.17 g, at least about or less than about 0.18 g, at least about or less than about 0.19 g, at least about or less than about 0.2 g, at least about or less than about 0.21 g, at least about or less than about 0.22 g, at least about or less than about 0.23 g, at least about or less than about 0.24 g, at least about or less than about 0.25 g, at least about or less than about 0.26 g, at least about or less than about 0.27 g, at least about or less than about 0.28 g, at least about or less than about 0.29 g, or at least about or less than about 0.3 g of at least one bile acid sequestrant. In certain embodiments, the dosage unit comprises at least about or less than about 75 mg of at least one proton pump inhibitor and at least about or less than about 0.01 g, at least about or less than about 0.02 g, at least about or less than about 0.03 g, at least about or less than about 0.04 g, at least about or less than about 0.05 g, at least about or less than about 0.06 g, at least about or less than about 0.07 g, at least about or less than about 0.08 g, at least about or less than about 0.09 g, at least about or less than about 0.1 g, at least about or less than about 0.11 g, at least about or less than about 0.12 g, at least about or less than about 0.13 g, at least about or less than about 0.14 g, at least about or less than about 0.15 g, at least about or less than about 0.16 g, at least about or less than about 0.17 g, at least about or less than about 0.18 g, at least about or less than about 0.19 g, at least about or less than about 0.2 g, at least about or less than about 0.21 g, at least about or less than about 0.22 g, at least about or less than about 0.23 g, at least about or less than about 0.24 g, at least about or less than about 0.25 g, at least about or less than about 0.26 g, at least about or less than about 0.27 g, at least about or less than about 0.28 g, at least about or less than about 0.29 g, or at least about or less than about 0.3 g of at least one bile acid sequestrant. In certain embodiments, the dosage unit comprises at least about or less than about 80 mg of at least one proton pump inhibitor and at least about or less than about 0.01 g, at least about or less than about 0.02 g, at least about or less than about 0.03 g, at least about or less than about 0.04 g, at least about or less than about 0.05 g, at least about or less than about 0.06 g, at least about or less than about 0.07 g, at least about or less than about 0.08 g, at least about or less than about 0.09 g, at least about or less than about 0.1 g, at least about or less than about 0.11 g, at least about or less than about 0.12 g, at least about or less than about 0.13 g, at least about or less than about 0.14 g, at least about or less than about 0.15 g, at least about or less than about 0.16 g, at least about or less than about 0.17 g, at least about or less than about 0.18 g, at least about or less than about 0.19 g, at least about or less than about 0.2 g, at least about or less than about 0.21 g, at least about or less than about 0.22 g, at least about or less than about 0.23 g, at least about or less than about 0.24 g, at least about or less than about 0.25 g, at least about or less than about 0.26 g, at least about or less than about 0.27 g, at least about or less than about 0.28 g, at least about or less than about 0.29 g, or at least about or less than about 0.3 g of at least one bile acid sequestrant. In certain embodiments, the dosage unit comprises at least about or less than about 85 mg of at least one proton pump inhibitor and at least about or less than about 0.01 g, at least about or less than about 0.02 g, at least about or less than about 0.03 g, at least about or less than about 0.04 g, at least about or less than about 0.05 g, at least about or less than about 0.06 g, at least about or less than about 0.07 g, at least about or less than about 0.08 g, at least about or less than about 0.09 g, at least about or less than about 0.1 g, at least about or less than about 0.11 g, at least about or less than about 0.12 g, at least about or less than about 0.13 g, at least about or less than about 0.14 g, at least about or less than about 0.15 g, at least about or less than about 0.16 g, at least about or less than about 0.17 g, at least about or less than about 0.18 g, at least about or less than about 0.19 g, at least about or less than about 0.2 g, at least about or less than about 0.21 g, at least about or less than about 0.22 g, at least about or less than about 0.23 g, at least about or less than about 0.24 g, at least about or less than about 0.25 g, at least about or less than about 0.26 g, at least about or less than about 0.27 g, at least about or less than about 0.28 g, at least about or less than about 0.29 g, or at least about or less than about 0.3 g of at least one bile acid sequestrant. In certain embodiments, the dosage unit comprises at least about or less than about 90 mg of at least one proton pump inhibitor and at least about or less than about 0.01 g, at least about or less than about 0.02 g, at least about or less than about 0.03 g, at least about or less than about 0.04 g, at least about or less than about 0.05 g, at least about or less than about 0.06 g, at least about or less than about 0.07 g, at least about or less than about 0.08 g, at least about or less than about 0.09 g, at least about or less than about 0.1 g, at least about or less than about 0.11 g, at least about or less than about 0.12 g, at least about or less than about 0.13 g, at least about or less than about 0.14 g, at least about or less than about 0.15 g, at least about or less than about 0.16 g, at least about or less than about 0.17 g, at least about or less than about 0.18 g, at least about or less than about 0.19 g, at least about or less than about 0.2 g, at least about or less than about 0.21 g, at least about or less than about 0.22 g, at least about or less than about 0.23 g, at least about or less than about 0.24 g, at least about or less than about 0.25 g, at least about or less than about 0.26 g, at least about or less than about 0.27 g, at least about or less than about 0.28 g, at least about or less than about 0.29 g, or at least about or less than about 0.3 g of at least one bile acid sequestrant. In certain embodiments, the dosage unit comprises at least about or less than about 95 mg of at least one proton pump inhibitor and at least about or less than about 0.01 g, at least about or less than about 0.02 g, at least about or less than about 0.03 g, at least about or less than about 0.04 g, at least about or less than about 0.05 g, at least about or less than about 0.06 g, at least about or less than about 0.07 g, at least about or less than about 0.08 g, at least about or less than about 0.09 g, at least about or less than about 0.1 g, at least about or less than about 0.11 g, at least about or less than about 0.12 g, at least about or less than about 0.13 g, at least about or less than about 0.14 g, at least about or less than about 0.15 g, at least about or less than about 0.16 g, at least about or less than about 0.17 g, at least about or less than about 0.18 g, at least about or less than about 0.19 g, at least about or less than about 0.2 g, at least about or less than about 0.21 g, at least about or less than about 0.22 g, at least about or less than about 0.23 g, at least about or less than about 0.24 g, at least about or less than about 0.25 g, at least about or less than about 0.26 g, at least about or less than about 0.27 g, at least about or less than about 0.28 g, at least about or less than about 0.29 g, or at least about or less than about 0.3 g of at least one bile acid sequestrant. In certain embodiments, the dosage unit comprises at least about or less than about 100 mg of at least one proton pump inhibitor and at least about or less than about 0.01 g, at least about or less than about 0.02 g, at least about or less than about 0.03 g, at least about or less than about 0.04 g, at least about or less than about 0.05 g, at least about or less than about 0.06 g, at least about or less than about 0.07 g, at least about or less than about 0.08 g, at least about or less than about 0.09 g, at least about or less than about 0.1 g, at least about or less than about 0.11 g, at least about or less than about 0.12 g, at least about or less than about 0.13 g, at least about or less than about 0.14 g, at least about or less than about 0.15 g, at least about or less than about 0.16 g, at least about or less than about 0.17 g, at least about or less than about 0.18 g, at least about or less than about 0.19 g, at least about or less than about 0.2 g, at least about or less than about 0.21 g, at least about or less than about 0.22 g, at least about or less than about 0.23 g, at least about or less than about 0.24 g, at least about or less than about 0.25 g, at least about or less than about 0.26 g, at least about or less than about 0.27 g, at least about or less than about 0.28 g, at least about or less than about 0.29 g, or at least about or less than about 0.3 g of at least one bile acid sequestrant. In certain embodiments the at least one proton pump inhibitor is omeprazole. In certain embodiments the at least one proton pump inhibitor is esomeprazole. In certain embodiments the at least one proton pump inhibitor is lansoprazole. In certain embodiments the at least one proton pump inhibitor is pantoprazole. In certain embodiments the at least one proton pump inhibitor is rabeprazole. In certain embodiments the at least one proton pump inhibitor is tenatoprazole. In certain embodiments the at least one bile acid sequestrant is cholestyramine. In certain embodiments the at least one bile acid sequestrant is colesevelam. In certain embodiments the at least one bile acid sequestrant is colesevelam-HCl. In certain embodiments the at least one bile acid sequestrant is colestipol. In certain embodiments the at least one proton pump inhibitor is omeprazole and the at least one bile acid sequestrant is cholestyramine. In certain embodiments the at least one proton pump inhibitor is omeprazole and the at least one bile acid sequestrant is colesevelam. In certain embodiments the at least one proton pump inhibitor is omeprazole and the at least one bile acid sequestrant is colesevelam-HCl. In certain embodiments the at least one proton pump inhibitor is omeprazole and the at least one bile acid sequestrant is colestipol. In certain embodiments the at least one proton pump inhibitor is esomeprazole and the at least one bile acid sequestrant is cholestyramine. In certain embodiments the at least one proton pump inhibitor is esomeprazole and the at least one bile acid sequestrant is colesevelam. In certain embodiments the at least one proton pump inhibitor is esomeprazole and the at least one bile acid sequestrant is colesevelam-HCl. In certain embodiments the at least one proton pump inhibitor is esomeprazole and the at least one bile acid sequestrant is colestipol. In certain embodiments the at least one proton pump inhibitor is lansoprazole and the at least one bile acid sequestrant is cholestyramine. In certain embodiments the at least one proton pump inhibitor is lansoprazole and the at least one bile acid sequestrant is colesevelam. In certain embodiments the at least one proton pump inhibitor is lansoprazole and the at least one bile acid sequestrant is colesevelam-HCl. In certain embodiments the at least one proton pump inhibitor is lansoprazole and the at least one bile acid sequestrant is colestipol. In certain embodiments the at least one proton pump inhibitor is pantoprazole and the at least one bile acid sequestrant is cholestyramine. In certain embodiments the at least one proton pump inhibitor is pantoprazole and the at least one bile acid sequestrant is colesevelam. In certain embodiments the at least one proton pump inhibitor is pantoprazole and the at least one bile acid sequestrant is colesevelam-HCl. In certain embodiments the at least one proton pump inhibitor is pantoprazole and the at least one bile acid sequestrant is colestipol. In certain embodiments the at least one proton pump inhibitor is rabeprazole and the at least one bile acid sequestrant is cholestyramine. In certain embodiments the at least one proton pump inhibitor is rabeprazole and the at least one bile acid sequestrant is colesevelam. In certain embodiments the at least one proton pump inhibitor is rabeprazole and the at least one bile acid sequestrant is colesevelam-HCl. In certain embodiments the at least one proton pump inhibitor is rabeprazole and the at least one bile acid sequestrant is colestipol. In certain embodiments the at least one proton pump inhibitor is tenatoprazole and the at least one bile acid sequestrant is cholestyramine. In certain embodiments the at least one proton pump inhibitor is tenatoprazole and the at least one bile acid sequestrant is colesevelam. In certain embodiments the at least one proton pump inhibitor is tenatoprazole and the at least one bile acid sequestrant is colesevelam-HCl. In certain embodiments the at least one proton pump inhibitor is tenatoprazole and the at least one bile acid sequestrant is colestipol. In certain embodiments the dosage unit and daily dose are equivalent. In various embodiments, the dosage unit is administered with food at anytime of the day, without food at anytime of the day, with food after an overnight fast (e.g. with breakfast), at bedtime after a low fat snack. In various embodiments, the dosage unit is administered once a day, twice a day, three times a day, four times a day. The dosage unit can optionally comprise other agents such as at least one antacid, at least one histamine $H_2$-receptor antagonist, or combinations thereof.

In certain embodiments, the dosage unit comprises at least about or less than about 5 mg of at least one proton pump inhibitor and at least about or less than about 5 g, at least about or less than about 10 g, at least about or less than about 15 g, at least about or less than about 20 g, at least about or less than about 25 g, at least about or less than about 30 g, at least about or less than about 35 g, at least about or less than about 40 g, at least about or less than about 45 g, at least about or less than about 50 g, at least about or less than about 55 g, at least about or less than about 60 g, at least about or less than about 65 g, at least about or less than about 70 g, at least about or less than about 75 g, at least about or less than about 80 g, at least about or less than about 85 g, at least about or less than about 90 g, at least about or less than about 95 g, at least about or less than about 100 g, at least about or less than about 105 g, at least about or less than about 110 g, at least about or less than about 115 g, at least about or less than about 120 g, at least about or less than about 125 g, at least about or less than about 130 g, at least about or less than about 135 g, at least about or less than about 140 g, at least about or less than about 145 g, or at least about or less than about 150 g of at least one bile acid sequestrant. In certain embodiments, the dosage unit comprises at least about or less than about 10 mg of at least one proton pump inhibitor and at least about or less than about 5 g, at least about or less than about 10 g, at least about or less than about 15 g, at least about or less than about 20 g, at least about or less than about 25 g, at least about or less than about 30 g, at least about or less than about 35 g, at least about or less than about 40 g, at least about or less than about 45 g, at least about or less than about 50 g, at least about or less than about 55 g, at least about or less than about 60 g, at least about or less than about 65 g, at least about or less than about 70 g, at least about or less than about 75 g, at least about or less than about 80 g, at least about or less than about 85 g, at least about or less than about 90 g, at least about or less than about 95 g, at least about or less than about 100 g, at least about or less than about 105 g, at least about or less than about 110 g, at least about or less than about 115 g, at least about or less than about 120 g, at least about or less than about 125 g, at least about or less than about 130 g, at least about or less than about 135 g, at least about or less than about 140 g, at least about or less than about 145 g, or at least about or less than about 150 g of at least one bile acid sequestrant. In certain embodiments, the dosage unit comprises at least about or less than about 15 mg of at least one proton pump inhibitor and at least about or less than about 5 g, at least about or less than about 10 g, at least about or less than about 15 g, at least about or less than about 20 g, at least about or less than about 25 g, at least about or less than about 30 g, at least about or less than about 35 g, at least about or less than about 40 g, at least about or less than about 45 g, at least about or less than about 50 g, at least about or less than about 55 g, at least about or less than about 60 g, at least about or less than about 65 g, at least about or less than about 70 g, at least about or less than about 75 g, at least about or less than about 80 g, at least about or less than about 85 g, at least about or less than about 90 g, at least about or less than about 95 g, at least about or less than about 100 g, at least about or less than about 105 g, at least about or less than about 110 g, at least about or less than about 115 g, at least about or less than about 120 g, at least about or less than about 125 g, at least about or less than about 130 g, at least about or less than about 135 g, at least about or less than about 140 g, at least about or less than about 145 g, or at least about or less than about 150 g of at least one bile acid sequestrant. In certain embodiments, the dosage unit comprises at least about or less than about 20 mg of at least one proton pump inhibitor and at least about or less than about 5 g, at least about or less than about 10 g, at least about or less than about 15 g, at least about or less than about 20 g, at least about or less than about 25 g, at least about or less than about 30 g, at least about or less than about 35 g, at least about or less than about 40 g, at least about or less than about 45 g, at least about or less than about 50 g, at least about or less than about 55 g, at least about or less than about 60 g, at least about or less than about 65 g, at least about or less than about 70 g, at least about or less than about 75 g, at least about or less than about 80 g, at least about or less than about 85 g, at least about or less than about 90 g, at least about or less than about 95 g, at least about or less than about 100 g, at least about or less than about 105 g, at least about or less than about 110 g, at least about or less than about 115 g, at least about or less than about 120 g, at least about or less than about 125 g, at least about or less than about 130 g, at least about or less than about 135 g, at least about or less than about 140 g, at least about or less than about 145 g, or at least about or less than about 150 g of at least one bile acid sequestrant. In certain embodiments, the dosage unit comprises at least about or less than about 25 mg of at least one proton pump inhibitor and at least about or less than about 5 g, at least about or less than about 10 g, at least about or less than about 15 g, at least about or less than about 20 g, at least about or less than about 25 g, at least about or less than about 30 g, at least about or less than about 35 g, at least about or less than about 40 g, at least about or less than about 45 g, at least about or less than about 50 g, at least about or less than about 55 g, at least about or less than about 60 g, at least about or less than about 65 g, at least about or less than about 70 g, at least about or less than about 75 g, at least about or less than about 80 g, at least about or less than about 85 g, at least about or less than about 90 g, at least about or less than about 95 g, at least about or less than about 100 g, at least about or less than about 105 g, at least about or less than about 110 g, at least about or less than about 115 g, at least about or less than about 120 g, at least about or less than about 125 g, at least about or less than about 130 g, at least about or less than about 135 g, at least about or less than about 140 g, at least about or less than about 145 g, or at least about or less than about 150 g of at least one bile acid sequestrant. In certain embodiments, the dosage unit comprises at least about or less than about 30 mg of at least one proton pump inhibitor and at least about or less than about 5 g, at least about or less than about 10 g, at least about or less than about 15 g, at least about or less than about 20 g, at least about or less than about 25 g, at least about or less than about 30 g, at least about or less than about 35 g, at least about or less than about 40 g, at least about or less than about 45 g, at least about or less than about 50 g, at least about or less than about 55 g, at least about or less than about 60 g, at least about or less than about 65 g, at least about or less than about 70 g, at least about or less than about 75 g, at least about or less than about 80 g, at least about or less than about 85 g, at least about or less than about 90 g, at least about or less than about 95 g, at least about or less than about 100 g, at least about or less than about 105 g, at least about or less than about 110 g, at least about or less than about 115 g, at least about or less than about 120 g, at least about or less than about 125 g, at least about or less than about 130 g, at least about or less than about 135 g, at least about or less than about 140 g, at least about or less than about 145 g, or at least about or less than about 150 g of at least one bile acid sequestrant. In certain embodiments, the dosage unit comprises at least about or less than about 35 mg of at least one proton pump inhibitor and at least about or less than about 5 g, at least about or less than about 10 g, at least about or less than about 15 g, at least about or less than about 20 g, at least about or less than about 25 g, at least about or less than about 30 g, at least about or less than about 35 g, at least about or less than about 40 g, at least about or less than about 45 g, at least about or less than about 50 g, at least about or less than about 55 g, at least about or less than about 60 g, at least about or less than about 65 g, at least about or less than about 70 g, at least about or less than about 75 g, at least about or less than about 80 g, at least about or less than about 85 g, at least about or less than about 90 g, at least about or less than about 95 g, at least about or less than about 100 g, at least about or less than about 105 g, at least about or less than about 110 g, at least about or less than about 115 g, at least about or less than about 120 g, at least about or less than about 125 g, at least about or less than about 130 g, at least about or less than about 135 g, at least about or less than about 140 g, at least about or less than about 145 g, or at least about or less than about 150 g of at least one bile acid sequestrant. In certain embodiments, the dosage unit comprises at least about or less than about 40 mg of at least one proton pump inhibitor and at least about or less than about 5 g, at least about or less than about 10 g, at least about or less than about 15 g, at least about or less than about 20 g, at least about or less than about 25 g, at least about or less than about 30 g, at least about or less than about 35 g, at least about or less than about 40 g, at least about or less than about 45 g, at least about or less than about 50 g, at least about or less than about 55 g, at least about or less than about 60 g, at least about or less than about 65 g, at least about or less than about 70 g, at least about or less than about 75 g, at least about or less than about 80 g, at least about or less than about 85 g, at least about or less than about 90 g, at least about or less than about 95 g, at least about or less than about 100 g, at least about or less than about 105 g, at least about or less than about 110 g, at least about or less than about 115 g, at least about or less than about 120 g, at least about or less than about 125 g, at least about or less than about 130 g, at least about or less than about 135 g, at least about or less than about 140 g, at least about or less than about 145 g, or at least about or less than about 150 g of at least one bile acid sequestrant. In certain embodiments, the dosage unit comprises at least about or less than about 45 mg of at least one proton pump inhibitor and at least about or less than about 5 g, at least about or less than about 10 g, at least about or less than about 15 g, at least about or less than about 20 g, at least about or less than about 25 g, at least about or less than about 30 g, at least about or less than about 35 g, at least about or less than about 40 g, at least about or less than about 45 g, at least about or less than about 50 g, at least about or less than about 55 g, at least about or less than about 60 g, at least about or less than about 65 g, at least about or less than about 70 g, at least about or less than about 75 g, at least about or less than about 80 g, at least about or less than about 85 g, at least about or less than about 90 g, at least about or less than about 95 g, at least about or less than about 100 g, at least about or less than about 105 g, at least about or less than about 110 g, at least about or less than about 115 g, at least about or less than about 120 g, at least about or less than about 125 g, at least about or less than about 130 g, at least about or less than about 135 g, at least about or less than about 140 g, at least about or less than about 145 g, or at least about or less than about 150 g of at least one bile acid sequestrant. In certain embodiments, the dosage unit comprises at least about or less than about 50 mg of at least one proton pump inhibitor and at least about or less than about 5 g, at least about or less than about 10 g, at least about or less than about 15 g, at least about or less than about 20 g, at least about or less than about 25 g, at least about or less than about 30 g, at least about or less than about 35 g, at least about or less than about 40 g, at least about or less than about 45 g, at least about or less than about 50 g, at least about or less than about 55 g, at least about or less than about 60 g, at least about or less than about 65 g, at least about or less than about 70 g, at least about or less than about 75 g, at least about or less than about 80 g, at least about or less than about 85 g, at least about or less than about 90 g, at least about or less than about 95 g, at least about or less than about 100 g, at least about or less than about 105 g, at least about or less than about 110 g, at least about or less than about 115 g, at least about or less than about 120 g, at least about or less than about 125 g, at least about or less than about 130 g, at least about or less than about 135 g, at least about or less than about 140 g, at least about or less than about 145 g, or at least about or less than about 150 g of at least one bile acid sequestrant. In certain embodiments, the dosage unit comprises at least about or less than about 55 mg of at least one proton pump inhibitor and at least about or less than about 5 g, at least about or less than about 10 g, at least about or less than about 15 g, at least about or less than about 20 g, at least about or less than about 25 g, at least about or less than about 30 g, at least about or less than about 35 g, at least about or less than about 40 g, at least about or less than about 45 g, at least about or less than about 50 g, at least about or less than about 55 g, at least about or less than about 60 g, at least about or less than about 65 g, at least about or less than about 70 g, at least about or less than about 75 g, at least about or less than about 80 g, at least about or less than about 85 g, at least about or less than about 90 g, at least about or less than about 95 g, at least about or less than about 100 g, at least about or less than about 105 g, at least about or less than about 110 g, at least about or less than about 115 g, at least about or less than about 120 g, at least about or less than about 125 g, at least about or less than about 130 g, at least about or less than about 135 g, at least about or less than about 140 g, at least about or less than about 145 g, or at least about or less than about 150 g of at least one bile acid sequestrant. In certain embodiments, the dosage unit comprises at least about or less than about 60 mg of at least one proton pump inhibitor and at least about or less than about 5 g, at least about or less than about 10 g, at least about or less than about 15 g, at least about or less than about 20 g, at least about or less than about 25 g, at least about or less than about 30 g, at least about or less than about 35 g, at least about or less than about 40 g, at least about or less than about 45 g, at least about or less than about 50 g, at least about or less than about 55 g, at least about or less than about 60 g, at least about or less than about 65 g, at least about or less than about 70 g, at least about or less than about 75 g, at least about or less than about 80 g, at least about or less than about 85 g, at least about or less than about 90 g, at least about or less than about 95 g, at least about or less than about 100 g, at least about or less than about 105 g, at least about or less than about 110 g, at least about or less than about 115 g, at least about or less than about 120 g, at least about or less than about 125 g, at least about or less than about 130 g, at least about or less than about 135 g, at least about or less than about 140 g, at least about or less than about 145 g, or at least about or less than about 150 g of at least one bile acid sequestrant. In certain embodiments, the dosage unit comprises at least about or less than about 65 mg of at least one proton pump inhibitor and at least about or less than about 5 g, at least about or less than about 10 g, at least about or less than about 15 g, at least about or less than about 20 g, at least about or less than about 25 g, at least about or less than about 30 g, at least about or less than about 35 g, at least about or less than about 40 g, at least about or less than about 45 g, at least about or less than about 50 g, at least about or less than about 55 g, at least about or less than about 60 g, at least about or less than about 65 g, at least about or less than about 70 g, at least about or less than about 75 g, at least about or less than about 80 g, at least about or less than about 85 g, at least about or less than about 90 g, at least about or less than about 95 g, at least about or less than about 100 g, at least about or less than about 105 g, at least about or less than about 110 g, at least about or less than about 115 g, at least about or less than about 120 g, at least about or less than about 125 g, at least about or less than about 130 g, at least about or less than about 135 g, at least about or less than about 140 g, at least about or less than about 145 g, or at least about or less than about 150 g of at least one bile acid sequestrant. In certain embodiments, the dosage unit comprises at least about or less than about 70 mg of at least one proton pump inhibitor and at least about or less than about 5 g, at least about or less than about 10 g, at least about or less than about 15 g, at least about or less than about 20 g, at least about or less than about 25 g, at least about or less than about 30 g, at least about or less than about 35 g, at least about or less than about 40 g, at least about or less than about 45 g, at least about or less than about 50 g, at least about or less than about 55 g, at least about or less than about 60 g, at least about or less than about 65 g, at least about or less than about 70 g, at least about or less than about 75 g, at least about or less than about 80 g, at least about or less than about 85 g, at least about or less than about 90 g, at least about or less than about 95 g, at least about or less than about 100 g, at least about or less than about 105 g, at least about or less than about 110 g, at least about or less than about 115 g, at least about or less than about 120 g, at least about or less than about 125 g, at least about or less than about 130 g, at least about or less than about 135 g, at least about or less than about 140 g, at least about or less than about 145 g, or at least about or less than about 150 g of at least one bile acid sequestrant. In certain embodiments, the dosage unit comprises at least about or less than about 75 mg of at least one proton pump inhibitor and at least about or less than about 5 g, at least about or less than about 10 g, at least about or less than about 15 g, at least about or less than about 20 g, at least about or less than about 25 g, at least about or less than about 30 g, at least about or less than about 35 g, at least about or less than about 40 g, at least about or less than about 45 g, at least about or less than about 50 g, at least about or less than about 55 g, at least about or less than about 60 g, at least about or less than about 65 g, at least about or less than about 70 g, at least about or less than about 75 g, at least about or less than about 80 g, at least about or less than about 85 g, at least about or less than about 90 g, at least about or less than about 95 g, at least about or less than about 100 g, at least about or less than about 105 g, at least about or less than about 110 g, at least about or less than about 115 g, at least about or less than about 120 g, at least about or less than about 125 g, at least about or less than about 130 g, at least about or less than about 135 g, at least about or less than about 140 g, at least about or less than about 145 g, or at least about or less than about 150 g of at least one bile acid sequestrant. In certain embodiments, the dosage unit comprises at least about or less than about 80 mg of at least one proton pump inhibitor and at least about or less than about 5 g, at least about or less than about 10 g, at least about or less than about 15 g, at least about or less than about 20 g, at least about or less than about 25 g, at least about or less than about 30 g, at least about or less than about 35 g, at least about or less than about 40 g, at least about or less than about 45 g, at least about or less than about 50 g, at least about or less than about 55 g, at least about or less than about 60 g, at least about or less than about 65 g, at least about or less than about 70 g, at least about or less than about 75 g, at least about or less than about 80 g, at least about or less than about 85 g, at least about or less than about 90 g, at least about or less than about 95 g, at least about or less than about 100 g, at least about or less than about 105 g, at least about or less than about 110 g, at least about or less than about 115 g, at least about or less than about 120 g, at least about or less than about 125 g, at least about or less than about 130 g, at least about or less than about 135 g, at least about or less than about 140 g, at least about or less than about 145 g, or at least about or less than about 150 g of at least one bile acid sequestrant. In certain embodiments, the dosage unit comprises at least about or less than about 85 mg of at least one proton pump inhibitor and at least about or less than about 5 g, at least about or less than about 10 g, at least about or less than about 15 g, at least about or less than about 20 g, at least about or less than about 25 g, at least about or less than about 30 g, at least about or less than about 35 g, at least about or less than about 40 g, at least about or less than about 45 g, at least about or less than about 50 g, at least about or less than about 55 g, at least about or less than about 60 g, at least about or less than about 65 g, at least about or less than about 70 g, at least about or less than about 75 g, at least about or less than about 80 g, at least about or less than about 85 g, at least about or less than about 90 g, at least about or less than about 95 g, at least about or less than about 100 g, at least about or less than about 105 g, at least about or less than about 110 g, at least about or less than about 115 g, at least about or less than about 120 g, at least about or less than about 125 g, at least about or less than about 130 g, at least about or less than about 135 g, at least about or less than about 140 g, at least about or less than about 145 g, or at least about or less than about 150 g of at least one bile acid sequestrant. In certain embodiments, the dosage unit comprises at least about or less than about 90 mg of at least one proton pump inhibitor and at least about or less than about 5 g, at least about or less than about 10 g, at least about or less than about 15 g, at least about or less than about 20 g, at least about or less than about 25 g, at least about or less than about 30 g, at least about or less than about 35 g, at least about or less than about 40 g, at least about or less than about 45 g, at least about or less than about 50 g, at least about or less than about 55 g, at least about or less than about 60 g, at least about or less than about 65 g, at least about or less than about 70 g, at least about or less than about 75 g, at least about or less than about 80 g, at least about or less than about 85 g, at least about or less than about 90 g, at least about or less than about 95 g, at least about or less than about 100 g, at least about or less than about 105 g, at least about or less than about 110 g, at least about or less than about 115 g, at least about or less than about 120 g, at least about or less than about 125 g, at least about or less than about 130 g, at least about or less than about 135 g, at least about or less than about 140 g, at least about or less than about 145 g, or at least about or less than about 150 g of at least one bile acid sequestrant. In certain embodiments, the dosage unit comprises at least about or less than about 95 mg of at least one proton pump inhibitor and at least about or less than about 5 g, at least about or less than about 10 g, at least about or less than about 15 g, at least about or less than about 20 g, at least about or less than about 25 g, at least about or less than about 30 g, at least about or less than about 35 g, at least about or less than about 40 g, at least about or less than about 45 g, at least about or less than about 50 g, at least about or less than about 55 g, at least about or less than about 60 g, at least about or less than about 65 g, at least about or less than about 70 g, at least about or less than about 75 g, at least about or less than about 80 g, at least about or less than about 85 g, at least about or less than about 90 g, at least about or less than about 95 g, at least about or less than about 100 g, at least about or less than about 105 g, at least about or less than about 110 g, at least about or less than about 115 g, at least about or less than about 120 g, at least about or less than about 125 g, at least about or less than about 130 g, at least about or less than about 135 g, at least about or less than about 140 g, at least about or less than about 145 g, or at least about or less than about 150 g of at least one bile acid sequestrant. In certain embodiments, the dosage unit comprises at least about or less than about 100 mg of at least one proton pump inhibitor and at least about or less than about 5 g, at least about or less than about 10 g, at least about or less than about 15 g, at least about or less than about 20 g, at least about or less than about 25 g, at least about or less than about 30 g, at least about or less than about 35 g, at least about or less than about 40 g, at least about or less than about 45 g, at least about or less than about 50 g, at least about or less than about 55 g, at least about or less than about 60 g, at least about or less than about 65 g, at least about or less than about 70 g, at least about or less than about 75 g, at least about or less than about 80 g, at least about or less than about 85 g, at least about or less than about 90 g, at least about or less than about 95 g, at least about or less than about 100 g, at least about or less than about 105 g, at least about or less than about 110 g, at least about or less than about 115 g, at least about or less than about 120 g, at least about or less than about 125 g, at least about or less than about 130 g, at least about or less than about 135 g, at least about or less than about 140 g, at least about or less than about 145 g, or at least about or less than about 150 g of at least one bile acid sequestrant. In certain embodiments the at least one proton pump inhibitor is omeprazole. In certain embodiments the at least one proton pump inhibitor is esomeprazole. In certain embodiments the at least one proton pump inhibitor is lansoprazole. In certain embodiments the at least one proton pump inhibitor is pantoprazole. In certain embodiments the at least one proton pump inhibitor is rabeprazole. In certain embodiments the at least one proton pump inhibitor is tenatoprazole. In certain embodiments the at least one bile acid sequestrant is cholestyramine. In certain embodiments the at least one bile acid sequestrant is colesevelam. In certain embodiments the at least one bile acid sequestrant is colesevelam-HCl. In certain embodiments the at least one bile acid sequestrant is colestipol. In certain embodiments the at least one proton pump inhibitor is omeprazole and the at least one bile acid sequestrant is cholestyramine. In certain embodiments the at least one proton pump inhibitor is omeprazole and the at least one bile acid sequestrant is colesevelam. In certain embodiments the at least one proton pump inhibitor is omeprazole and the at least one bile acid sequestrant is colesevelam-HCl. In certain embodiments the at least one proton pump inhibitor is omeprazole and the at least one bile acid sequestrant is colestipol. In certain embodiments the at least one proton pump inhibitor is esomeprazole and the at least one bile acid sequestrant is cholestyramine. In certain embodiments the at least one proton pump inhibitor is esomeprazole and the at least one bile acid sequestrant is colesevelam. In certain embodiments the at least one proton pump inhibitor is esomeprazole and the at least one bile acid sequestrant is colesevelam-HCl. In certain embodiments the at least one proton pump inhibitor is esomeprazole and the at least one bile acid sequestrant is colestipol. In certain embodiments the at least one proton pump inhibitor is lansoprazole and the at least one bile acid sequestrant is cholestyramine. In certain embodiments the at least one proton pump inhibitor is lansoprazole and the at least one bile acid sequestrant is colesevelam. In certain embodiments the at least one proton pump inhibitor is lansoprazole and the at least one bile acid sequestrant is colesevelam-HCl. In certain embodiments the at least one proton pump inhibitor is lansoprazole and the at least one bile acid sequestrant is colestipol. In certain embodiments the at least one proton pump inhibitor is pantoprazole and the at least one bile acid sequestrant is cholestyramine. In certain embodiments the at least one proton pump inhibitor is pantoprazole and the at least one bile acid sequestrant is colesevelam. In certain embodiments the at least one proton pump inhibitor is pantoprazole and the at least one bile acid sequestrant is colesevelam-HCl. In certain embodiments the at least one proton pump inhibitor is pantoprazole and the at least one bile acid sequestrant is colestipol. In certain embodiments the at least one proton pump inhibitor is rabeprazole and the at least one bile acid sequestrant is cholestyramine. In certain embodiments the at least one proton pump inhibitor is rabeprazole and the at least one bile acid sequestrant is colesevelam. In certain embodiments the at least one proton pump inhibitor is rabeprazole and the at least one bile acid sequestrant is colesevelam-HCl. In certain embodiments the at least one proton pump inhibitor is rabeprazole and the at least one bile acid sequestrant is colestipol. In certain embodiments the at least one proton pump inhibitor is tenatoprazole and the at least one bile acid sequestrant is cholestyramine. In certain embodiments the at least one proton pump inhibitor is tenatoprazole and the at least one bile acid sequestrant is colesevelam. In certain embodiments the at least one proton pump inhibitor is tenatoprazole and the at least one bile acid sequestrant is colesevelam-HCl. In certain embodiments the at least one proton pump inhibitor is tenatoprazole and the at least one bile acid sequestrant is colestipol. In certain embodiments the dosage unit and daily dose are equivalent. In various embodiments, the dosage unit is administered with food at anytime of the day, without food at anytime of the day, with food after an overnight fast (e.g. with breakfast), at bedtime after a low fat snack. In various embodiments, the dosage unit is administered once a day, twice a day, three times a day, four times a day. The dosage unit can optionally comprise other agents such as at least one antacid, at least one histamine $H_2$-receptor antagonist, or combinations thereof.

In certain embodiments, the dosage unit comprises at least about or less than about 5 mg of at least one proton pump inhibitor and at least about or less than about 2 g, at least about or less than about 4 g, at least about or less than about 6 g, at least about or less than about 8 g, at least about or less than about 10 g, at least about or less than about 12 g, at least about or less than about 14 g, at least about or less than about 16 g, at least about or less than about 18 g, at least about or less than about 20 g, at least about or less than about 22 g, at least about or less than about 24 g, at least about or less than about 26 g, at least about or less than about 28 g, at least about or less than about 30 g, at least about or less than about 32 g, at least about or less than about 34 g, at least about or less than about 36 g, at least about or less than about 38 g, at least about or less than about 40 g, at least about or less than about 42 g, at least about or less than about 44 g, at least about or less than about 46 g, at least about or less than about 48 g, at least about or less than about 50 g, at least about or less than about 52 g, at least about or less than about 54 g, at least about or less than about 56 g, at least about or less than about 58 g, or at least about or less than about 60 g of at least one bile acid sequestrant. In certain embodiments, the dosage unit comprises at least about or less than about 10 mg of at least one proton pump inhibitor and at least about or less than about 2 g, at least about or less than about 4 g, at least about or less than about 6 g, at least about or less than about 8 g, at least about or less than about 10 g, at least about or less than about 12 g, at least about or less than about 14 g, at least about or less than about 16 g, at least about or less than about 18 g, at least about or less than about 20 g, at least about or less than about 22 g, at least about or less than about 24 g, at least about or less than about 26 g, at least about or less than about 28 g, at least about or less than about 30 g, at least about or less than about 32 g, at least about or less than about 34 g, at least about or less than about 36 g, at least about or less than about 38 g, at least about or less than about 40 g, at least about or less than about 42 g, at least about or less than about 44 g, at least about or less than about 46 g, at least about or less than about 48 g, at least about or less than about 50 g, at least about or less than about 52 g, at least about or less than about 54 g, at least about or less than about 56 g, at least about or less than about 58 g, or at least about or less than about 60 g of at least one bile acid sequestrant. In certain embodiments, the dosage unit comprises at least about or less than about 15 mg of at least one proton pump inhibitor and at least about or less than about 2 g, at least about or less than about 4 g, at least about or less than about 6 g, at least about or less than about 8 g, at least about or less than about 10 g, at least about or less than about 12 g, at least about or less than about 14 g, at least about or less than about 16 g, at least about or less than about 18 g, at least about or less than about 20 g, at least about or less than about 22 g, at least about or less than about 24 g, at least about or less than about 26 g, at least about or less than about 28 g, at least about or less than about 30 g, at least about or less than about 32 g, at least about or less than about 34 g, at least about or less than about 36 g, at least about or less than about 38 g, at least about or less than about 40 g, at least about or less than about 42 g, at least about or less than about 44 g, at least about or less than about 46 g, at least about or less than about 48 g, at least about or less than about 50 g, at least about or less than about 52 g, at least about or less than about 54 g, at least about or less than about 56 g, at least about or less than about 58 g, or at least about or less than about 60 g of at least one bile acid sequestrant. In certain embodiments, the dosage unit comprises at least about or less than about 20 mg of at least one proton pump inhibitor and at least about or less than about 2 g, at least about or less than about 4 g, at least about or less than about 6 g, at least about or less than about 8 g, at least about or less than about 10 g, at least about or less than about 12 g, at least about or less than about 14 g, at least about or less than about 16 g, at least about or less than about 18 g, at least about or less than about 20 g, at least about or less than about 22 g, at least about or less than about 24 g, at least about or less than about 26 g, at least about or less than about 28 g, at least about or less than about 30 g, at least about or less than about 32 g, at least about or less than about 34 g, at least about or less than about 36 g, at least about or less than about 38 g, at least about or less than about 40 g, at least about or less than about 42 g, at least about or less than about 44 g, at least about or less than about 46 g, at least about or less than about 48 g, at least about or less than about 50 g, at least about or less than about 52 g, at least about or less than about 54 g, at least about or less than about 56 g, at least about or less than about 58 g, or at least about or less than about 60 g of at least one bile acid sequestrant. In certain embodiments, the dosage unit comprises at least about or less than about 25 mg of at least one proton pump inhibitor and at least about or less than about 2 g, at least about or less than about 4 g, at least about or less than about 6 g, at least about or less than about 8 g, at least about or less than about 10 g, at least about or less than about 12 g, at least about or less than about 14 g, at least about or less than about 16 g, at least about or less than about 18 g, at least about or less than about 20 g, at least about or less than about 22 g, at least about or less than about 24 g, at least about or less than about 26 g, at least about or less than about 28 g, at least about or less than about 30 g, at least about or less than about 32 g, at least about or less than about 34 g, at least about or less than about 36 g, at least about or less than about 38 g, at least about or less than about 40 g, at least about or less than about 42 g, at least about or less than about 44 g, at least about or less than about 46 g, at least about or less than about 48 g, at least about or less than about 50 g, at least about or less than about 52 g, at least about or less than about 54 g, at least about or less than about 56 g, at least about or less than about 58 g, or at least about or less than about 60 g of at least one bile acid sequestrant. In certain embodiments, the dosage unit comprises at least about or less than about 30 mg of at least one proton pump inhibitor and at least about or less than about 2 g, at least about or less than about 4 g, at least about or less than about 6 g, at least about or less than about 8 g, at least about or less than about 10 g, at least about or less than about 12 g, at least about or less than about 14 g, at least about or less than about 16 g, at least about or less than about 18 g, at least about or less than about 20 g, at least about or less than about 22 g, at least about or less than about 24 g, at least about or less than about 26 g, at least about or less than about 28 g, at least about or less than about 30 g, at least about or less than about 32 g, at least about or less than about 34 g, at least about or less than about 36 g, at least about or less than about 38 g, at least about or less than about 40 g, at least about or less than about 42 g, at least about or less than about 44 g, at least about or less than about 46 g, at least about or less than about 48 g, at least about or less than about 50 g, at least about or less than about 52 g, at least about or less than about 54 g, at least about or less than about 56 g, at least about or less than about 58 g, or at least about or less than about 60 g of at least one bile acid sequestrant. In certain embodiments, the dosage unit comprises at least about or less than about 35 mg of at least one proton pump inhibitor and at least about or less than about 2 g, at least about or less than about 4 g, at least about or less than about 6 g, at least about or less than about 8 g, at least about or less than about 10 g, at least about or less than about 12 g, at least about or less than about 14 g, at least about or less than about 16 g, at least about or less than about 18 g, at least about or less than about 20 g, at least about or less than about 22 g, at least about or less than about 24 g, at least about or less than about 26 g, at least about or less than about 28 g, at least about or less than about 30 g, at least about or less than about 32 g, at least about or less than about 34 g, at least about or less than about 36 g, at least about or less than about 38 g, at least about or less than about 40 g, at least about or less than about 42 g, at least about or less than about 44 g, at least about or less than about 46 g, at least about or less than about 48 g, at least about or less than about 50 g, at least about or less than about 52 g, at least about or less than about 54 g, at least about or less than about 56 g, at least about or less than about 58 g, or at least about or less than about 60 g of at least one bile acid sequestrant. In certain embodiments, the dosage unit comprises at least about or less than about 40 mg of at least one proton pump inhibitor and at least about or less than about 2 g, at least about or less than about 4 g, at least about or less than about 6 g, at least about or less than about 8 g, at least about or less than about 10 g, at least about or less than about 12 g, at least about or less than about 14 g, at least about or less than about 16 g, at least about or less than about 18 g, at least about or less than about 20 g, at least about or less than about 22 g, at least about or less than about 24 g, at least about or less than about 26 g, at least about or less than about 28 g, at least about or less than about 30 g, at least about or less than about 32 g, at least about or less than about 34 g, at least about or less than about 36 g, at least about or less than about 38 g, at least about or less than about 40 g, at least about or less than about 42 g, at least about or less than about 44 g, at least about or less than about 46 g, at least about or less than about 48 g, at least about or less than about 50 g, at least about or less than about 52 g, at least about or less than about 54 g, at least about or less than about 56 g, at least about or less than about 58 g, or at least about or less than about 60 g of at least one bile acid sequestrant. In certain embodiments, the dosage unit comprises at least about or less than about 45 mg of at least one proton pump inhibitor and at least about or less than about 2 g, at least about or less than about 4 g, at least about or less than about 6 g, at least about or less than about 8 g, at least about or less than about 10 g, at least about or less than about 12 g, at least about or less than about 14 g, at least about or less than about 16 g, at least about or less than about 18 g, at least about or less than about 20 g, at least about or less than about 22 g, at least about or less than about 24 g, at least about or less than about 26 g, at least about or less than about 28 g, at least about or less than about 30 g, at least about or less than about 32 g, at least about or less than about 34 g, at least about or less than about 36 g, at least about or less than about 38 g, at least about or less than about 40 g, at least about or less than about 42 g, at least about or less than about 44 g, at least about or less than about 46 g, at least about or less than about 48 g, at least about or less than about 50 g, at least about or less than about 52 g, at least about or less than about 54 g, at least about or less than about 56 g, at least about or less than about 58 g, or at least about or less than about 60 g of at least one bile acid sequestrant. In certain embodiments, the dosage unit comprises at least about or less than about 50 mg of at least one proton pump inhibitor and at least about or less than about 2 g, at least about or less than about 4 g, at least about or less than about 6 g, at least about or less than about 8 g, at least about or less than about 10 g, at least about or less than about 12 g, at least about or less than about 14 g, at least about or less than about 16 g, at least about or less than about 18 g, at least about or less than about 20 g, at least about or less than about 22 g, at least about or less than about 24 g, at least about or less than about 26 g, at least about or less than about 28 g, at least about or less than about 30 g, at least about or less than about 32 g, at least about or less than about 34 g, at least about or less than about 36 g, at least about or less than about 38 g, at least about or less than about 40 g, at least about or less than about 42 g, at least about or less than about 44 g, at least about or less than about 46 g, at least about or less than about 48 g, at least about or less than about 50 g, at least about or less than about 52 g, at least about or less than about 54 g, at least about or less than about 56 g, at least about or less than about 58 g, or at least about or less than about 60 g of at least one bile acid sequestrant. In certain embodiments, the dosage unit comprises at least about or less than about 55 mg of at least one proton pump inhibitor and at least about or less than about 2 g, at least about or less than about 4 g, at least about or less than about 6 g, at least about or less than about 8 g, at least about or less than about 10 g, at least about or less than about 12 g, at least about or less than about 14 g, at least about or less than about 16 g, at least about or less than about 18 g, at least about or less than about 20 g, at least about or less than about 22 g, at least about or less than about 24 g, at least about or less than about 26 g, at least about or less than about 28 g, at least about or less than about 30 g, at least about or less than about 32 g, at least about or less than about 34 g, at least about or less than about 36 g, at least about or less than about 38 g, at least about or less than about 40 g, at least about or less than about 42 g, at least about or less than about 44 g, at least about or less than about 46 g, at least about or less than about 48 g, at least about or less than about 50 g, at least about or less than about 52 g, at least about or less than about 54 g, at least about or less than about 56 g, at least about or less than about 58 g, or at least about or less than about 60 g of at least one bile acid sequestrant. In certain embodiments, the dosage unit comprises at least about or less than about 60 mg of at least one proton pump inhibitor and at least about or less than about 2 g, at least about or less than about 4 g, at least about or less than about 6 g, at least about or less than about 8 g, at least about or less than about 10 g, at least about or less than about 12 g, at least about or less than about 14 g, at least about or less than about 16 g, at least about or less than about 18 g, at least about or less than about 20 g, at least about or less than about 22 g, at least about or less than about 24 g, at least about or less than about 26 g, at least about or less than about 28 g, at least about or less than about 30 g, at least about or less than about 32 g, at least about or less than about 34 g, at least about or less than about 36 g, at least about or less than about 38 g, at least about or less than about 40 g, at least about or less than about 42 g, at least about or less than about 44 g, at least about or less than about 46 g, at least about or less than about 48 g, at least about or less than about 50 g, at least about or less than about 52 g, at least about or less than about 54 g, at least about or less than about 56 g, at least about or less than about 58 g, or at least about or less than about 60 g of at least one bile acid sequestrant. In certain embodiments, the dosage unit comprises at least about or less than about 65 mg of at least one proton pump inhibitor and at least about or less than about 2 g, at least about or less than about 4 g, at least about or less than about 6 g, at least about or less than about 8 g, at least about or less than about 10 g, at least about or less than about 12 g, at least about or less than about 14 g, at least about or less than about 16 g, at least about or less than about 18 g, at least about or less than about 20 g, at least about or less than about 22 g, at least about or less than about 24 g, at least about or less than about 26 g, at least about or less than about 28 g, at least about or less than about 30 g, at least about or less than about 32 g, at least about or less than about 34 g, at least about or less than about 36 g, at least about or less than about 38 g, at least about or less than about 40 g, at least about or less than about 42 g, at least about or less than about 44 g, at least about or less than about 46 g, at least about or less than about 48 g, at least about or less than about 50 g, at least about or less than about 52 g, at least about or less than about 54 g, at least about or less than about 56 g, at least about or less than about 58 g, or at least about or less than about 60 g of at least one bile acid sequestrant. In certain embodiments, the dosage unit comprises at least about or less than about 70 mg of at least one proton pump inhibitor and at least about or less than about 2 g, at least about or less than about 4 g, at least about or less than about 6 g, at least about or less than about 8 g, at least about or less than about 10 g, at least about or less than about 12 g, at least about or less than about 14 g, at least about or less than about 16 g, at least about or less than about 18 g, at least about or less than about 20 g, at least about or less than about 22 g, at least about or less than about 24 g, at least about or less than about 26 g, at least about or less than about 28 g, at least about or less than about 30 g, at least about or less than about 32 g, at least about or less than about 34 g, at least about or less than about 36 g, at least about or less than about 38 g, at least about or less than about 40 g, at least about or less than about 42 g, at least about or less than about 44 g, at least about or less than about 46 g, at least about or less than about 48 g, at least about or less than about 50 g, at least about or less than about 52 g, at least about or less than about 54 g, at least about or less than about 56 g, at least about or less than about 58 g, or at least about or less than about 60 g of at least one bile acid sequestrant. In certain embodiments, the dosage unit comprises at least about or less than about 75 mg of at least one proton pump inhibitor and at least about or less than about 2 g, at least about or less than about 4 g, at least about or less than about 6 g, at least about or less than about 8 g, at least about or less than about 10 g, at least about or less than about 12 g, at least about or less than about 14 g, at least about or less than about 16 g, at least about or less than about 18 g, at least about or less than about 20 g, at least about or less than about 22 g, at least about or less than about 24 g, at least about or less than about 26 g, at least about or less than about 28 g, at least about or less than about 30 g, at least about or less than about 32 g, at least about or less than about 34 g, at least about or less than about 36 g, at least about or less than about 38 g, at least about or less than about 40 g, at least about or less than about 42 g, at least about or less than about 44 g, at least about or less than about 46 g, at least about or less than about 48 g, at least about or less than about 50 g, at least about or less than about 52 g, at least about or less than about 54 g, at least about or less than about 56 g, at least about or less than about 58 g, or at least about or less than about 60 g of at least one bile acid sequestrant. In certain embodiments, the dosage unit comprises at least about or less than about 80 mg of at least one proton pump inhibitor and at least about or less than about 2 g, at least about or less than about 4 g, at least about or less than about 6 g, at least about or less than about 8 g, at least about or less than about 10 g, at least about or less than about 12 g, at least about or less than about 14 g, at least about or less than about 16 g, at least about or less than about 18 g, at least about or less than about 20 g, at least about or less than about 22 g, at least about or less than about 24 g, at least about or less than about 26 g, at least about or less than about 28 g, at least about or less than about 30 g, at least about or less than about 32 g, at least about or less than about 34 g, at least about or less than about 36 g, at least about or less than about 38 g, at least about or less than about 40 g, at least about or less than about 42 g, at least about or less than about 44 g, at least about or less than about 46 g, at least about or less than about 48 g, at least about or less than about 50 g, at least about or less than about 52 g, at least about or less than about 54 g, at least about or less than about 56 g, at least about or less than about 58 g, or at least about or less than about 60 g of at least one bile acid sequestrant. In certain embodiments, the dosage unit comprises at least about or less than about 85 mg of at least one proton pump inhibitor and at least about or less than about 2 g, at least about or less than about 4 g, at least about or less than about 6 g, at least about or less than about 8 g, at least about or less than about 10 g, at least about or less than about 12 g, at least about or less than about 14 g, at least about or less than about 16 g, at least about or less than about 18 g, at least about or less than about 20 g, at least about or less than about 22 g, at least about or less than about 24 g, at least about or less than about 26 g, at least about or less than about 28 g, at least about or less than about 30 g, at least about or less than about 32 g, at least about or less than about 34 g, at least about or less than about 36 g, at least about or less than about 38 g, at least about or less than about 40 g, at least about or less than about 42 g, at least about or less than about 44 g, at least about or less than about 46 g, at least about or less than about 48 g, at least about or less than about 50 g, at least about or less than about 52 g, at least about or less than about 54 g, at least about or less than about 56 g, at least about or less than about 58 g, or at least about or less than about 60 g of at least one bile acid sequestrant. In certain embodiments, the dosage unit comprises at least about or less than about 90 mg of at least one proton pump inhibitor and at least about or less than about 2 g, at least about or less than about 4 g, at least about or less than about 6 g, at least about or less than about 8 g, at least about or less than about 10 g, at least about or less than about 12 g, at least about or less than about 14 g, at least about or less than about 16 g, at least about or less than about 18 g, at least about or less than about 20 g, at least about or less than about 22 g, at least about or less than about 24 g, at least about or less than about 26 g, at least about or less than about 28 g, at least about or less than about 30 g, at least about or less than about 32 g, at least about or less than about 34 g, at least about or less than about 36 g, at least about or less than about 38 g, at least about or less than about 40 g, at least about or less than about 42 g, at least about or less than about 44 g, at least about or less than about 46 g, at least about or less than about 48 g, at least about or less than about 50 g, at least about or less than about 52 g, at least about or less than about 54 g, at least about or less than about 56 g, at least about or less than about 58 g, or at least about or less than about 60 g of at least one bile acid sequestrant. In certain embodiments, the dosage unit comprises at least about or less than about 95 mg of at least one proton pump inhibitor and at least about or less than about 2 g, at least about or less than about 4 g, at least about or less than about 6 g, at least about or less than about 8 g, at least about or less than about 10 g, at least about or less than about 12 g, at least about or less than about 14 g, at least about or less than about 16 g, at least about or less than about 18 g, at least about or less than about 20 g, at least about or less than about 22 g, at least about or less than about 24 g, at least about or less than about 26 g, at least about or less than about 28 g, at least about or less than about 30 g, at least about or less than about 32 g, at least about or less than about 34 g, at least about or less than about 36 g, at least about or less than about 38 g, at least about or less than about 40 g, at least about or less than about 42 g, at least about or less than about 44 g, at least about or less than about 46 g, at least about or less than about 48 g, at least about or less than about 50 g, at least about or less than about 52 g, at least about or less than about 54 g, at least about or less than about 56 g, at least about or less than about 58 g, or at least about or less than about 60 g of at least one bile acid sequestrant. In certain embodiments, the dosage unit comprises at least about or less than about 100 mg of at least one proton pump inhibitor and at least about or less than about 2 g, at least about or less than about 4 g, at least about or less than about 6 g, at least about or less than about 8 g, at least about or less than about 10 g, at least about or less than about 12 g, at least about or less than about 14 g, at least about or less than about 16 g, at least about or less than about 18 g, at least about or less than about 20 g, at least about or less than about 22 g, at least about or less than about 24 g, at least about or less than about 26 g, at least about or less than about 28 g, at least about or less than about 30 g, at least about or less than about 32 g, at least about or less than about 34 g, at least about or less than about 36 g, at least about or less than about 38 g, at least about or less than about 40 g, at least about or less than about 42 g, at least about or less than about 44 g, at least about or less than about 46 g, at least about or less than about 48 g, at least about or less than about 50 g, at least about or less than about 52 g, at least about or less than about 54 g, at least about or less than about 56 g, at least about or less than about 58 g, or at least about or less than about 60 g of at least one bile acid sequestrant. In certain embodiments the at least one proton pump inhibitor is omeprazole. In certain embodiments the at least one proton pump inhibitor is esomeprazole. In certain embodiments the at least one proton pump inhibitor is lansoprazole. In certain embodiments the at least one proton pump inhibitor is pantoprazole. In certain embodiments the at least one proton pump inhibitor is rabeprazole. In certain embodiments the at least one proton pump inhibitor is tenatoprazole. In certain embodiments the at least one bile acid sequestrant is cholestyramine. In certain embodiments the at least one bile acid sequestrant is colesevelam. In certain embodiments the at least one bile acid sequestrant is colesevelam-HCl. In certain embodiments the at least one bile acid sequestrant is colestipol. In certain embodiments the at least one proton pump inhibitor is omeprazole and the at least one bile acid sequestrant is cholestyramine. In certain embodiments the at least one proton pump inhibitor is omeprazole and the at least one bile acid sequestrant is colesevelam. In certain embodiments the at least one proton pump inhibitor is omeprazole and the at least one bile acid sequestrant is colesevelam-HCl. In certain embodiments the at least one proton pump inhibitor is omeprazole and the at least one bile acid sequestrant is colestipol. In certain embodiments the at least one proton pump inhibitor is esomeprazole and the at least one bile acid sequestrant is cholestyramine. In certain embodiments the at least one proton pump inhibitor is esomeprazole and the at least one bile acid sequestrant is colesevelam. In certain embodiments the at least one proton pump inhibitor is esomeprazole and the at least one bile acid sequestrant is colesevelam-HCl. In certain embodiments the at least one proton pump inhibitor is esomeprazole and the at least one bile acid sequestrant is colestipol. In certain embodiments the at least one proton pump inhibitor is lansoprazole and the at least one bile acid sequestrant is cholestyramine. In certain embodiments the at least one proton pump inhibitor is lansoprazole and the at least one bile acid sequestrant is colesevelam. In certain embodiments the at least one proton pump inhibitor is lansoprazole and the at least one bile acid sequestrant is colesevelam-HCl. In certain embodiments the at least one proton pump inhibitor is lansoprazole and the at least one bile acid sequestrant is colestipol. In certain embodiments the at least one proton pump inhibitor is pantoprazole and the at least one bile acid sequestrant is cholestyramine. In certain embodiments the at least one proton pump inhibitor is pantoprazole and the at least one bile acid sequestrant is colesevelam. In certain embodiments the at least one proton pump inhibitor is pantoprazole and the at least one bile acid sequestrant is colesevelam-HCl. In certain embodiments the at least one proton pump inhibitor is pantoprazole and the at least one bile acid sequestrant is colestipol. In certain embodiments the at least one proton pump inhibitor is rabeprazole and the at least one bile acid sequestrant is cholestyramine. In certain embodiments the at least one proton pump inhibitor is rabeprazole and the at least one bile acid sequestrant is colesevelam. In certain embodiments the at least one proton pump inhibitor is rabeprazole and the at least one bile acid sequestrant is colesevelam-HCl. In certain embodiments the at least one proton pump inhibitor is rabeprazole and the at least one bile acid sequestrant is colestipol. In certain embodiments the at least one proton pump inhibitor is tenatoprazole and the at least one bile acid sequestrant is cholestyramine. In certain embodiments the at least one proton pump inhibitor is tenatoprazole and the at least one bile acid sequestrant is colesevelam. In certain embodiments the at least one proton pump inhibitor is tenatoprazole and the at least one bile acid sequestrant is colesevelam-HCl. In certain embodiments the at least one proton pump inhibitor is tenatoprazole and the at least one bile acid sequestrant is colestipol. In certain embodiments the dosage unit and daily dose are equivalent. In various embodiments, the dosage unit is administered with food at anytime of the day, without food at anytime of the day, with food after an overnight fast (e.g. with breakfast), at bedtime after a low fat snack. In various embodiments, the dosage unit is administered once a day, twice a day, three times a day, four times a day. The dosage unit can optionally comprise other agents such as at least one antacid, at least one histamine $H_2$-receptor antagonist, or combinations thereof.

In certain embodiments, the dosage unit comprises at least about or less than about 5 mg of at least one proton pump inhibitor and at least about or less than about 10 g, at least about or less than about 20 g, at least about or less than about 30 g, at least about or less than about 40 g, at least about or less than about 50 g, at least about or less than about 60 g, at least about or less than about 70 g, at least about or less than about 80 g, at least about or less than about 90 g, at least about or less than about 100 g, at least about or less than about 110 g, at least about or less than about 120 g, at least about or less than about 130 g, at least about or less than about 140 g, at least about or less than about 150 g, at least about or less than about 160 g, at least about or less than about 170 g, at least about or less than about 180 g, at least about or less than about 190 g, at least about or less than about 200 g, at least about or less than about 210 g, at least about or less than about 220 g, at least about or less than about 230 g, at least about or less than about 240 g, at least about or less than about 250 g, at least about or less than about 260 g, at least about or less than about 270 g, at least about or less than about 280 g, at least about or less than about 290 g, or at least about or less than about 300 g of at least one bile acid sequestrant. In certain embodiments, the dosage unit comprises at least about or less than about 10 mg of at least one proton pump inhibitor and at least about or less than about 10 g, at least about or less than about 20 g, at least about or less than about 30 g, at least about or less than about 40 g, at least about or less than about 50 g, at least about or less than about 60 g, at least about or less than about 70 g, at least about or less than about 80 g, at least about or less than about 90 g, at least about or less than about 100 g, at least about or less than about 110 g, at least about or less than about 120 g, at least about or less than about 130 g, at least about or less than about 140 g, at least about or less than about 150 g, at least about or less than about 160 g, at least about or less than about 170 g, at least about or less than about 180 g, at least about or less than about 190 g, at least about or less than about 200 g, at least about or less than about 210 g, at least about or less than about 220 g, at least about or less than about 230 g, at least about or less than about 240 g, at least about or less than about 250 g, at least about or less than about 260 g, at least about or less than about 270 g, at least about or less than about 280 g, at least about or less than about 290 g, or at least about or less than about 300 g of at least one bile acid sequestrant. In certain embodiments, the dosage unit comprises at least about or less than about 15 mg of at least one proton pump inhibitor and at least about or less than about 10 g, at least about or less than about 20 g, at least about or less than about 30 g, at least about or less than about 40 g, at least about or less than about 50 g, at least about or less than about 60 g, at least about or less than about 70 g, at least about or less than about 80 g, at least about or less than about 90 g, at least about or less than about 100 g, at least about or less than about 110 g, at least about or less than about 120 g, at least about or less than about 130 g, at least about or less than about 140 g, at least about or less than about 150 g, at least about or less than about 160 g, at least about or less than about 170 g, at least about or less than about 180 g, at least about or less than about 190 g, at least about or less than about 200 g, at least about or less than about 210 g, at least about or less than about 220 g, at least about or less than about 230 g, at least about or less than about 240 g, at least about or less than about 250 g, at least about or less than about 260 g, at least about or less than about 270 g, at least about or less than about 280 g, at least about or less than about 290 g, or at least about or less than about 300 g of at least one bile acid sequestrant. In certain embodiments, the dosage unit comprises at least about or less than about 20 mg of at least one proton pump inhibitor and at least about or less than about 10 g, at least about or less than about 20 g, at least about or less than about 30 g, at least about or less than about 40 g, at least about or less than about 50 g, at least about or less than about 60 g, at least about or less than about 70 g, at least about or less than about 80 g, at least about or less than about 90 g, at least about or less than about 100 g, at least about or less than about 110 g, at least about or less than about 120 g, at least about or less than about 130 g, at least about or less than about 140 g, at least about or less than about 150 g, at least about or less than about 160 g, at least about or less than about 170 g, at least about or less than about 180 g, at least about or less than about 190 g, at least about or less than about 200 g, at least about or less than about 210 g, at least about or less than about 220 g, at least about or less than about 230 g, at least about or less than about 240 g, at least about or less than about 250 g, at least about or less than about 260 g, at least about or less than about 270 g, at least about or less than about 280 g, at least about or less than about 290 g, or at least about or less than about 300 g of at least one bile acid sequestrant. In certain embodiments, the dosage unit comprises at least about or less than about 25 mg of at least one proton pump inhibitor and at least about or less than about 10 g, at least about or less than about 20 g, at least about or less than about 30 g, at least about or less than about 40 g, at least about or less than about 50 g, at least about or less than about 60 g, at least about or less than about 70 g, at least about or less than about 80 g, at least about or less than about 90 g, at least about or less than about 100 g, at least about or less than about 110 g, at least about or less than about 120 g, at least about or less than about 130 g, at least about or less than about 140 g, at least about or less than about 150 g, at least about or less than about 160 g, at least about or less than about 170 g, at least about or less than about 180 g, at least about or less than about 190 g, at least about or less than about 200 g, at least about or less than about 210 g, at least about or less than about 220 g, at least about or less than about 230 g, at least about or less than about 240 g, at least about or less than about 250 g, at least about or less than about 260 g, at least about or less than about 270 g, at least about or less than about 280 g, at least about or less than about 290 g, or at least about or less than about 300 g of at least one bile acid sequestrant. In certain embodiments, the dosage unit comprises at least about or less than about 30 mg of at least one proton pump inhibitor and at least about or less than about 10 g, at least about or less than about 20 g, at least about or less than about 30 g, at least about or less than about 40 g, at least about or less than about 50 g, at least about or less than about 60 g, at least about or less than about 70 g, at least about or less than about 80 g, at least about or less than about 90 g, at least about or less than about 100 g, at least about or less than about 110 g, at least about or less than about 120 g, at least about or less than about 130 g, at least about or less than about 140 g, at least about or less than about 150 g, at least about or less than about 160 g, at least about or less than about 170 g, at least about or less than about 180 g, at least about or less than about 190 g, at least about or less than about 200 g, at least about or less than about 210 g, at least about or less than about 220 g, at least about or less than about 230 g, at least about or less than about 240 g, at least about or less than about 250 g, at least about or less than about 260 g, at least about or less than about 270 g, at least about or less than about 280 g, at least about or less than about 290 g, or at least about or less than about 300 g of at least one bile acid sequestrant. In certain embodiments, the dosage unit comprises at least about or less than about 35 mg of at least one proton pump inhibitor and at least about or less than about 10 g, at least about or less than about 20 g, at least about or less than about 30 g, at least about or less than about 40 g, at least about or less than about 50 g, at least about or less than about 60 g, at least about or less than about 70 g, at least about or less than about 80 g, at least about or less than about 90 g, at least about or less than about 100 g, at least about or less than about 110 g, at least about or less than about 120 g, at least about or less than about 130 g, at least about or less than about 140 g, at least about or less than about 150 g, at least about or less than about 160 g, at least about or less than about 170 g, at least about or less than about 180 g, at least about or less than about 190 g, at least about or less than about 200 g, at least about or less than about 210 g, at least about or less than about 220 g, at least about or less than about 230 g, at least about or less than about 240 g, at least about or less than about 250 g, at least about or less than about 260 g, at least about or less than about 270 g, at least about or less than about 280 g, at least about or less than about 290 g, or at least about or less than about 300 g of at least one bile acid sequestrant. In certain embodiments, the dosage unit comprises at least about or less than about 40 mg of at least one proton pump inhibitor and at least about or less than about 10 g, at least about or less than about 20 g, at least about or less than about 30 g, at least about or less than about 40 g, at least about or less than about 50 g, at least about or less than about 60 g, at least about or less than about 70 g, at least about or less than about 80 g, at least about or less than about 90 g, at least about or less than about 100 g, at least about or less than about 110 g, at least about or less than about 120 g, at least about or less than about 130 g, at least about or less than about 140 g, at least about or less than about 150 g, at least about or less than about 160 g, at least about or less than about 170 g, at least about or less than about 180 g, at least about or less than about 190 g, at least about or less than about 200 g, at least about or less than about 210 g, at least about or less than about 220 g, at least about or less than about 230 g, at least about or less than about 240 g, at least about or less than about 250 g, at least about or less than about 260 g, at least about or less than about 270 g, at least about or less than about 280 g, at least about or less than about 290 g, or at least about or less than about 300 g of at least one bile acid sequestrant. In certain embodiments, the dosage unit comprises at least about or less than about 45 mg of at least one proton pump inhibitor and at least about or less than about 10 g, at least about or less than about 20 g, at least about or less than about 30 g, at least about or less than about 40 g, at least about or less than about 50 g, at least about or less than about 60 g, at least about or less than about 70 g, at least about or less than about 80 g, at least about or less than about 90 g, at least about or less than about 100 g, at least about or less than about 110 g, at least about or less than about 120 g, at least about or less than about 130 g, at least about or less than about 140 g, at least about or less than about 150 g, at least about or less than about 160 g, at least about or less than about 170 g, at least about or less than about 180 g, at least about or less than about 190 g, at least about or less than about 200 g, at least about or less than about 210 g, at least about or less than about 220 g, at least about or less than about 230 g, at least about or less than about 240 g, at least about or less than about 250 g, at least about or less than about 260 g, at least about or less than about 270 g, at least about or less than about 280 g, at least about or less than about 290 g, or at least about or less than about 300 g of at least one bile acid sequestrant. In certain embodiments, the dosage unit comprises at least about or less than about 50 mg of at least one proton pump inhibitor and at least about or less than about 10 g, at least about or less than about 20 g, at least about or less than about 30 g, at least about or less than about 40 g, at least about or less than about 50 g, at least about or less than about 60 g, at least about or less than about 70 g, at least about or less than about 80 g, at least about or less than about 90 g, at least about or less than about 100 g, at least about or less than about 110 g, at least about or less than about 120 g, at least about or less than about 130 g, at least about or less than about 140 g, at least about or less than about 150 g, at least about or less than about 160 g, at least about or less than about 170 g, at least about or less than about 180 g, at least about or less than about 190 g, at least about or less than about 200 g, at least about or less than about 210 g, at least about or less than about 220 g, at least about or less than about 230 g, at least about or less than about 240 g, at least about or less than about 250 g, at least about or less than about 260 g, at least about or less than about 270 g, at least about or less than about 280 g, at least about or less than about 290 g, or at least about or less than about 300 g of at least one bile acid sequestrant. In certain embodiments, the dosage unit comprises at least about or less than about 55 mg of at least one proton pump inhibitor and at least about or less than about 10 g, at least about or less than about 20 g, at least about or less than about 30 g, at least about or less than about 40 g, at least about or less than about 50 g, at least about or less than about 60 g, at least about or less than about 70 g, at least about or less than about 80 g, at least about or less than about 90 g, at least about or less than about 100 g, at least about or less than about 110 g, at least about or less than about 120 g, at least about or less than about 130 g, at least about or less than about 140 g, at least about or less than about 150 g, at least about or less than about 160 g, at least about or less than about 170 g, at least about or less than about 180 g, at least about or less than about 190 g, at least about or less than about 200 g, at least about or less than about 210 g, at least about or less than about 220 g, at least about or less than about 230 g, at least about or less than about 240 g, at least about or less than about 250 g, at least about or less than about 260 g, at least about or less than about 270 g, at least about or less than about 280 g, at least about or less than about 290 g, or at least about or less than about 300 g of at least one bile acid sequestrant. In certain embodiments, the dosage unit comprises at least about or less than about 60 mg of at least one proton pump inhibitor and at least about or less than about 10 g, at least about or less than about 20 g, at least about or less than about 30 g, at least about or less than about 40 g, at least about or less than about 50 g, at least about or less than about 60 g, at least about or less than about 70 g, at least about or less than about 80 g, at least about or less than about 90 g, at least about or less than about 100 g, at least about or less than about 110 g, at least about or less than about 120 g, at least about or less than about 130 g, at least about or less than about 140 g, at least about or less than about 150 g, at least about or less than about 160 g, at least about or less than about 170 g, at least about or less than about 180 g, at least about or less than about 190 g, at least about or less than about 200 g, at least about or less than about 210 g, at least about or less than about 220 g, at least about or less than about 230 g, at least about or less than about 240 g, at least about or less than about 250 g, at least about or less than about 260 g, at least about or less than about 270 g, at least about or less than about 280 g, at least about or less than about 290 g, or at least about or less than about 300 g of at least one bile acid sequestrant. In certain embodiments, the dosage unit comprises at least about or less than about 65 mg of at least one proton pump inhibitor and at least about or less than about 10 g, at least about or less than about 20 g, at least about or less than about 30 g, at least about or less than about 40 g, at least about or less than about 50 g, at least about or less than about 60 g, at least about or less than about 70 g, at least about or less than about 80 g, at least about or less than about 90 g, at least about or less than about 100 g, at least about or less than about 110 g, at least about or less than about 120 g, at least about or less than about 130 g, at least about or less than about 140 g, at least about or less than about 150 g, at least about or less than about 160 g, at least about or less than about 170 g, at least about or less than about 180 g, at least about or less than about 190 g, at least about or less than about 200 g, at least about or less than about 210 g, at least about or less than about 220 g, at least about or less than about 230 g, at least about or less than about 240 g, at least about or less than about 250 g, at least about or less than about 260 g, at least about or less than about 270 g, at least about or less than about 280 g, at least about or less than about 290 g, or at least about or less than about 300 g of at least one bile acid sequestrant. In certain embodiments, the dosage unit comprises at least about or less than about 70 mg of at least one proton pump inhibitor and at least about or less than about 10 g, at least about or less than about 20 g, at least about or less than about 30 g, at least about or less than about 40 g, at least about or less than about 50 g, at least about or less than about 60 g, at least about or less than about 70 g, at least about or less than about 80 g, at least about or less than about 90 g, at least about or less than about 100 g, at least about or less than about 110 g, at least about or less than about 120 g, at least about or less than about 130 g, at least about or less than about 140 g, at least about or less than about 150 g, at least about or less than about 160 g, at least about or less than about 170 g, at least about or less than about 180 g, at least about or less than about 190 g, at least about or less than about 200 g, at least about or less than about 210 g, at least about or less than about 220 g, at least about or less than about 230 g, at least about or less than about 240 g, at least about or less than about 250 g, at least about or less than about 260 g, at least about or less than about 270 g, at least about or less than about 280 g, at least about or less than about 290 g, or at least about or less than about 300 g of at least one bile acid sequestrant. In certain embodiments, the dosage unit comprises at least about or less than about 75 mg of at least one proton pump inhibitor and at least about or less than about 10 g, at least about or less than about 20 g, at least about or less than about 30 g, at least about or less than about 40 g, at least about or less than about 50 g, at least about or less than about 60 g, at least about or less than about 70 g, at least about or less than about 80 g, at least about or less than about 90 g, at least about or less than about 100 g, at least about or less than about 110 g, at least about or less than about 120 g, at least about or less than about 130 g, at least about or less than about 140 g, at least about or less than about 150 g, at least about or less than about 160 g, at least about or less than about 170 g, at least about or less than about 180 g, at least about or less than about 190 g, at least about or less than about 200 g, at least about or less than about 210 g, at least about or less than about 220 g, at least about or less than about 230 g, at least about or less than about 240 g, at least about or less than about 250 g, at least about or less than about 260 g, at least about or less than about 270 g, at least about or less than about 280 g, at least about or less than about 290 g, or at least about or less than about 300 g of at least one bile acid sequestrant. In certain embodiments, the dosage unit comprises at least about or less than about 80 mg of at least one proton pump inhibitor and at least about or less than about 10 g, at least about or less than about 20 g, at least about or less than about 30 g, at least about or less than about 40 g, at least about or less than about 50 g, at least about or less than about 60 g, at least about or less than about 70 g, at least about or less than about 80 g, at least about or less than about 90 g, at least about or less than about 100 g, at least about or less than about 110 g, at least about or less than about 120 g, at least about or less than about 130 g, at least about or less than about 140 g, at least about or less than about 150 g, at least about or less than about 160 g, at least about or less than about 170 g, at least about or less than about 180 g, at least about or less than about 190 g, at least about or less than about 200 g, at least about or less than about 210 g, at least about or less than about 220 g, at least about or less than about 230 g, at least about or less than about 240 g, at least about or less than about 250 g, at least about or less than about 260 g, at least about or less than about 270 g, at least about or less than about 280 g, at least about or less than about 290 g, or at least about or less than about 300 g of at least one bile acid sequestrant. In certain embodiments, the dosage unit comprises at least about or less than about 85 mg of at least one proton pump inhibitor and at least about or less than about 10 g, at least about or less than about 20 g, at least about or less than about 30 g, at least about or less than about 40 g, at least about or less than about 50 g, at least about or less than about 60 g, at least about or less than about 70 g, at least about or less than about 80 g, at least about or less than about 90 g, at least about or less than about 100 g, at least about or less than about 110 g, at least about or less than about 120 g, at least about or less than about 130 g, at least about or less than about 140 g, at least about or less than about 150 g, at least about or less than about 160 g, at least about or less than about 170 g, at least about or less than about 180 g, at least about or less than about 190 g, at least about or less than about 200 g, at least about or less than about 210 g, at least about or less than about 220 g, at least about or less than about 230 g, at least about or less than about 240 g, at least about or less than about 250 g, at least about or less than about 260 g, at least about or less than about 270 g, at least about or less than about 280 g, at least about or less than about 290 g, or at least about or less than about 300 g of at least one bile acid sequestrant. In certain embodiments, the dosage unit comprises at least about or less than about 90 mg of at least one proton pump inhibitor and at least about or less than about 10 g, at least about or less than about 20 g, at least about or less than about 30 g, at least about or less than about 40 g, at least about or less than about 50 g, at least about or less than about 60 g, at least about or less than about 70 g, at least about or less than about 80 g, at least about or less than about 90 g, at least about or less than about 100 g, at least about or less than about 110 g, at least about or less than about 120 g, at least about or less than about 130 g, at least about or less than about 140 g, at least about or less than about 150 g, at least about or less than about 160 g, at least about or less than about 170 g, at least about or less than about 180 g, at least about or less than about 190 g, at least about or less than about 200 g, at least about or less than about 210 g, at least about or less than about 220 g, at least about or less than about 230 g, at least about or less than about 240 g, at least about or less than about 250 g, at least about or less than about 260 g, at least about or less than about 270 g, at least about or less than about 280 g, at least about or less than about 290 g, or at least about or less than about 300 g of at least one bile acid sequestrant. In certain embodiments, the dosage unit comprises at least about or less than about 95 mg of at least one proton pump inhibitor and at least about or less than about 10 g, at least about or less than about 20 g, at least about or less than about 30 g, at least about or less than about 40 g, at least about or less than about 50 g, at least about or less than about 60 g, at least about or less than about 70 g, at least about or less than about 80 g, at least about or less than about 90 g, at least about or less than about 100 g, at least about or less than about 110 g, at least about or less than about 120 g, at least about or less than about 130 g, at least about or less than about 140 g, at least about or less than about 150 g, at least about or less than about 160 g, at least about or less than about 170 g, at least about or less than about 180 g, at least about or less than about 190 g, at least about or less than about 200 g, at least about or less than about 210 g, at least about or less than about 220 g, at least about or less than about 230 g, at least about or less than about 240 g, at least about or less than about 250 g, at least about or less than about 260 g, at least about or less than about 270 g, at least about or less than about 280 g, at least about or less than about 290 g, or at least about or less than about 300 g of at least one bile acid sequestrant. In certain embodiments, the dosage unit comprises at least about or less than about 100 mg of at least one proton pump inhibitor and at least about or less than about 10 g, at least about or less than about 20 g, at least about or less than about 30 g, at least about or less than about 40 g, at least about or less than about 50 g, at least about or less than about 60 g, at least about or less than about 70 g, at least about or less than about 80 g, at least about or less than about 90 g, at least about or less than about 100 g, at least about or less than about 110 g, at least about or less than about 120 g, at least about or less than about 130 g, at least about or less than about 140 g, at least about or less than about 150 g, at least about or less than about 160 g, at least about or less than about 170 g, at least about or less than about 180 g, at least about or less than about 190 g, at least about or less than about 200 g, at least about or less than about 210 g, at least about or less than about 220 g, at least about or less than about 230 g, at least about or less than about 240 g, at least about or less than about 250 g, at least about or less than about 260 g, at least about or less than about 270 g, at least about or less than about 280 g, at least about or less than about 290 g, or at least about or less than about 300 g of at least one bile acid sequestrant. In certain embodiments the at least one proton pump inhibitor is omeprazole. In certain embodiments the at least one proton pump inhibitor is esomeprazole. In certain embodiments the at least one proton pump inhibitor is lansoprazole. In certain embodiments the at least one proton pump inhibitor is pantoprazole. In certain embodiments the at least one proton pump inhibitor is rabeprazole. In certain embodiments the at least one proton pump inhibitor is tenatoprazole. In certain embodiments the at least one bile acid sequestrant is cholestyramine. In certain embodiments the at least one bile acid sequestrant is colesevelam. In certain embodiments the at least one bile acid sequestrant is colesevelam-HCl. In certain embodiments the at least one bile acid sequestrant is colestipol. In certain embodiments the at least one proton pump inhibitor is omeprazole and the at least one bile acid sequestrant is cholestyramine. In certain embodiments the at least one proton pump inhibitor is omeprazole and the at least one bile acid sequestrant is colesevelam. In certain embodiments the at least one proton pump inhibitor is omeprazole and the at least one bile acid sequestrant is colesevelam-HCl. In certain embodiments the at least one proton pump inhibitor is omeprazole and the at least one bile acid sequestrant is colestipol. In certain embodiments the at least one proton pump inhibitor is esomeprazole and the at least one bile acid sequestrant is cholestyramine. In certain embodiments the at least one proton pump inhibitor is esomeprazole and the at least one bile acid sequestrant is colesevelam. In certain embodiments the at least one proton pump inhibitor is esomeprazole and the at least one bile acid sequestrant is colesevelam-HCl. In certain embodiments the at least one proton pump inhibitor is esomeprazole and the at least one bile acid sequestrant is colestipol. In certain embodiments the at least one proton pump inhibitor is lansoprazole and the at least one bile acid sequestrant is cholestyramine. In certain embodiments the at least one proton pump inhibitor is lansoprazole and the at least one bile acid sequestrant is colesevelam. In certain embodiments the at least one proton pump inhibitor is lansoprazole and the at least one bile acid sequestrant is colesevelam-HCl. In certain embodiments the at least one proton pump inhibitor is lansoprazole and the at least one bile acid sequestrant is colestipol. In certain embodiments the at least one proton pump inhibitor is pantoprazole and the at least one bile acid sequestrant is cholestyramine. In certain embodiments the at least one proton pump inhibitor is pantoprazole and the at least one bile acid sequestrant is colesevelam. In certain embodiments the at least one proton pump inhibitor is pantoprazole and the at least one bile acid sequestrant is colesevelam-HCl. In certain embodiments the at least one proton pump inhibitor is pantoprazole and the at least one bile acid sequestrant is colestipol. In certain embodiments the at least one proton pump inhibitor is rabeprazole and the at least one bile acid sequestrant is cholestyramine. In certain embodiments the at least one proton pump inhibitor is rabeprazole and the at least one bile acid sequestrant is colesevelam. In certain embodiments the at least one proton pump inhibitor is rabeprazole and the at least one bile acid sequestrant is colesevelam-HCl. In certain embodiments the at least one proton pump inhibitor is rabeprazole and the at least one bile acid sequestrant is colestipol. In certain embodiments the at least one proton pump inhibitor is tenatoprazole and the at least one bile acid sequestrant is cholestyramine. In certain embodiments the at least one proton pump inhibitor is tenatoprazole and the at least one bile acid sequestrant is colesevelam. In certain embodiments the at least one proton pump inhibitor is tenatoprazole and the at least one bile acid sequestrant is colesevelam-HCl. In certain embodiments the at least one proton pump inhibitor is tenatoprazole and the at least one bile acid sequestrant is colestipol. In certain embodiments the dosage unit and daily dose are equivalent. In various embodiments, the dosage unit is administered with food at anytime of the day, without food at anytime of the day, with food after an overnight fast (e.g. with breakfast), at bedtime after a low fat snack. In various embodiments, the dosage unit is administered once a day, twice a day, three times a day, four times a day. The dosage unit can optionally comprise other agents such as at least one antacid, at least one histamine $H_2$-receptor antagonist, or combinations thereof.

Kits

The compounds and pharmaceutical formulations described herein may be contained in a kit. The kit may include single or multiple doses of one or more agent, each packaged or formulated individually, or single or multiple doses of two or more agents packaged or formulated in combination. Thus, one or more agents can be present in a first container, and the kit can optionally include one or more agents in a second container. The container or containers are placed within a package, and the package can optionally include administration or dosage instructions in the form of a label on the package or in the form of an insert included in the packaging of the kit. A kit can include additional components such as syringes or other means for administering the agents as well as diluents or other means for formulation.

Thus, the kits can comprise: a) a pharmaceutical composition comprising at least one bile acid sequestrant and a pharmaceutically acceptable carrier, vehicle (e.g., a gastric-retention vehicle) or diluent; and b) a container or packaging. In another embodiment, the kit can comprise: a) a pharmaceutical composition comprising at least on bile acid sequestrant, at least one proton pump inhibitor, and a pharmaceutically acceptable carrier, vehicle (e.g. a gastric-retention vehicle), or diluent; and b) a container or packaging. The kits may optionally comprise instructions describing a method of using the pharmaceutical compositions in one or more of the methods described herein (e.g., preventing or treating dyspepsia, heartburn, erosive esophagitis, GERD, peptic ulcer, esophagitis, Barrett's esophagus, and esophageal adenocarcinoma). The kit may optionally comprise a second pharmaceutical composition comprising any of at least one antacid, at least one histamine $H_2$-receptor antagonist, at least one GABA-B agonist, at least one prodrug of a GABA-B agonist, at least one protease inhibitor, or combinations thereof and a pharmaceutically acceptable carrier, vehicle or diluent. The pharmaceutical composition comprising the at least one bile acid sequestrant (or the at least one bile acid sequestrant and at least one proton pump inhibitor), and the second pharmaceutical composition contained in the kit may be optionally combined in the same pharmaceutical composition.

A kit includes a container or packaging for containing the pharmaceutical compositions and may also include divided containers such as a divided bottle or a divided foil packet. The container can be, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. It is feasible that more than one container can be used together in a single package to market a single dosage form. For example, tablets may be contained in a bottle which is in turn contained within a box.

An example of a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It maybe desirable to provide a written memory aid containing information and/or instructions for the physician, pharmacist or subject regarding when the medication is to be taken. A "daily dose" can be a single tablet or capsule or several tablets or capsules to be taken on a given day. When the kit contains separate compositions, a daily dose of one or more compositions of the kit can consist of one tablet or capsule while a daily dose of another one or more compositions of the kit can consist of several tablets or capsules. A kit can take the form of a dispenser designed to dispense the daily doses one at a time in the order of their intended use. The dispenser can be equipped with a memory-aid, so as to further facilitate compliance with the regimen. An example of such a memory-aid is a mechanical counter which indicates the number of daily doses that have been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Various patent and/or scientific literature references have been referred to throughout this application. The disclosures of these publications in their entireties are hereby incorporated by reference as if written herein. In view of the above description and the examples below, one of ordinary skill in the art will be able to practice the disclosure as claimed without undue experimentation. The foregoing will be better understood with reference to the following Examples that detail certain procedures for the preparation of formulations according to the present disclosure. All references made to these Examples are for the purposes of illustration. The following Examples should not be considered exhaustive, but merely illustrative of only a few of the many embodiments contemplated by the present disclosure.

EXAMPLES

Example 1

Effects of bile acid sequestrant alone and in combination, on esophageal epithelial cells. Epithelial cells are isolated from normal human esophagus and Barrett's esophagus samples (e.g. biopsies) and established in monolayer cell cultures as described in Burg-Kurland et al. (1986) Methods in Cell Science 10:227-232 or cultured as described in Trier, J. S. (1980) Methods Cell Biol. 18:365-384. Barrett's Esophagus is induced or exacerbated by the addition of bile acid(s), stomach acid(s), and/or other acids or acidified media (for example as in Fitzgerald et al. (1996) J Clin Invest 98:2120-8). Acid exposure is continuous or as a timed pulse (e.g. 1 hour). Test article (e.g. vehicle alone, proton pump inhibitor, bile acid sequestrant, proton pump inhibitor and bile acid sequestrant) at various doses (for example, as described in the present application) is added either before, simultaneously with, or after acid addition. Barrett's Esophagus development is monitored visually by microscope by the transformation of squamous cells to columnar cells. Cell proliferation is determined by tritiated thymidine incorporation and proliferating cell nuclear antigen expression. Cell differentiation is determined by villin expression (see Fitzgerald et al. supra).

Example 2

Effects of bile acid sequestrant, alone and in combination, on in vivo model of Barrett's Esophagus. Test article (e.g. vehicle alone, proton pump inhibitor, bile acid sequestrant, proton pump inhibitor and bile acid sequestrant) at various doses (for example, as described in the present application) is evaluated for effects on 2 different rodent models of Barrett's Esophagus, for example as described in Buskens et al. (2006) *J Surg Res*. 135:337-44.

Although the foregoing disclosure has been described and depicted in terms of certain preferred embodiments, other specific embodiments may be effected by those skilled in the art to accomplish the same objectives and without departing from the true spirit of the scope of the present disclosure. Accordingly, the scope of the Applicant's disclosure is to be determined by reference to the attached claims, which are not limited to any of the particular embodiments disclosed herein.

I claim:

1. A sustained-release pharmaceutical dosage form for oral administration to a subject in need thereof comprising an amount of at least one bile acid sequestrant that is in a range from 0.1 g to 1.0 g, wherein the at least one bile acid sequestrant is selected from the group consisting of colesevelam, colesevelam hydrochloride, colestipol, sevelamer and combinations thereof, and a gastric-retention vehicle composition comprising one or more hydrogels, wherein said dosage form expands upon contact with gastric fluid.

2. The sustained-release pharmaceutical dosage form for oral administration according to claim 1, further comprising a therapeutically effective amount of at least one proton pump inhibitor in a range from 1 mg to 200 mg.

3. The sustained-release pharmaceutical dosage form for oral administration of claim 2, wherein the at least one proton pump inhibitor is selected from omeprazole, esomeprazole, lansoprazole, pantoprazole, rabeprazole, tenatoprazole, leminoprazole, dontoprazole and ransoprazole.

4. The sustained-release pharmaceutical dosage form for oral administration of claim 3, wherein the at least one proton pump inhibitor is omeprazole.

5. The sustained-release pharmaceutical dosage form for oral administration of claim 1 characterized in that the dosage form is retained in a person's stomach for a period of three hours or more following ingestion.

6. The sustained-release pharmaceutical dosage form for oral administration of claim 2 characterized in that the dosage form is retained in a person's stomach for a period of three hours or more following ingestion.

7. The sustained-release pharmaceutical dosage form for oral administration of claim 5, wherein the percentage of active ingredient(s) is present in an amount from between 10% to about 75% of the total weight.

8. The sustained-release pharmaceutical dosage form for oral administration of claim 6, wherein the percentage of active ingredient(s) is present in an amount from between 10% to about 75% of the total weight.

9. A method for mitigating the presence of bile acid in the upper gastrointestinal (GI) tract, comprising administering to a patient a therapeutically effective amount of the sustained-release pharmaceutical dosage form for oral administration according claim 1.

10. A method for mitigating the presence of bile acid in the upper gastrointestinal (GI) tract, comprising administering to a patient that has or is at risk of developing said disorder a therapeutically effective amount of the sustained-release pharmaceutical dosage form for oral administration according to claim 2.

11. The method according to claim 9, further comprising: simultaneously, separately, or sequentially administering to said patient at least one proton pump inhibitor.

12. The method according to claim 10, further comprising: simultaneously, separately, or sequentially administering to said patient at least one proton pump inhibitor.

* * * * *